(12) United States Patent
Kohno et al.

(10) Patent No.: US 8,569,270 B2
(45) Date of Patent: Oct. 29, 2013

(54) DIPHENYL SULFIDE DERIVATIVES AND MEDICINES CONTAINING SAME AS ACTIVE INGREDIENT

(75) Inventors: Yasushi Kohno, Tochigi (JP); Kiyoshi Fujii, Tochigi (JP); Momoko Taru, Tochigi (JP); Keita Miyoshi, Tochigi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/382,011

(22) PCT Filed: Jul. 8, 2010

(86) PCT No.: PCT/JP2010/004453
§ 371 (c)(1),
(2), (4) Date: Jan. 3, 2012

(87) PCT Pub. No.: WO2011/004604
PCT Pub. Date: Jan. 13, 2011

(65) Prior Publication Data
US 2012/0101068 A1    Apr. 26, 2012

(30) Foreign Application Priority Data

Jul. 9, 2009 (JP) ................. 2009-162289
May 14, 2010 (JP) ................. 2010-112138

(51) Int. Cl.
*A61K 31/663* (2006.01)
*C07F 9/09* (2006.01)

(52) U.S. Cl.
USPC ............ 514/114; 514/143; 558/166

(58) Field of Classification Search
USPC .......................... 558/166; 514/114
See application file for complete search history.

(56) References Cited

U.S. PATENT DOCUMENTS

| | | |
|---|---|---|
| 2006/0160771 A1 | 7/2006 | Kohno et al. |
| 2008/0275008 A1 | 11/2008 | Kohno et al. |
| 2009/0325907 A1 | 12/2009 | Kohno et al. |

FOREIGN PATENT DOCUMENTS

| | | |
|---|---|---|
| EP | 1 602 660 | 12/2005 |
| EP | 2 058 317 | 5/2009 |
| EP | 2 172 472 | 4/2010 |
| JP | 2008-239546 | 10/2008 |
| JP | 2010-13407 | 1/2010 |
| JP | 2010-77053 | 4/2010 |
| WO | 2004/074297 | 9/2004 |
| WO | 2008/018427 | 2/2008 |

OTHER PUBLICATIONS

Marsolais et al, 2009, Nature Reviews: Drug Discovery, vol. 8, p. 297-307.*
Murakami, 2010, Mol. Pharmacol, vol. 77, p. 704-713.*
International Preliminary Report on Patentability issued Feb. 14, 2012 in International Application No. PCT/JP2010/004453.
International Search Report issued Oct. 5, 2010 in International (PCT) Application No. PCT/JP2010/004453.

* cited by examiner

*Primary Examiner* — Yong Chu
*Assistant Examiner* — Karen Cheng
(74) *Attorney, Agent, or Firm* — Wenderoth, Lind & Ponack, L.L.P.

(57) ABSTRACT

Provided are diphenyl sulfide derivatives which have excellent S1P3 antagonistic activity and are useful as drugs. Intensive studies have been made for the purpose of creating a compound having S1P3 antagonistic activity. As a result of the intensive studies, it has been found that diphenyl sulfide derivatives represented by general formula (1) have excellent S1P3 antagonistic activity. In general formula (1), $R^1$ is a hydrogen atom or the like; $R^2$ is an optionally substituted alkyl group having 1 to 6 carbon atoms, or the like; X is a methylene group which may be substituted with one or two fluorine atoms, or the like; Y is a hydrogen atom or the like; and Z is a halogen atom.

[Formula 1]

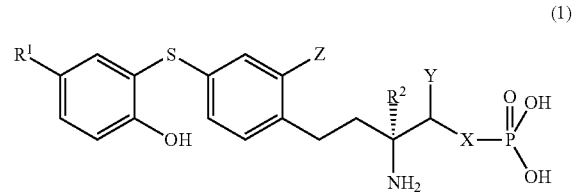

(1)

10 Claims, No Drawings

DIPHENYL SULFIDE DERIVATIVES AND MEDICINES CONTAINING SAME AS ACTIVE INGREDIENT

This is a National Stage Application of International Application No. PCT/JP2010/004453, filed Jul. 8, 2010, which claims priority to Japanese Application No. 2009-162289, filed Jul. 9, 2009, and Japanese Application No. 2010-112138, filed May 14, 2010.

TECHNICAL FIELD

The present invention relates to a novel diphenyl sulfide derivative that is effective as a medicine, or a pharmaceutically acceptable salt or hydrate thereof, and a sphingosine-1-phosphate 3 (S1P3) receptor-antagonist and a medicine containing the same as an active ingredient.

BACKGROUND ART

Sphingosine-1-phosphate (S1P) was considered to be merely an intermediary metabolite in sphingosine metabolism. However, it has been reported that S1P has a cell growth promoting action and a control action of a cell motility function, and it is now clear that S1P is a new lipid mediator that exhibits various physiological actions, such as an apoptosis action, a cell morphology regulation action, and vasoconstriction (Non-Patent Literatures 1 and 2).

This S1P combines two actions, an action as an intracellular second messenger and an action as an intercellular mediator. Studies into S1P's action as an intercellular mediator are especially active. It has been reported that information is transmitted via a plurality of G protein-coupled receptors present on the cell membrane surface (Endothelial Differentiation Gene, EDG) (Non-Patent Literatures 1 and 3). Currently, five sub-types of S1P receptors are known, including Edg-1, Edg-3, Edg-5, Edg-6, and Edg-8 which are called as $S1P_1$, $S1P_3$, $S1P_2$, $S1P_4$, and $S1P_5$, respectively.

From various studies into these S1P receptors, it has been reported that so-called S1P receptor regulator, which exhibits an agonistic or antagonistic action against this receptor, is effective against a wide range of diseases. Patent Literature 2 and Non-Patent Literatures 4 to 7 report that the S1P3 antagonist is effective as a therapeutic or preventive medicine for respiratory tract contraction, bronchial asthma, chronic obstructive pulmonary disease (COPD), pulmonary emphysema, tracheal stenosis, diffuse panbronchiolitis, bronchitis resulting from infection, connective tissue disease, or transplantation, diffuse pulmonary hamartoangiomyomatosis, adult respiratory distress syndrome (ARDS), interstitial pneumonitis, lung cancer, pneumonia hypersensitivity, idiopathic interstitial pneumonia, fibrosis of the lung, sepsis, or cytokine storm caused by an influenza virus or RS virus infection.

Further, Patent Literatures 3 to 6 show that the S1P3 antagonist is also effective against arterial sclerosis, blood vessel intimal hypertrophy, solid tumors, diabetic retinopathy, rheumatoid arthritis, cardiac arrest, ischemia-reperfusion disorders, cerebral blood vessel spasms after subarachnoid bleeding, angina pectoris or myocardial infarction caused by coronary vessel spasms, glomerulonephritis, thrombosis, lung disease caused by pulmonary edema such as ARDS, cardiac arrhythmia, eye disease, eye hypertension, glaucoma, glaucomatous retinopathy, optic neuropathy, macula-lutea degeneration and the like.

Further, although currently there are recombinants form of human activated protein C (rhAPC) in medicines that are effective as sepsis therapeutic medicines, rhAPC may also cause hemorrhaging as a side effect. Therefore, there is a need to develop a novel sepsis therapeutic or preventive medicine that does not exhibit such side effects. Non-Patent Literatures 5 and 7 report that the S1P3 receptor contributes to multiple organ failure caused by sepsis based on analysis using S1P3 knockout mice, thereby suggesting that the S1P3 antagonist may be effective as a sepsis therapeutic or preventive medicine. In addition, it has been reported that the S1P1 antagonist increases vascular wall permeability, and causes pulmonary edema (Non-Patent Literature 8). Therefore, in order for a novel sepsis therapeutic or preventive medicine to have a high level of safety, that therapeutic or preventive medicine should have a weak S1P1 antagonistic action, preferably exhibit an S1P1 agonistic action, and more preferably not exhibit an action against the S1P1 receptor.

Known S1P receptor regulators include, for example, the compounds represented by the following general formula (A) described in Patent Literature 1,

[Formula 1]

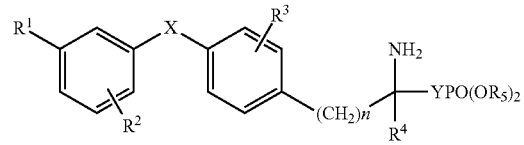

(A)

(In the formula (A), $R^1$ represents a hydrogen atom, a halogen atom, a halogenated or unhalogenated lower alkyl group having 1 to 4 carbon atoms, a hydroxy group, a phenyl group, an aralkyl group, a lower alkoxy group having 1 to 4 carbon atoms, a trifluoromethyloxy group, an optionally substituted aralkyloxy group, an optionally substituted phenoxy group, a cyclohexylmethyloxy group, an optionally substituted aralkyloxy group, a pyridylmethyloxy group, a cinnamyloxy group, a naphthylmethyloxy group, a phenoxymethyl group, a hydroxymethyl group, a hydroxyethyl group, a lower alkylthio group having 1 to 4 carbon atoms, a lower alkylsulfinyl group having 1 to 4 carbon atoms, a lower alkylsulfonyl group having 1 to 4 carbon atoms, a benzylthio group, an acetyl group, a nitro group, or a cyano group; $R^2$ represents a hydrogen atom, a halogen atom, a halogenated or unhalogenated lower alkyl group having 1 to 4 carbon atoms, a lower alkoxy group having 1 to 4 carbon atoms, an aralkyl group, or an aralkyloxy group; $R^3$ represents a hydrogen atom, a halogen atom, a trifluoromethyl group, a lower alkyl group having 1 to 4 carbon atoms, a lower alkoxy group having 1 to 4 carbon atoms, a hydroxy group, a benzyloxy group, a phenyl group, a lower alkoxymethyl group having 1 to 4 carbon atoms or a lower alkylthio group having 1 to 4 carbon atoms; $R^4$ represents a hydrogen atom, a halogen atom, a trifluoromethyl group, a lower alkyl group having 1 to 4 carbon atoms, a lower alkoxymethyl group having 1 to 4 carbon atoms, a lower alkylthiomethyl group having 1 to 4 carbon atoms, a hydroxymethyl group, a phenyl group, or an aralkyl group; $R^5$ represents a hydrogen atom or a lower alkyl group having 1 to 4 carbon atoms; X represents O, S, SO, or SO2; and Y represents —CH2O—, —CH2-, —CH=CH—, —CF=CF—, —CH2CH2-, —CH2CFH—, —CH2CF2-, or —CH(OH)CF2-.).

However, Patent Literature 1 does not include 2-aminophosphoric acid monoester derivatives or 3-aminophosphonic acid derivatives having a diphenyl sulfide skeleton in which a hydroxyl group is substituted for a phenyl group. Further, the fact that 2-aminophosphoric acid monoester derivatives or 3-aminophosphonic acid derivatives having such a structure exhibit an excellent S1P3 receptor-antagonistic action is also not known.

Other examples of known S1P receptor regulators include the compounds represented by the following general formula (B) in Patent Literature 6,

[Formula 2]

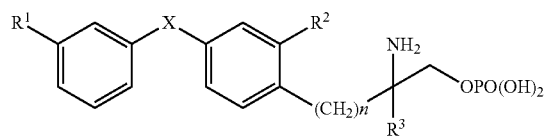

(B)

(In the formula (B), $R^1$ represents a chlorine atom, a linear alkyl group having 1 to 3 carbon atoms, or a trifluoromethyl group; $R^2$ represents a fluorine atom or a chlorine atom; $R^3$ represents a linear alkyl group having 1 to 3 carbon atoms; X represents an oxygen atom or a sulfur atom; and n denotes an integer of 2 or 3.).

Further, among the compounds represented by the general formula (B), it has been reported that the optically active compounds represented by the general formula (Ba), have a weak S1P3 agonistic action and an excellent agonistic action against S1P1 and/or S1P4.

[Formula 3]

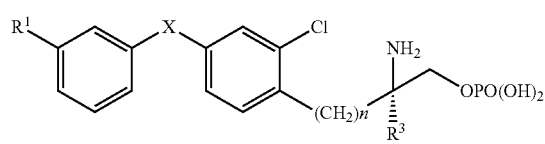

(Ba)

(In the formula (Ba), $R^1$, $R^3$, and X are as defined above.)

However, the compounds having an inverse asymmetric center to the optically active compounds represented by the general formula (Ba), are not known. Further, the fact that such optically active compounds exhibit an excellent S1P3 receptor-antagonistic action is also not known.

Patent Literature 1 WO04074297 pamphlet
Patent Literature 2 WO03020313 pamphlet
Patent Literature 3 Japanese Patent Application Laid-Open No. 2005-247691
Patent Literature 4 WO07043568 pamphlet
Patent Literature 5 WO06063033 pamphlet
Patent Literature 6 WO08018427 pamphlet
Non-Patent Literature 1 Y. Takuma et al., Mol. Cell. Endocrinol., 177, 3 (2001).
Non-Patent Literature 2 Y. Igarashi, Ann, N.Y. Acad. Sci., 845, 19 (1998).
Non-Patent Literature 3 H. Okazaki et al., Biochem. Biophs. Res. Commun., 190, 1104 (1993).
Non-Patent Literature 4 Y. Gon et. al., Proc Natl Acad Sci USA. 102(26), 9270 (2005).
Non-Patent Literature 5 F. Nissen et al., Nature, 452, 654 (2008)
Non-Patent Literature 6 D. Christina et al., Am. J. Pathol., 170(1), 281 (2007)
Non-Patent Literature 7 F. Nissen et al., Blood, 113(12), 2859 (2009)
Non-Patent Literature 8 M. G. Sanna et al., Nature Chemical biology, 2, 434 (2006)

SUMMARY OF THE INVENTION

Problems to be Solved by the Invention

It is an object of the present invention to provide a diphenyl sulfide derivative having an excellent S1P3 antagonistic activity.

Means for Solving the Problems

As a result of intensive studies into the S1P3 antagonist, the present inventors discovered that a novel diphenyl sulfide derivative has an excellent S1P3 antagonistic action, thereby completing the present invention.

Specifically, a first aspect of the invention relates to a diphenyl sulfide derivative, or a pharmaceutically acceptable salt or hydrate thereof, represented by the following general formula (1),

[Formula 4]

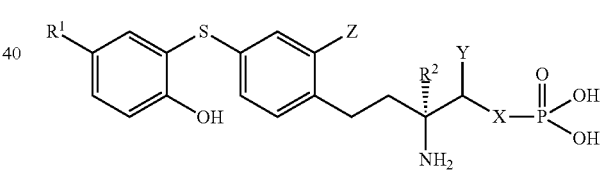

(1)

(In the formula (1), $R^1$ represents a hydrogen atom, a halogen atom, a trifluoromethyl group, an optionally substituted alkyl group having 1 to 6 carbon atoms, an optionally substituted cycloalkyl group having 3 to 6 carbon atoms, an optionally substituted aryl group having 6 to 10 carbon atoms, an optionally substituted alkoxy group having 1 to 4 carbon atoms, an optionally substituted benzyloxy group, an optionally substituted acyl group having 1 to 4 carbon atoms, a cyano group, or a carboxyl group; $R^2$ represents an optionally substituted alkyl group having 1 to 6 carbon atoms or an optionally substituted alkenyl group having 2 to 6 carbon atoms; X represents a methylene group which may be substituted with 1 or 2 fluorine atoms or represents an oxygen atom; Y represents a hydrogen atom or an optionally substituted alkyl group having 1 to 6 carbon atoms; and Z represents a halogen atom).

Further, a second aspect of the invention relates to the diphenyl sulfide derivative according to the first aspect of the invention, or a pharmaceutically acceptable salt or hydrate thereof, wherein the compound represented by the general formula (1) is represented by the general formula (1a),

[Formula 5]

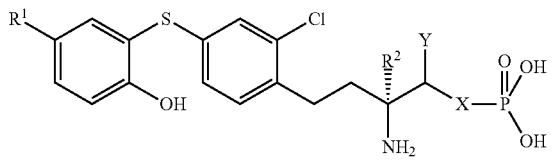

(In the formula (1a), $R^1$, $R^2$, X, and Y are as defined above).

In addition, a third aspect of the invention relates to the diphenyl sulfide derivative according to the first aspect of the invention, or a pharmaceutically acceptable salt or hydrate thereof, wherein the compound represented by the general formula (1) is represented by the general formula (1b),

[Formula 6]

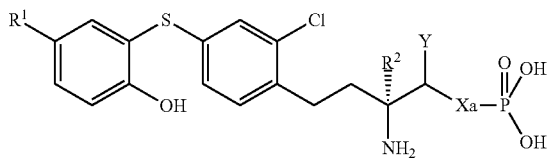

(In the formula (1b), Xa represents an oxygen atom or —CH$_2$—, and $R^1$, $R^2$, and Y are as defined above).

Still further, a fourth aspect of the invention relates to the diphenyl sulfide derivative according to the first aspect of the invention, or a pharmaceutically acceptable salt or hydrate thereof, wherein the compound represented by the general formula (1) is represented by the general formula (1c),

[Formula 7]

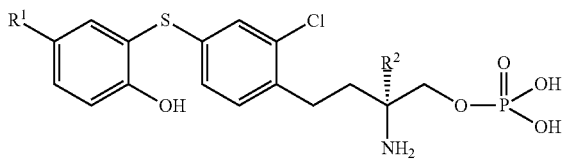

(In the formula (1c), $R^1$ and $R^2$ are as defined above).

In addition, a fifth aspect of the invention relates to the diphenyl sulfide derivative according to the fourth aspect of the invention, or a pharmaceutically acceptable salt or hydrate thereof, wherein $R^1$ represents a trifluoromethyl group, an alkyl group having 1 to 6 carbon atoms, a cycloalkyl group having 3 to 6 carbon atoms, an aryl group having 6 to 10 carbon atoms, or a benzyloxy group.

Still further, a sixth aspect of the invention relates to the diphenyl sulfide derivative according to the first aspect of the invention, or a pharmaceutically acceptable salt or hydrate thereof, wherein the compound represented by the general formula (1) is
(S)-2-amino-4-[2-chloro-4-(2-hydroxy-5-trifluoromethylphenylthio)phenyl]-2-propylbutylphosphoric acid monoester,
(R)-2-allyl-2-amino-4-[2-chloro-4-(2-hydroxy-5-trifluoromethylphenylthio)phenyl]butylphosphoric acid monoester,
(S)-2-amino-4-[2-chloro-4-(2-hydroxy-5-trifluoromethylphenylthio)phenyl]-2-methylbutylphosphoric acid monoester,
(S)-2-amino-4-[2-chloro-4-(2-hydroxy-5-isopropylphenylthio)phenyl]-2-methylbutylphosphoric acid monoester,
(S)-2-amino-4-[2-chloro-4-(5-cyclopropyl-2-hydroxyphenylthio)phenyl]-2-methylbutylphosphoric acid monoester,
(S)-2-amino-4-[4-(5-benzyloxy-2-hydroxyphenylthio)-2-chlorophenyl]-2-methylbutylphosphoric acid monoester,
(S)-2-amino-4-[2-chloro-4-(2-hydroxy-5-propylphenylthio)phenyl]-2-propylbutylphosphoric acid monoester,
(S)-2-amino-4-[2-chloro-4-(2-hydroxy-5-isopropylphenylthio)phenyl]-2-propylbutylphosphoric acid monoester,
(S)-2-amino-4-[2-chloro-4-(5-cyclopropyl-2-hydroxyphenylthio)phenyl]-2-propylbutylphosphoric acid monoester,
(S)-2-amino-4-[(4-(5-t-butyl-2-hydroxyphenylthio)-2-chlorophenyl]-2-propylbutylphosphoric acid monoester,
(S)-2-amino-4-[2-chloro-4-(2-hydroxy-5-biphenylthio)phenyl]-2-propylbutylphosphoric acid monoester, or
(S)-2-amino-4-[4-(5-benzyloxy-2-hydroxyphenylthio)-2-chlorophenyl]-2-propylbutylphosphoric acid monoester.

In addition, a seventh aspect of the invention relates to the diphenyl sulfide derivative according to the first aspect of the invention, or a pharmaceutically acceptable salt or hydrate thereof, wherein the compound represented by the general formula (1) is
(−)-2-amino-4-[2-chloro-4-(2-hydroxy-5-trifluoromethylphenylthio)phenyl]-2-propylbutylphosphoric acid monoester,
(−)-2-allyl-2-amino-4-[2-chloro-4-(2-hydroxy-5-trifluoromethyl phenylthio)phenyl]butylphosphoric acid monoester,
(−)-2-amino-4-[2-chloro-4-(2-hydroxy-5-trifluoromethylphenylthio)phenyl]-2-methylbutylphoshoric acid monoester,
(−)-2-amino-4-[2-chloro-4-(2-hydroxy-5-isopropylphenylthio)phenyl]-2-methylbutylphosphoric acid monoester,
(−)-2-amino-4-[2-chloro-4-(5-cyclopropyl-2-hydroxyphenylthio)phenyl]-2-methylbutylphosphoric acid monoester,
(−)-2-amino-4-[4-(5-benzyloxy-2-hydroxyphenylthio)-2-chlorophenyl]-2-methylbutylphosphoric acid monoester,
(−)-2-amino-4-[2-chloro-4-(2-hydroxy-5-propylphenylthio)phenyl]-2-propylbutylphosphoric acid monoester,
(−)-2-amino-4-[2-chloro-4-(2-hydroxy-5-isopropylphenylthio)phenyl]-2-propylbutylphosphoric acid monoester,
(−)-2-amino-4-[2-chloro-4-(5-cyclopropyl-2-hydroxyphenylthio)phenyl]-2-propylbutylphosphoric acid monoester,
(−)-2-amino-4-[4-(5-t-butyl-2-hydroxyphenylthio)-2-chlorophenyl]-2-propylbutylphosphoric acid monoester,
(−)-2-amino-4-[2-chloro-4-(2-hydroxy-5-biphenylthio)phenyl]-2-propylbutylphosphoric acid monoester, or
(−)-2-amino-4-[4-(5-benzyloxy-2-hydroxyphenylthio)-2-chlorophenyl]-2-propylbutylphosphoric acid monoester.

Still further, an eighth aspect of the invention relates to a medicine that is based on a sphingosine-1-phosphate 3 (S1P3) receptor-antagonistic action, which comprises as an active ingredient the diphenyl sulfide derivative according to any one of the first to seventh aspects of the invention, or a pharmaceutically acceptable salt or hydrate thereof.

In addition, a ninth aspect of the invention relates to the medicine according to the eighth aspect of the invention, wherein the medicine is a therapeutic or preventive medicine for respiratory tract contraction, bronchial asthma, chronic obstructive pulmonary disease (COPD), pulmonary emphysema, tracheal stenosis, diffuse panbronchiolitis, bronchitis resulting from infection, connective tissue disease, or transplantation, diffuse pulmonary hamartoangiomyomatosis, adult respiratory distress syndrome (ARDS), interstitial pneumonitis, lung cancer, pneumonia hypersensitivity, idiopathic interstitial pneumonia, fibrosis of the lung, sepsis, or cytokine storm caused by an influenza virus or RS virus infection.

Still further, a tenth aspect of the invention relates to the medicine according to the eighth aspect of the invention, wherein the medicine is a therapeutic medicine for arterial sclerosis, blood vessel intimal hypertrophy, solid tumors, diabetic retinopathy, rheumatoid arthritis, cardiac arrest, ischemia-reperfusion disorders, cerebral blood vessel spasms after subarachnoid bleeding, angina pectoris or myocardial infarction caused by coronary vessel spasms, glomerulonephritis, thrombosis, lung disease caused by pulmonary edema, cardiac arrhythmia, eye disease, eye hypertension, glaucoma, glaucomatous retinopathy, optic neuropathy, or macula-lutea degeneration.

In addition, an eleventh aspect of the invention relates to the medicine according to the eighth aspect of the invention, wherein the medicine is a therapeutic or preventive medicine for sepsis.

Further, a twelfth aspect of the invention relates to a pharmaceutical composition comprising the diphenyl sulfide derivative according to any one of the first to seventh aspects of the invention, or a pharmaceutically acceptable salt or hydrate thereof, and a pharmaceutically acceptable carrier.

In addition, a thirteenth aspect of the invention relates to a use of the diphenyl sulfide derivative according to any one of the first to seventh aspects of the invention, or a pharmaceutically acceptable salt or hydrate thereof, in manufacture of a medicine based on an S1P3 receptor-antagonistic action.

Further, a fourteenth aspect of the invention relates to the use according to the thirteenth aspect of the invention, wherein the medicine based on an S1P3 receptor-antagonistic action is a therapeutic or preventive medicine for respiratory tract contraction, bronchial asthma, chronic obstructive pulmonary disease (COPD), pulmonary emphysema, tracheal stenosis, diffuse panbronchiolitis, bronchitis resulting from infection, connective tissue disease, or transplantation, diffuse pulmonary hamartoangiomyomatosis, adult respiratory distress syndrome (ARDS), interstitial pneumonitis, lung cancer, pneumonia hypersensitivity, idiopathic interstitial pneumonia, fibrosis of the lung, sepsis, or cytokine storm caused by an influenza virus or RS virus infection.

In addition, a fifteenth aspect of the invention relates to the use according to the thirteenth aspect of the invention, wherein the medicine based on an S1P3 receptor-antagonistic action is a therapeutic medicine for arterial sclerosis, blood vessel intimal hypertrophy, solid tumors, diabetic retinopathy, rheumatoid arthritis, cardiac arrest, ischemia-reperfusion disorders, cerebral blood vessel spasms after subarachnoid bleeding, angina pectoris or myocardial infarction caused by coronary vessel spasms, glomerulonephritis, thrombosis, lung disease caused by pulmonary edema, cardiac arrhythmia, eye disease, eye hypertension, glaucoma, glaucomatous retinopathy, optic neuropathy, or macula-lutea degeneration.

Further, a sixteenth aspect of the invention relates to the use according to the thirteenth aspect of the invention, wherein the medicine based on an S1P3 receptor-antagonistic action is a therapeutic or preventive medicine for sepsis.

In addition, a seventeenth aspect of the invention relates to the diphenyl sulfide derivative according to anyone of the first to seventh aspects of the invention, or a pharmaceutically acceptable salt or hydrate thereof, for use in inducing an S1P3 receptor-antagonistic action.

Further, an eighteenth aspect of the invention relates to the diphenyl sulfide derivative according to any one of the first to seventh aspects of the invention, or a pharmaceutically acceptable salt or hydrate thereof, for use in treatment or prevention of respiratory tract contraction, bronchial asthma, chronic obstructive pulmonary disease (COPD), pulmonary emphysema, tracheal stenosis, diffuse panbronchiolitis, bronchitis resulting from infection, connective tissue disease, or transplantation, diffuse pulmonary hamartoangiomyomatosis, adult respiratory distress syndrome (ARDS), interstitial pneumonitis, lung cancer, pneumonia hypersensitivity, idiopathic interstitial pneumonia, fibrosis of the lung, sepsis, or cytokine storm caused by an influenza virus or RS virus infection.

In addition, a nineteenth aspect of the invention relates to the diphenyl sulfide derivative according to any one of the first to seventh aspects of the invention, or a pharmaceutically acceptable salt or hydrate thereof, for use in treatment of arterial sclerosis, blood vessel intimal hypertrophy, solid tumors, diabetic retinopathy, rheumatoid arthritis, cardiac arrest, ischemia-reperfusion disorders, cerebral blood vessel spasms after subarachnoid bleeding, angina pectoris or myocardial infarction caused by coronary vessel spasms, glomerulonephritis, thrombosis, lung disease caused by pulmonary edema, cardiac arrhythmia, eye disease, eye hypertension, glaucoma, glaucomatous retinopathy, optic neuropathy, or macula-lutea degeneration.

Further, a twentieth aspect of the invention relates to the diphenyl sulfide derivative according to any one of the first to seventh aspects of the invention, or a pharmaceutically acceptable salt or hydrate thereof, for use in treatment or prevention of sepsis.

In addition, a twenty-first aspect of the invention relates to the diphenyl sulfide derivative according to any one of the first to seventh aspects of the invention, or a pharmaceutically acceptable salt or hydrate thereof, for inducing an S1P3 receptor-antagonistic action.

Further, a twenty-second aspect of the invention relates to a method for inducing an S1P3 receptor-antagonistic action in a target, comprising administrating effective amount of the diphenyl sulfide derivative according to any one of the first to seventh aspects of the invention, or a pharmaceutically acceptable salt or hydrate thereof to a target requiring the induction of an S1P3 receptor-antagonistic action.

Advantageous Effects of the Invention

According to the present invention, a diphenyl sulfide derivative having an excellent S1P3 antagonistic action can be provided. The inventive compound is effective as a preventive or a therapy for sepsis, respiratory tract contraction, bronchial asthma, chronic obstructive pulmonary disease (COPD), pulmonary emphysema, tracheal stenosis, diffuse panbronchiolitis, bronchitis resulting from infection, connective tissue disease, or transplantation, diffuse pulmonary hamartoangiomyomatosis, adult respiratory distress syndrome (ARDS), interstitial pneumonitis, lung cancer, pneumonia hypersensitivity, idiopathic interstitial pneumonia, fibrosis of the lung, or cytokine storm (hyperproduction) caused by an influenza virus or RS virus infection, arterial sclerosis, blood vessel intimal hypertrophy, solid tumors, diabetic retinopathy, rheumatoid arthritis, cardiac arrest, ischemia-reperfusion disorders, cerebral blood vessel spasms after subarachnoid bleeding, angina pectoris or myocardial infarction caused by coronary vessel spasms, glomerulonephritis, thrombosis, lung disease caused by pulmonary edema such as ARDS, cardiac arrhythmia, eye disease, eye hypertension, glaucoma, glaucomatous retinopathy, optic neuropathy, and macula-lutea degeneration.

MODE FOR CARRYING OUT THE INVENTION

The "halogen atom" used in the present invention is a fluorine atom, a chlorine atom, a bromine atom, or an iodine atom. Examples of the "alkyl group having 1 to 6 carbon atoms" include a linear hydrocarbon group having 1 to 6 carbon atoms, such as a methyl group, an ethyl group, an n-propyl group, an n-butyl group, an n-pentyl group, or an n-hexyl group, and a branched hydrocarbon group having 1 to 6 carbon atoms, such as an i-propyl group or a t-butyl group. Examples of the "cycloalkyl group having 3 to 6 carbon atoms" include a cyclopropyl group, a cyclobutyl group, a cyclopentyl group, and a cyclohexyl group. Examples of the "aryl group having 6 to 10 carbon atoms" include a phenyl group and a naphthyl group. Examples of the "alkoxy group having 1 to 4 carbon atoms" include a methoxy group, an ethoxy group, an n-propoxy group, an n-butoxy group, an i-propoxy group, and a t-butoxy group. Examples of the "alkenyl group having 2 to 6 carbon atoms" include an allyl group. Examples of the "acyl group having 1 to 4 carbon atoms" include an acetyl group. Examples of the "methylene group which may be substituted with 1 or 2 fluorine atoms" include —CH$_2$—, —CHF—, and —CF$_2$—.

Further, the "alkyl group having 1 to 6 carbon atoms," the "cycloalkyl group having 3 to 6 carbon atoms," the "aryl group having 6 to 10 carbon atoms," the "alkoxy group having 1 to 4 carbon atoms," the "benzyloxy group," the "acyl group having 1 to 4 carbon atoms," and the "alkenyl group having 2 to 6 carbon atoms" may have a substituent. Examples of this "substituent" include a halogen atom, a trifluoromethyl group, an alkyl group having 1 to 6 carbon atoms, a cycloalkyl group having 3 to 6 carbon atoms, an aryl group having 6 to 10 carbon atoms, an alkoxy group having 1 to 4 carbon atoms, a benzyloxy group, an acyl group having 1 to 4 carbon atoms, a cyano group, an alkenyl group having 2 to 6 carbon atoms, a hydroxyl group, a nitro group, and an amino group.

In view of the object of the present invention, which is to obtain an excellent S1P3 antagonistic action, it is preferred that R$^1$ be a trifluoromethyl group, an alkyl group having 1 to 6 carbon atoms, a cycloalkyl group having 3 to 6 carbon atoms, an aryl group having 6 to 10 carbon atoms, or a benzyloxy group. More preferably, R$^1$ is a trifluoromethyl group, a benzyloxy group, an n-propyl group, an i-propyl group, a t-butyl group, a cyclopropyl group, or a phenyl group. Still more preferably, R$^1$ is a trifluoromethyl group, a t-butyl group, or a phenyl group. Further, it is preferred that R$^2$ be an alkyl group having 1 to 6 carbon atoms or an alkenyl group having 2 to 6 carbon atoms. More preferably, R$^2$ is a methyl group, an n-propyl group, or an allyl group. To achieve a high level of safety, it is still more preferred that R$^2$ be an n-propyl group. In addition, it is preferred that R$^2$ have the steric configuration illustrated in the general formula (1a). Moreover, it is preferred that X be a methylene group or an oxygen atom, and more preferably an oxygen atom. Still further, it is preferred that Z be a chlorine atom.

Examples of a pharmaceutically acceptable salt in the present invention include an acid addition salt, such as a hydrochloride salt, a hydrobromide salt, an acetate salt, a trifluoroacetate salt, a methanesulfonate salt, a citrate salt, or a tartrate salt, and an alkaline addition salt, such as a sodium salt, a potassium salt, a calcium salt, a magnesium salt, or an aluminum salt.

According to the present invention, among the compounds represented by the general formula (1), a compound in which X is an oxygen atom and Y is a hydrogen atom, specifically, a compound represented by the general formula (1d) (excluding compounds in which R$^1$ is a carboxyl group), can be prepared based on the following synthesis pathway A, for example.

[Formula 8]

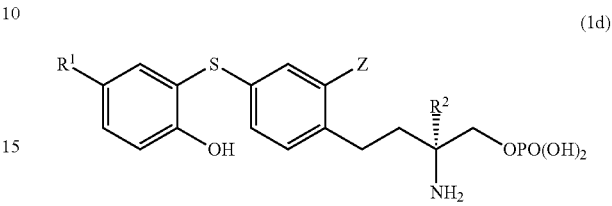

(1d)

(In the formula (1d), R$^1$ represents a hydrogen atom, a halogen atom, a trifluoromethyl group, an optionally substituted alkyl group having 1 to 6 carbon atoms, an optionally substituted cycloalkyl group having 3 to 6 carbon atoms, an optionally substituted aryl group having 6 to 10 carbon atoms, an optionally substituted alkoxy group having 1 to 4 carbon atoms, an optionally substituted benzyloxy group, an optionally substituted acyl group having 1 to 4 carbon atoms, a cyano group, or a carboxyl group; R$^2$ represents an optionally substituted alkyl group having 1 to 6 carbon atoms or an optionally substituted alkenyl group having 2 to 6 carbon atoms; and Z represents a halogen atom.)

<Synthesis Pathway A>

[Formula 9]

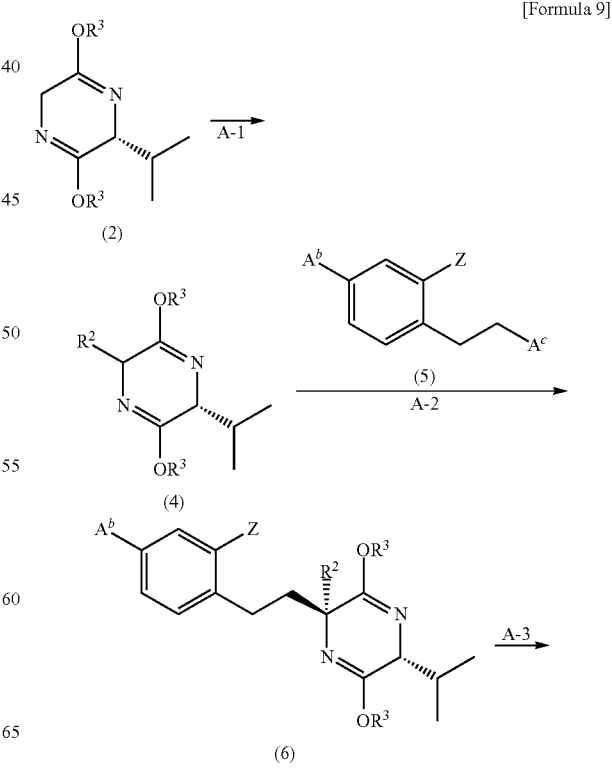

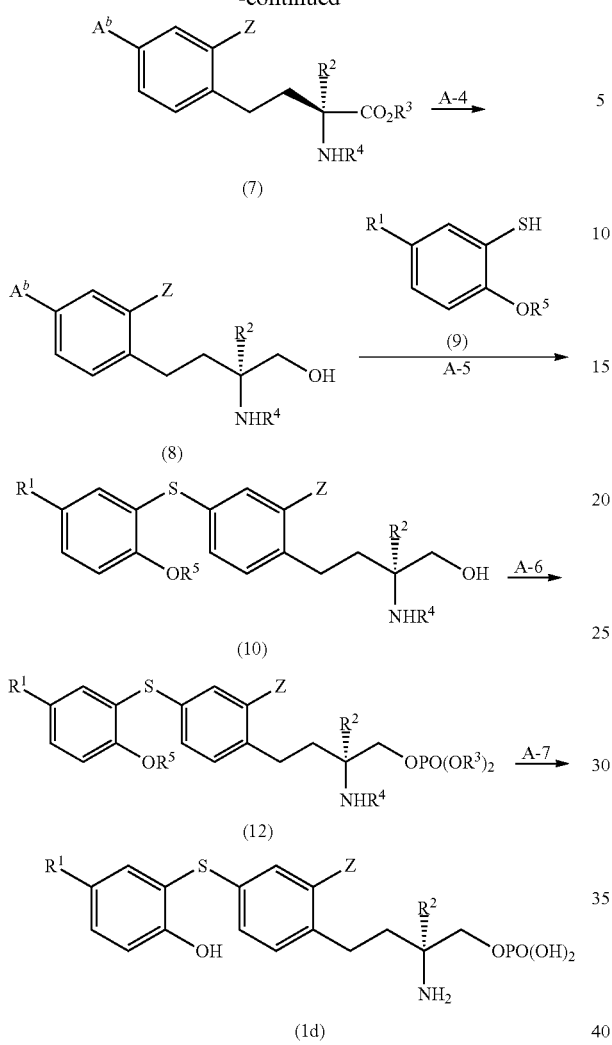

In the synthesis pathway A, an optically active compound represented by the general formula (4),

[Formula 10]

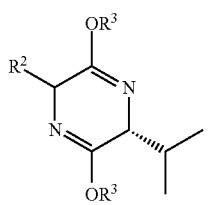

(In the formula (4), $R^3$ represents an optionally substituted alkyl group having 1 to 6 carbon atoms; and $R^2$ is as defined above.), can be prepared by reacting an optically active compound represented by the general formula (2),

[Formula 11]

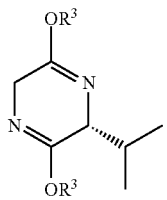

(In the formula (2), $R^3$ is as defined above.), with a compound represented by the general formula (3),

[Formula 12]

$$R^2\text{-}A^a \quad (3)$$

(In the formula (3), $A^a$ represents a typical leaving group such as a halogen atom, a methanesulfonyloxy group, a para-toluenesulfonyloxy group, or a trifluoromethanesulfonyloxy group; and $R^2$ is as defined above.), in the presence of a base (Step A-1).

Specifically, first, in a reaction solvent such as 1,4-dioxane, tetrahydrofuran, or diethyl ether, the compound represented by the general formula (2) is treated at −78° C. using a base. Then, a compound represented by the general formula (3) is reacted at −78° C. on the obtained anion of the compound represented by the general formula (2). Next, the temperature is gradually increased to normal temperature to obtain a compound represented by the general formula (4). Examples of the base that can be used in this reaction include n-butyllithium and lithium diisopropylamide, and n-butyllithium is preferred.

In the present specification, the tent "normal temperature" means 15 to 25° C. as defined in the Japanese Pharmacopoeia.

In the synthesis pathway A, an optically active compound represented by the general formula (6),

[Formula 13]

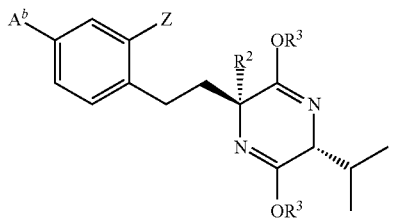

(In the formula (6), $A^b$ represents a typical leaving group such as a halogen atom, a methanesulfonyloxy group, a para-toluenesulfonyloxy group, or a trifluoromethanesulfonyloxy group; and $R^2$, $R^3$, and Z are as defined above.), can be prepared by reacting the optically active compound represented by the general formula (4) with a compound represented by the general formula (5),

[Formula 14]

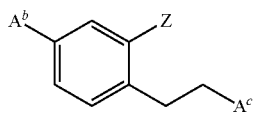

(5)

(In the formula (5), $A^c$ represents a typical leaving group such as a halogen atom, a methanesulfonyloxy group, a para-toluenesulfonyloxy group, or a trifluoromethanesulfonyloxy group; and $A^b$ and Z are as defined above.), in the presence of a base (Step A-2).

Specifically, first, in a reaction solvent such as 1,4-dioxane, tetrahydrofuran, or diethyl ether, the compound represented by the general formula (4) is treated at −78° C. using a base. Then, the compound represented by the general formula (5) is reacted at −78° C. on the obtained anion of the compound represented by the general formula (4). Next, the temperature is gradually increased to normal temperature to obtain the compound represented by the general formula (6). Examples of the base that can be used in this reaction include n-butyllithium and lithium diisopropylamide, and n-butyllithium is preferred.

In the synthesis pathway A, a compound represented by the general formula (7), can be prepared by subjecting the compound represented by the general formula (6) to acid hydrolysis, and then protecting the amino group with a typical protecting reagent.

[Formula 15]

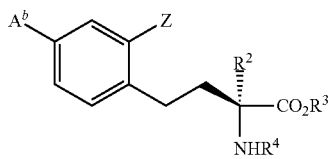

(7)

(In the formula (7), $R^4$ represents a general protecting group for amino group; and $A^b$, $R^2$, $R^3$, and Z are as defined above.), The $R^4$ in the formula is not especially limited as long as it protects the amino group. For example, an acyl group, such as an acetyl group, or a carbamate, such as t-butoxycarbonyl or benzyloxycarbonyl, can be used (Step A-3).

Specifically, first, in an inorganic or organic acid, or in a mixed solvent of an inorganic or organic acid and an organic solvent, the compound represented by the general formula (6) is subjected to acid hydrolysis at normal temperature. Here, as the inorganic acid, hydrochloric acid, hydrobromic acid or the like can be used. As the organic acid, trifluoromethanesulfonic acid or the like can be used. Further, as the organic solvent, methanol, ethanol, tetrahydrofuran, 1,4-dioxane, ethyl acetate or the like can be used. Among these, it is preferred to carry out the acid hydrolysis using a hydrochloric acid in 1,4-dioxane.

Next, after neutralization with a base to obtain an amino ester, this amino ester and an acyl chloride or an acid anhydride are reacted at 0° C. to normal temperature in a solvent to obtain the compound represented by the general formula (7). Examples of the solvent that can be used in this step include ethyl acetate, tetrahydrofuran, N,N-dimethylformamide, 1,4-dioxane, methylene chloride, chloroform, methanol, ethanol, and acetonitrile. As the acyl chloride, acetyl chloride, benzyloxycarbonyl chloride or the like can be used. As the acid anhydride, acetic anhydride, di-t-butyldicarbonate or the like can be used. Among these, it is preferred to carry out the reaction using di-t-butyldicarbonate.

In the synthesis pathway A, a compound represented by the general formula (8) can be prepared by reducing the compound represented by the general formula (7) (Step A-4).

[Formula 16]

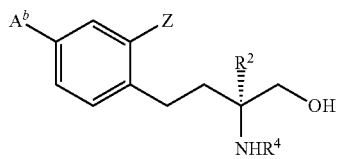

(8)

(In the formula (8), $A^b$, $R^2$, $R^4$, and Z are as defined above.)

For example, in a reaction solvent such as tetrahydrofuran, 1,4-dioxane, ethanol, methanol or the like, the compound represented by the general formula (7) is prepared by reduction using a reductant at 0° C. to the reflux temperature, and preferably at normal temperature. Examples of the reductant that can be used include borane, alkyl borane derivatives such as 9-borabicyclo[3.3.1]nonane (9-BBN), metal hydride complexes such as diisobutylaluminum hydride ($(iBu)_2AlH$), sodium borohydride ($NaBH_4$), lithium borohydride ($LiBH_4$), lithium aluminum hydride ($LiAlH_4$) or the like. Preferably, the reductant is lithium borohydride.

In the synthesis pathway A, a compound represented by the general formula (10) (excluding compounds in which $R^1$ is a carboxyl group),

[Formula 17]

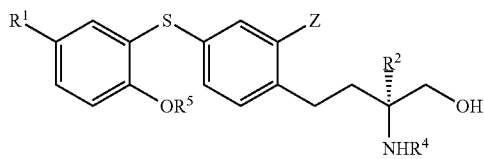

(10)

(In the formula (10), $R^5$ represents a hydrogen atom or a general protecting group for a phenolic hydroxyl group; and $R^1$, $R^2$, $R^4$, and Z are as defined above.), can be prepared by reacting the compound represented by the general formula (8) and the compound represented by the general formula (9) (excluding compounds in which $R^1$ is a carboxyl group).

[Formula 18]

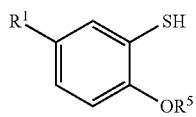

(9)

(In the formula (9), $R^1$ and $R^5$ are as defined above.)

The general protecting group for a phenolic hydroxyl group is not especially limited as long as it protects a phenolic hydroxyl group. For example, a methyl group, a benzyl group, a methoxymethyl group, a tetrahydropyranyl group, a t-butyldimethylsilyl group, an acetyl group, or a t-butoxycarbonyl group can be used (Step A-5).

For example, this reaction can be carried out in a reaction solvent, such as toluene, N,N-dimethylformamide, 1,4-dioxane, tetrahydrofuran, or diethyl ether, in the presence of an inorganic or organic base using a catalyst at normal temperature to the reflux temperature. Examples of inorganic bases that can be used include sodium carbonate or potassium t-butoxide. Examples of organic bases that can be used include diisopropyethylamine. Further, examples of the catalyst that can be used include palladium compounds, such as tris(dibenzylideneacetone) dipalladium(0) or palladium(II) acetate. Preferably, tris(dibenzylideneacetone) dipalladium(0) is used.

A phosphine compound, such as 4,5-bis(diphenylphosphino)-9,9-dimethylxanthene, bis[2-(diphenylphosphino)phenyl]ether, or 1,1'-bis(di-t-butyl phosphino)ferrocene, may be added to the reaction solvent as a reaction accelerator.

In the synthesis pathway A, a compound represented by the general formula (12) (excluding compounds in which $R^1$ is a carboxyl group),

[Formula 19]

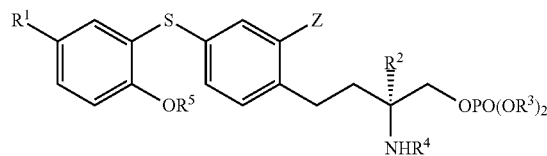

(12)

(In the formula (12), $R^1$, $R^2$, $R^3$, $R^4$, $R^5$, and Z are as defined above.)
can be prepared by reacting the compound represented by the general formula (10) (excluding compounds in which $R^1$ is a carboxyl group) and a compound represented by the general formula (11) (Step A-6).

[Formula 20]

$P(OR^3)_3$ (11)

(In the formula (11), $R^3$ is as defined above.)

For example, this reaction can be carried out in the presence of carbon tetrabromide and pyridine, using no solvent or a solvent such as methylene chloride, chloroform, acetonitrile, ethyl acetate, tetrahydrofuran, or diethyl ether, at 0° C. to normal temperature.

In the synthesis pathway A, a compound represented by the general formula (1d) (excluding compounds in which $R^1$ is a carboxyl group) can be prepared by subjecting the compound represented by the general formula (12) (excluding compounds in which $R^1$ is a carboxyl group) to acid hydrolysis or treatment with a nucleophilic reagent, such as trimethylsilyl bromide or trimethylsilyl iodide (Step A-7).

For the acid hydrolysis reaction, acid hydrolysis can be carried out in an inorganic acid such as hydrochloric acid or hydrobromic acid, or in a mixed solvent of an organic solvent such as methanol or ethanol and an inorganic acid, at the reflux temperature. Further, a treatment using a nucleophilic reagent can be carried out by reacting trimethylsilyl bromide or trimethylsilyl iodide at 0° C. to normal temperature using acetonitrile or methylene chloride as a preferred reaction solvent. Alternatively, the treatment with a nucleophilic reagent can also be carried out by reacting trimethylsilyl chloride and sodium bromide or trimethylsilyl chloride and sodium iodide together.

In the synthesis pathway A, the compound represented by the general formula (7) can also be prepared based on the following synthesis pathway B, for example.

<Synthesis Pathway B>

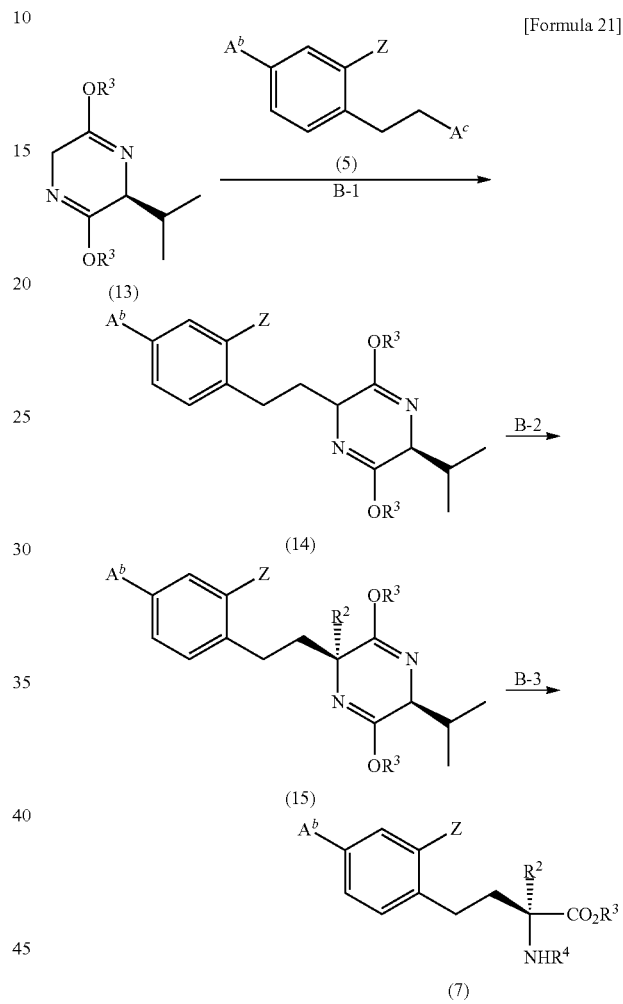

In the synthesis pathway B, an optically active compound represented by the general formula (14),

[Formula 22]

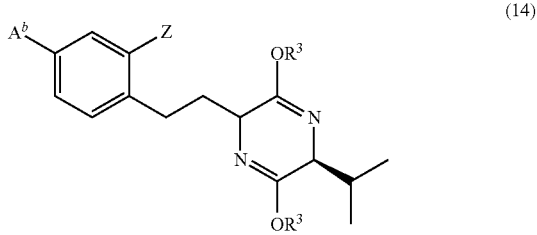

(14)

(In the formula (14), $A^b$, $R^3$, and Z are as defined above.),
can be prepared based on the same method as in Step A-2 using an optically active compound represented by the general formula (13), and the compound represented by the general formula (5) (Step B-1).

[Formula 23]

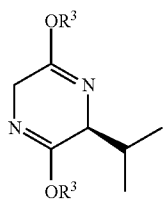

(13)

(In the formula (13), $R^3$ is as defined above.)

In the synthesis pathway B, an optically active compound represented by the general formula (15),

[Formula 24]

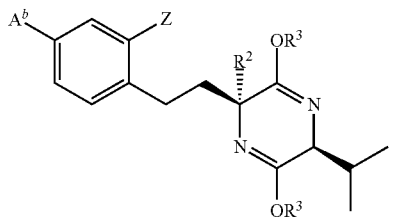

(15)

(In the formula (15), $A^b$, $R^2$, $R^3$, and Z are as defined above.), can be prepared based on the same method as in Step A-1 using the optically active compound represented by the general formula (14) and the compound represented by the general formula (3) (Step B-2).

In the synthesis pathway B, the compound represented by the general formula (7) can be prepared based on the same method as in Step A-3 using the compound represented by the general formula (15) (Step B-3).

In the synthesis pathway A, the compound represented by the general formula (10) (excluding compounds in which $R^1$ is a carboxyl group) can be prepared based on the following synthesis pathway C, for example.

<Synthesis Pathway C>

[Formula 25]

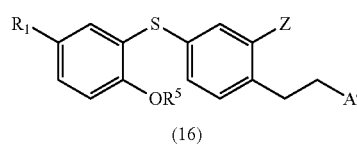

(16)

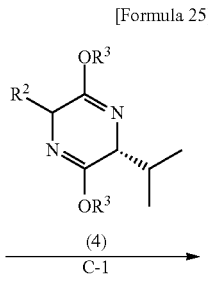

(4) C-1 →

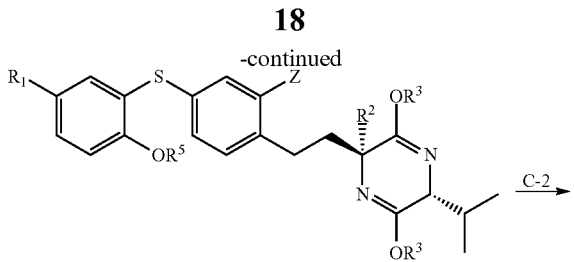

(5)

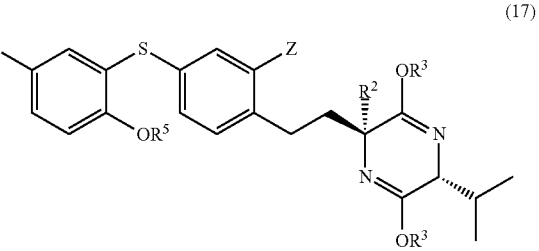

(18)

In the synthesis pathway C, an optically active compound represented by the general formula (17) (excluding compounds in which $R^1$ is a carboxyl group),

[Formula 26]

(17)

(In the formula (17), $R^1$, $R^2$, $R^3$, $R^5$, and Z are as defined above.), can be prepared based on the same method as in Step A-2 using the optically active compound represented by the general formula (4) and a compound represented by the general formula (16) (excluding compounds in which $R^1$ is a carboxyl group) (Step C-1).

[Formula 27]

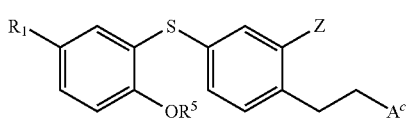

(16)

(In the formula (16), $R^1$, $R^5$, $A^c$, and Z are as defined above.)

In the synthesis pathway C, a compound represented by the general formula (18) (excluding compounds in which $R^1$ is a carboxyl group), can be prepared based on the same method as in Step A-3 using the compound represented by the general formula (17) (excluding compounds in which $R^1$ is a carboxyl group) (Step C-2).

[Formula 28]

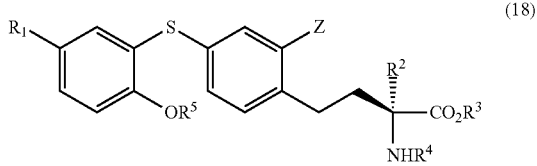

(18)

(In the formula (18), $R^1$, $R^2$, $R^3$, $R^4$, $R^5$, and Z are as defined above.)

In the synthesis pathway C, the compound represented by the general formula (10) (excluding compounds in which $R^1$ is a carboxyl group) can be prepared based on the same method as in Step A-4 using the compound represented by the general formula (18) (excluding compounds in which $R^1$ is a carboxyl group) (Step C-3).

In the synthesis pathway C, the compound represented by the general formula (18) (excluding compounds in which $R^1$ is a carboxyl group) can be prepared based on the following synthesis pathway D, for example.

<Synthesis Pathway D>

[Formula 29]

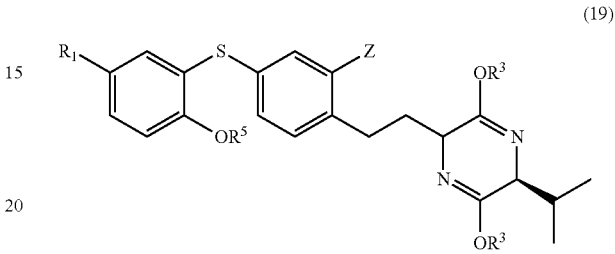

In the synthesis pathway D, an optically active compound represented by the general formula (19) (excluding compounds in which $R^1$ is a carboxyl group), can be prepared based on the same method as in Step A-2 using the optically active compound represented by the general formula (13) and the compound represented by the general formula (16) (excluding compounds in which $R^1$ is a carboxyl group) (Step D-1).

[Formula 30]

(19)

(In the formula (19), $R^1$, $R^3$, $R^5$, and Z are as defined above.)

In the synthesis pathway D, an optically active compound represented by the general formula (20) (excluding compounds in which $R^1$ is a carboxyl group), can be prepared based on the same method as in Step A-1 using the optically active compound represented by the general formula (19) (excluding compounds in which $R^1$ is a carboxyl group) and the compound represented by the general formula (3) (Step D-2).

[Formula 31]

(20)

(In the formula (20), $R^1$, $R^2$, $R^3$, $R^5$, and Z are as defined above.)

In the synthesis pathway D, the compound represented by the general formula (18) (excluding compounds in which $R^1$ is a carboxyl group) can be prepared based on the same method as in Step A-3 using the compound represented by the general formula (20) (excluding compounds in which $R^1$ is a carboxyl group) (Step D-3).

In the synthesis pathway A, among the compounds represented by the general formula (10), a compound in which $R^1$ is a cyano group or an acetyl group and $R^5$ is a general protecting group for phenol, specifically, a compound represented by the general formula (10a), can be prepared by the following synthesis pathway E, for example.

[Formula 32]

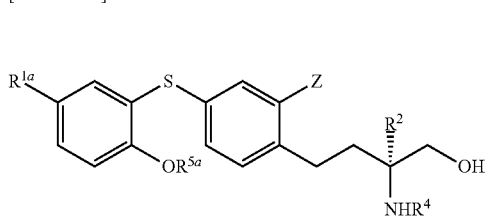
(10a)

(In the formula (10a), $R^{1a}$ represents an acetyl group or a cyano group and $R^{5a}$ represents a general protecting group for a phenolic hydroxyl group; and $R^2$, $R^4$, and Z are as defined above.)

$R^{5a}$ is not especially limited, as long as it protects a phenolic hydroxyl group. For example, a methyl group, a benzyl group, a methoxymethyl group, a tetrahydropyranyl group, a t-butyldimethylsilyl group, an acetyl group, or a t-butoxycarbonyl group can be used.

<Synthesis Pathway E>

[Formula 33]

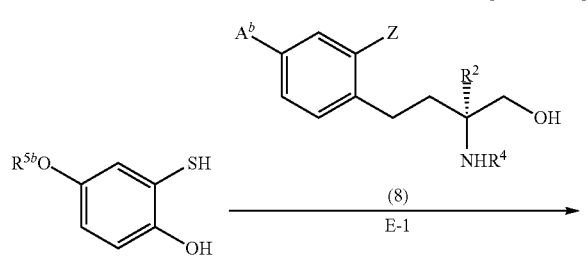
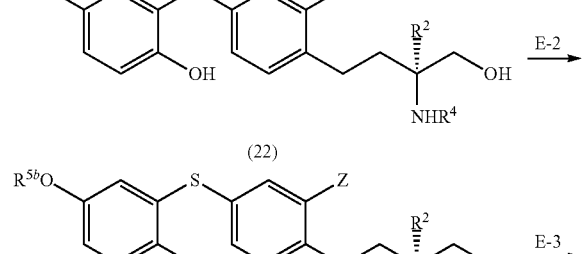
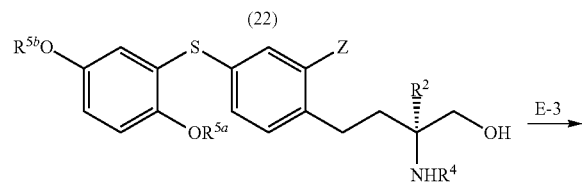
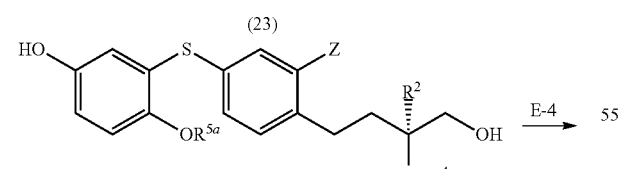
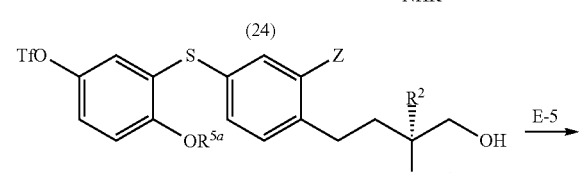

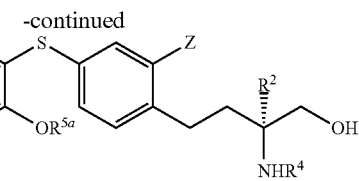
(10a)

In the synthesis pathway E, an optically active compound represented by the general formula (22),

[Formula 34]

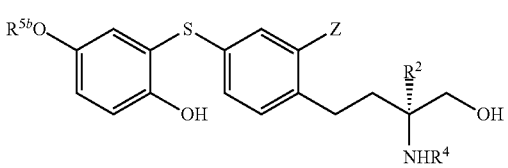
(22)

(In the formula (22), $R^{5b}$ represents a general protecting group for a phenolic hydroxyl group; and $R^2$, $R^4$, and Z are as defined above.), can be prepared based on the same method as in Step A-5 using the optically active compound represented by the general formula (8) and a compound represented by the general formula (21).

[Formula 35]

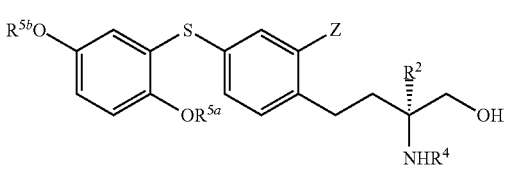
(21)

(In the formula (21), $R^{5b}$ is as defined above.)

$R^{5b}$ is not especially limited, as long as it protects a phenolic hydroxyl group. For example, a methyl group, a benzyl group, a methoxymethyl group, a tetrahydropyranyl group, a t-butyldimethylsilyl group, an acetyl group, or a t-butoxycarbonyl group can be used (Step E-1).

In the synthesis pathway E, a compound represented by the general formula (23), can be prepared by protecting the phenolic hydroxyl group of the compound represented by the general formula (22) (Step E-2).

[Formula 36]

(23)

(In the formula (23), $R^2$, $R^4$, $R^{5a}$, $R^{5b}$, and Z are as defined above.)

This reaction can be carried out by any technique that is commonly used to protect a phenolic hydroxyl group. For example, the reaction can be carried out in a solvent such as acetonitrile, tetrahydrofuran, N,N-dimethylformamide, methylene chloride, or chloroform, in the presence of an inorganic or organic base, by reacting a compound represented by the general formula (22) with a chloride or an acyl chloride. As the inorganic base, potassium carbonate and the like can be used. As the organic base, triethylamine, diisopropylethylamine or the like can be used. Further, examples of the chloride that can be used include methoxymethyl chloride, t-butyldimethylsilyl chloride, and benzyl chloride. Examples of the acyl chloride that can be used include acetyl chloride. Among these, it is preferred to protect the phenolic hydroxyl group using methoxymethyl chloride. In addition, the reaction can be carried out by reacting at 0° C. to normal temperature.

In the synthesis pathway E, a compound represented by the general formula (24), can be prepared by removing the $R^{5b}$ in the compound represented by the general formula (23) (Step E-3).

[Formula 37]

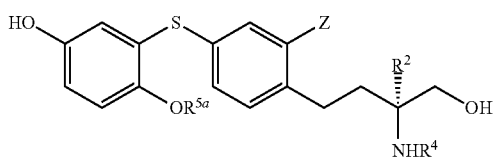

(24)

(In the formula (24), $R^2$, $R^4$, $R^{5a}$, and Z are as defined above.)

The reaction is not especially limited, as long as the technique is commonly used to remove a protecting group for a phenolic hydroxyl group, and $R^{5a}$ is not removed. An example will be described in which $R^{5b}$ is a silyl protecting group, such as a t-butyldimethylsilyl group. In this case, the deprotection reaction can be carried out in a reaction solvent such as tetrahydrofuran, acetonitrile, or methylene chloride using a fluorine compound, such as tetrabutylammonium fluoride or hydrogen fluoride-pyridine, and preferably tetrabutylammonium fluoride. This deprotection reaction can be carried out at from 0° C. to the reflux temperature, and preferably at 0° C.

In the synthesis pathway E, a compound represented by the general formula (25), can be prepared by reacting the compound represented by the general formula (24) with N-phenyltrifluoromethanesulfonimide (Step E-4).

[Formula 38]

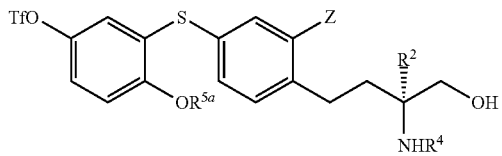

(25)

(In the formula (25), $R^2$, $R^1$, $R^{5a}$, and Z are as defined above.)

For example, this reaction can be carried out by reacting with N-phenyltrifluoromethanesulfonimide in the presence of an organic base such as pyridine, triethylamine or the like using a solvent such as methylene chloride, chloroform, toluene or the like at 0° C. to 80° C., and preferably at normal temperature.

In the synthesis pathway E, a compound represented by the general formula (10a) can be prepared based on a known method using zinc cyanide (e.g., Synth. Commun., 25, 3255-3261 (1995)), or a known method using a Heck reaction (e.g., J. Org., Chem., 55, 3654-3655 (1990)) from a compound represented by the general formula (25) (Step E-5).

An example will be described in which $R^{1a}$ is a cyano group. In this case, the reaction can be carried out in the presence of zinc cyanide, in a reaction solvent such as toluene, N,N-dimethylformamide, 1,4-dioxane, tetrahydrofuran or the like using a catalyst at normal temperature to the reflux temperature. Examples of catalysts that can be used include palladium compounds such as tetrakistriphenylphosphine palladium(0) or tris (dibenzylideneacetone) dipalladium(0), and preferably tetrakistriphenylphosphine palladium(0). Further, a phosphine compound, such as 1,1'-bis(diphenylphosphino)-ferrocene or 1,3-bis(diphenylphosphino)-propane, may be added to the reaction solvent as a reaction accelerator.

Another example will be described in which $R^{1a}$ is an acetyl group. In this case, the reaction can be carried out in the presence of an organic base, using a catalyst and a reaction accelerator, in a solvent such as toluene, N,N-dimethylformamide, 1,4-dioxane, tetrahydrofuran or the like, by reacting with butyl vinyl ether. As the organic base, triethylamine, diisopropylethylamine or the like can be used. Further, as the catalyst, palladium (II) acetate can be used. As the reaction accelerator, 1,3-bis(diphenylphosphino)-propane may be used. The reaction can be carried out at normal temperature to the reflux temperature.

Among the compounds represented by the general formula (1), a compound in which X is —CH$_2$— or —CHF— and Y is a hydrogen atom, specifically, a compound represented by the general formula (1e) (excluding compounds in which $R^1$ is a carboxyl group), can be prepared based on the following synthesis pathway F, for example.

[Formula 39]

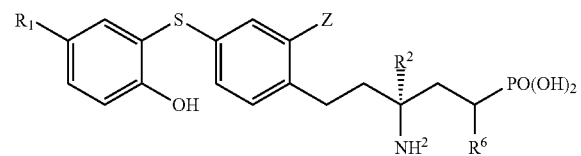

(1e)

(In the formula (1e), $R^6$ represents a hydrogen atom or a fluorine atom; and $R^1$, $R^2$, and Z are as defined above.)

<Synthesis Pathway F>

[Formula 40]

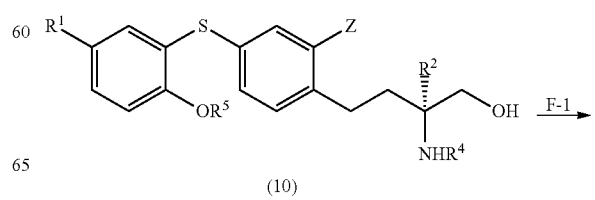

(10)

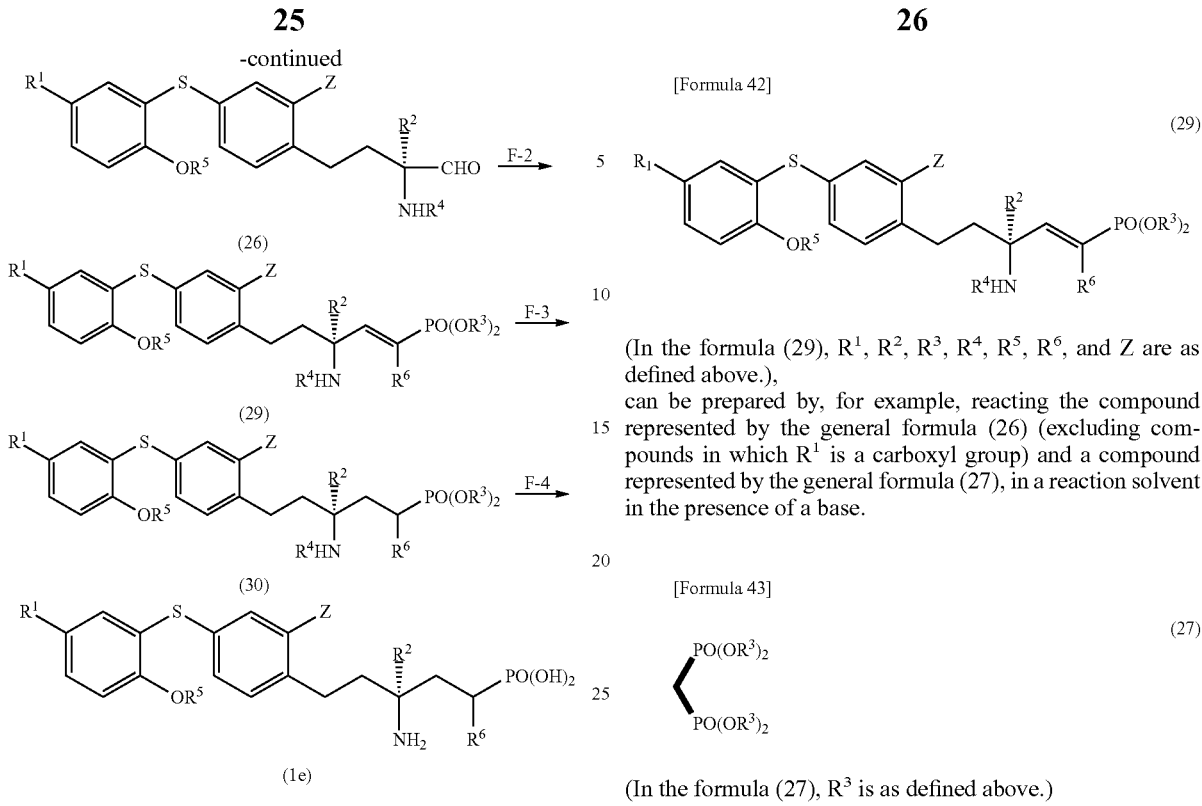

In the synthesis pathway F, a compound represented by the general formula (26) (excluding compounds in which $R^1$ is a carboxyl group), can be prepared by oxidation of the compound represented by the general formula (10) (excluding compounds in which $R^1$ is a carboxyl group) (Step F-1).

[Formula 41]

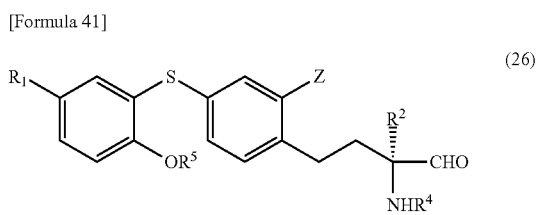

(In the formula (26), $R^1$, $R^2$, $R^4$, $R^5$, and Z are as defined above.)

This reaction can be carried out using a generally used oxidation method to generate aldehyde from alcohol. The oxidation treatment can be carried out using a metal oxidant, such as a chromium oxide-pyridine complex like pyridinium chlorochromate or pyridinium dichromate, chromium oxide, silver carbonate, or manganese dioxide. Alternatively, dimethyl sulfoxide oxidation using various dimethyl sulfoxide activating agents, such as oxalyl chloride, trifluoroacetic anhydride, acetic anhydride, dicyclohexylcarbodiimide, or a sulfur trioxide-pyridine complex, may be used.

In the synthesis pathway F, a compound represented by the general formula (29) (excluding compounds in which $R^1$ is a carboxyl group),

[Formula 42]

(In the formula (29), $R^1$, $R^2$, $R^3$, $R^4$, $R^5$, $R^6$, and Z are as defined above.), can be prepared by, for example, reacting the compound represented by the general formula (26) (excluding compounds in which $R^1$ is a carboxyl group) and a compound represented by the general formula (27), in a reaction solvent in the presence of a base.

[Formula 43]

(In the formula (27), $R^3$ is as defined above.)

Further, the compound represented by the general formula (29) (excluding compounds in which $R^1$ is a carboxyl group) can be prepared by reacting the compound represented by the general formula (26) (excluding compounds in which $R^1$ is a carboxyl group) and a compound represented by the general formula (28), in a reaction solvent in the presence of chlorotrimethylsilane and a base (Step F-2).

[Formula 44]

$$FBr_2CPO(OR^3)_2 \qquad (28)$$

(In the formula (28), $R^3$ is as defined above.)

Examples of the base that can be used in this reaction include sodium hydride, potassium hydride, sodium alkoxide, potassium alkoxide, or n-butyllithium, and preferably n-butyllithium. As the reaction solvent, tetrahydrofuran, diethyl ether, or 1,4-dioxane may be used. Further, the reaction temperature may be set to −78° C. to normal temperature.

In the synthesis pathway F, a compound represented by the general formula (30) (excluding compounds in which $R^1$ is a carboxyl group), can be prepared by reducing a compound represented by the general formula (29) (excluding compounds in which $R^1$ is a carboxyl group) (Step F-3).

[Formula 45]

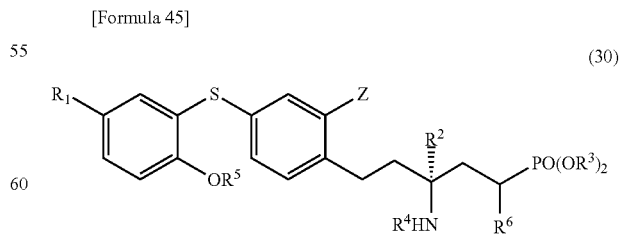

(In the formula (30), $R^1$, $R^2$, $R^3$, $R^1$, $R^5$, $R^6$, and Z are as defined above)

For example, this reaction can be carried out in the presence of a catalyst for catalytic hydrogenation, in a solvent such as ethanol, methanol, tetrahydrofuran, N,N-dimethylformamide, or ethyl acetate, under a normal pressure to increased hydrogen pressure at normal temperature. Examples of catalysts for catalytic hydrogenation that can be used include palladium carbon, platinum carbon, platinum oxide, rhodium carbon, or ruthenium carbon.

In the synthesis pathway F, a compound represented by the general formula (1e) (excluding compounds in which $R^1$ is a carboxyl group) can be prepared based on the same method as in Step A-7 using the compound represented by the general formula (30) (excluding compounds in which $R^1$ is a carboxyl group) (Step F-4).

Among the compounds represented by the general formula (1), a compound in which X is an oxygen atom and Y is an alkyl group having 1 to 6 carbon atoms, specifically, a compound represented by the general formula (1f) (excluding compounds in which $R^1$ is a carboxyl group), can be prepared based on the following synthesis pathway G, for example.

[Formula 46]

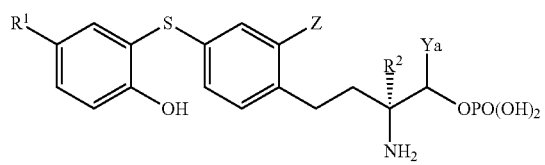

(1f)

(In the formula (1f), Ya represents an optionally substituted alkyl group having 1 to 6 carbon atoms; and $R^1$, $R^2$, and Z are as defined above.)

<Synthesis Pathway G>

[Formula 47]

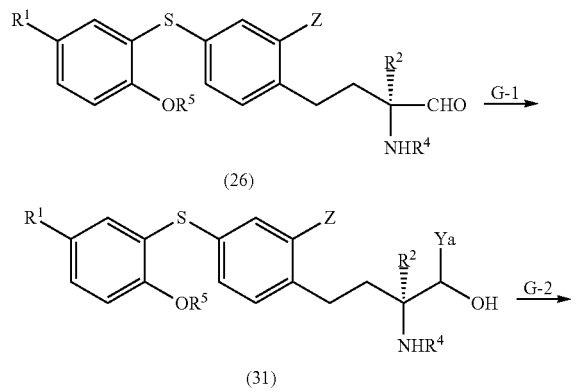

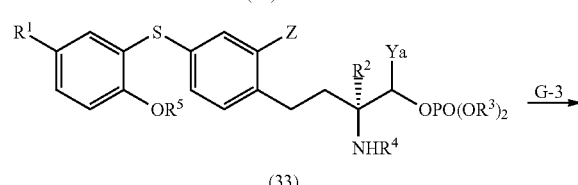

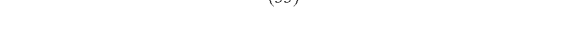

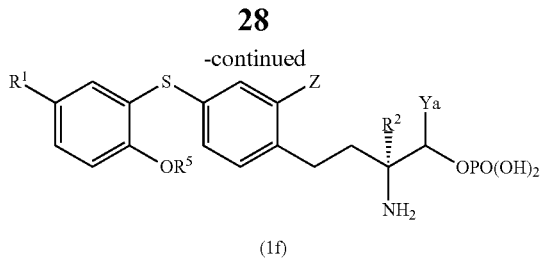

(1f)

In the synthesis pathway G, a compound represented by the general formula (31) (excluding compounds in which $R^1$ is a carboxyl group),

[Formula 48]

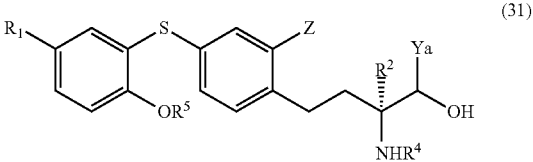

(31)

(In the formula (31), $R^1$, $R^2$, $R^4$, $R^5$, Ya, and Z areas defined above.), can be prepared by reacting the compound represented by the general formula (26) (excluding compounds in which $R^1$ is a carboxyl group) and a compound represented by the general formula (32) (Step G-1).

[Formula 49]

$$Ya-M \quad (32)$$

(In the formula (32), M represents Li, MgCl, MgBr, or MgI; and Ya is as defined above.)

For example, this reaction can be performed at −78° C. to normal temperature using a solvent such as diethyl ether, 1,4-dioxane, tetrahydrofuran or the like.

In the synthesis pathway G, a compound represented by the general formula (33) (excluding compounds in which $R^1$ is a carboxyl group), can be prepared by reacting the compound represented by the general formula (31) (excluding compounds in which $R^1$ is a carboxyl group) and the compound represented by the general formula (11) based on the same method as in Step A-6 (Step G-2).

[Formula 50]

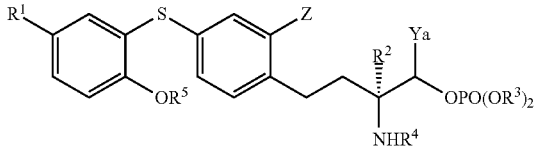

(33)

(In the formula (33), $R^1$, $R^2$, $R^3$, $R^5$, Ya, and Z are as defined above.)

In the synthesis pathway G, the compound represented by the general formula (1f) (excluding compounds in which $R^1$ is a carboxyl group) can be prepared based on the same method as in Step A-7 using the compound represented by the general formula (33) (excluding compounds in which $R^1$ is a carboxyl group) (Step G-3).

Among the compounds represented by the general formula (1), a compound in which X is —CF$_2$— and Y is a hydrogen atom, specifically, a compound represented by the general formula (1g) (excluding compounds in which R$^1$ is a carboxyl group), can be prepared based on the following synthesis pathway H, for example.

[Formula 51]

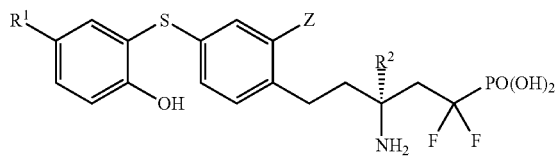

(1g)

(In the formula (1g), R$^1$, R$^2$, and Z are as defined above.)
<Synthesis Pathway H>

[Formula 52]

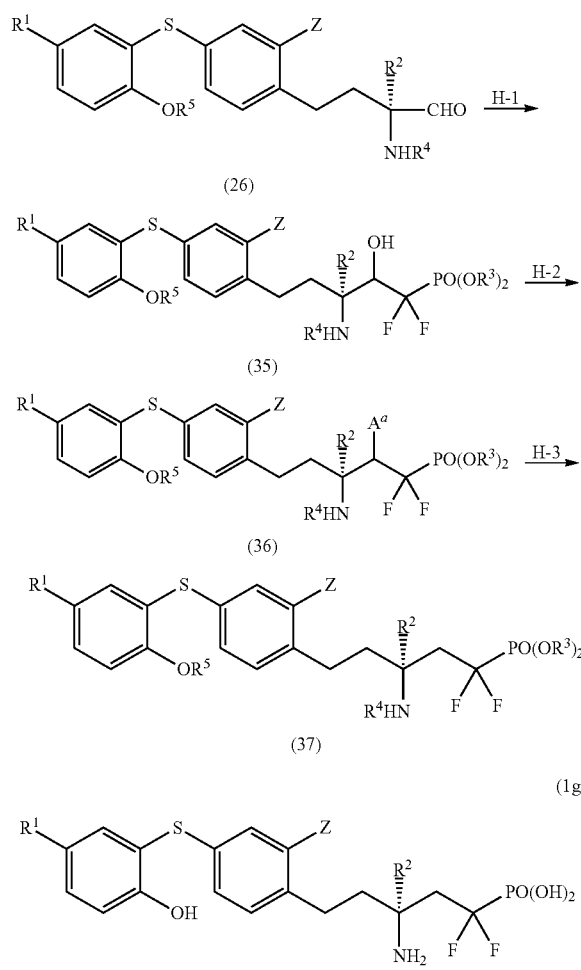

In the synthesis pathway H, a compound represented by the general formula (35) (excluding compounds in which R$^1$ is a carboxyl group),

[Formula 53]

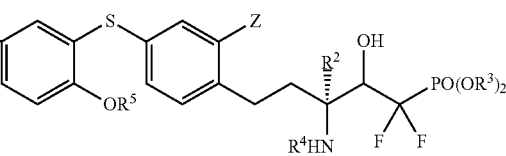

(35)

(In the formula (35), R$^1$, R$^2$, R$^3$, R$^4$, R$^5$, and Z are as defined above.),
can be prepared by reacting the compound represented by the general formula (26) (excluding compounds in which R$^1$ is a carboxyl group) and a compound represented by the general formula (34), in the presence of a base (Step H-1).

[Formula 54]

$$HF_2CPO(OR^3)_2 \qquad (34)$$

(In the formula (34), R$^3$ is as defined above)

Specifically, first, in a reaction solvent such as 1,4-dioxane, tetrahydrofuran, diethyl ether or the like, the compound represented by the general formula (34) is treated at −78° C. using a base. Then, the compound represented by the general formula (26) is reacted at −78° C. with the obtained anion of the compound represented by the general formula (34) to obtain the compound represented by the general formula (35). Examples of the base that can be used include n-butyllithium and lithium diisopropylamide, and lithium diisopropylamide is preferred.

In the synthesis pathway H, a compound represented by the general formula (36), can be prepared by halogenating a hydroxyl group on the compound represented by the general formula (35) or converting that hydroxyl group into a typical leaving group such as a methanesulfonyloxy group (Step H-2).

[Formula 55]

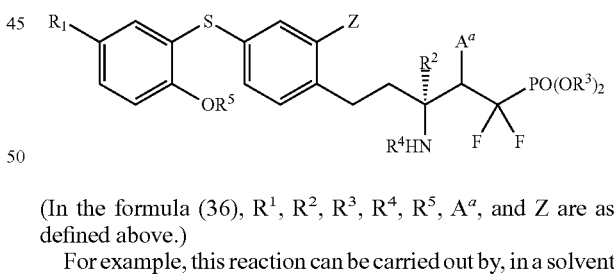

(In the formula (36), R$^1$, R$^2$, R$^3$, R$^4$, R$^5$, A$^a$, and Z are as defined above.)

For example, this reaction can be carried out by, in a solvent such as methylene chloride, chloroform, or toluene, in the presence of an organic base, using a sulfonic acyl chloride or a sulfonic acid anhydride at 0° C. to 80° C., and preferably at normal temperature. As the organic base, pyridine, triethylamine or the like can be used. As the sulfonic acyl chloride, methanesulfonyl chloride or the like can be used. Further, as the sulfonic acid anhydride, methanesulfonic anhydride or the like can be used. In addition, an alkali metal halide such as potassium iodide or sodium iodide may be added to the solvent.

In the synthesis pathway H, a compound represented by the general formula (37) (excluding compounds in which R$^1$ is a carboxyl group), can be prepared by removing the leaving group on the compound represented by the general formula (36) (excluding compounds in which $R^1$ is a carboxyl group) (Step H-3).

[Formula 56]

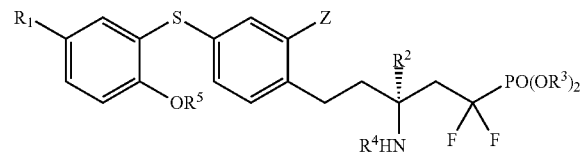

(37)

(In the formula (37), $R^1$, $R^2$, $R^3$, $R^4$, $R^5$, and Z are as defined above.)

For example, this reaction can be carried out in a reaction solvent such as N,N-dimethylformamide, dimethyl sulfide, methylpyrrolidone or the like at 0° C. to the reflux temperature using an alkyl borane derivative or a metal hydride complex. As the alkyl borane derivative, borane or 9-borabicyclo[3.3.1]nonane (9-BBN) can be used. As the metal hydride complex, diisobutylaluminum hydride ((iBu)$_2$AlH), sodium borohydride (NaBH$_4$), lithium borohydride (LiBH$_4$), lithium aluminum hydride (LiAlH$_4$) or the like can be used. Among these, it is preferred to perform this reaction using lithium borohydride.

In the synthesis pathway H, the compound represented by the general formula (1g) (excluding compounds in which $R^1$ is a carboxyl group) can be prepared based on the same method as in Step A-7 using the compound represented by the general formula (37) (excluding compounds in which $R^1$ is a carboxyl group) (Step H-4).

Among the compounds represented by the general formula (1d), a compound in which $R^1$ is a carboxyl group, specifically, a compound represented by the general formula (1h), can be prepared based on the following synthesis pathway I, for example.

[Formula 57]

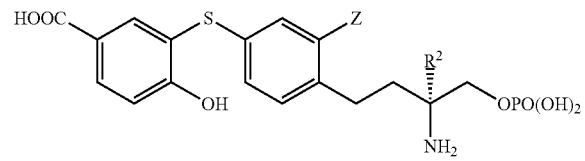

(1h)

(In the formula (1h), $R^2$ and Z are as defined above.)
<Synthesis Pathway I>

[Formula 58]

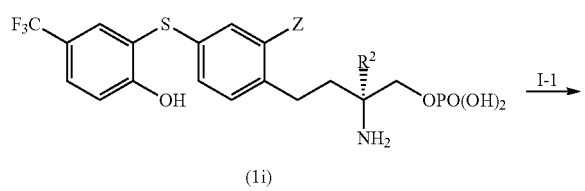

(1i)

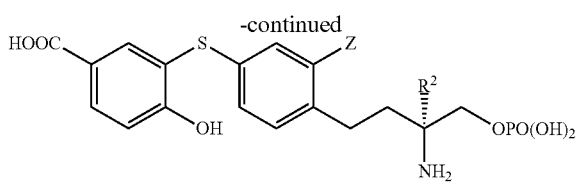

(1h)

In the synthesis pathway I, a compound represented by the general formula (1h),

[Formula 59]

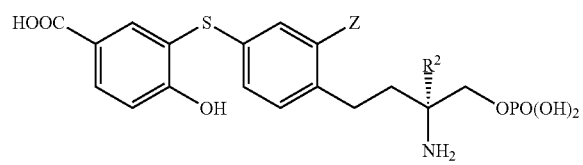

(1h)

(In the formula (1h), $R^2$ and Z are as defined above.), can be prepared by hydrolysis of a compound represented by the general formula (1i), in the presence of a base (Step I-1).

[Formula 60]

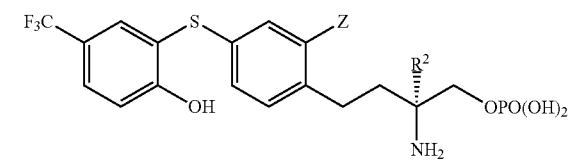

(1i)

(In the formula (1i), $R^2$ and Z are as defined above)

For example, this reaction can be carried out in the presence of a base such as sodium hydroxide or potassium hydroxide in an aqueous solution or an aqueous alcohol solution at room temperature to the reflux temperature. The compound represented by the general formula (1i) can be prepared based on the synthesis pathway A.

Further, the synthesis method of the compound represent by the general formula (16) can be carried out based on the method described in WO 03029184, WO 03029205, WO 04026817, WO 04074297, and WO 050444780 pamphlets.

The diphenyl sulfide derivative according to the present invention, or a pharmaceutically acceptable salt or hydrate thereof, exhibits an excellent S1P3 antagonistic action. Therefore, a medicine having at least one kind or more of such compounds as an active ingredient is effective as a therapeutic or preventive medicine for diseases for which it is known that an S1P3 antagonist is an effective therapeutic or preventive medicine. Examples of diseases for which it is known that an S1P3 antagonist is an effective therapeutic or preventive medicine include sepsis, respiratory tract contraction, bronchial asthma, chronic obstructive pulmonary disease (COPD), pulmonary emphysema, tracheal stenosis, diffuse panbronchiolitis, bronchitis resulting from infection, connective tissue disease, or transplantation, diffuse pulmonary hamartoangiomyomatosis, adult respiratory distress syndrome (ARDS), interstitial pneumonitis, lung cancer, pneumonia hypersensitivity, idiopathic interstitial pneumonia, fibrosis of the lung, and cytokine storm caused by an influenza virus or RS virus infection.

Further, other than the above-described diseases, the medicine according to the present invention is also effective for therapy or prevention for diseases for which it is known that an S1P3 antagonistic action is effective. Examples of diseases for which it is known that an S1P3 antagonistic action is effective include arterial sclerosis, blood vessel intimal hypertrophy, solid tumors, diabetic retinopathy, rheumatoid arthritis, cardiac arrest, ischemia-reperfusion disorders, cerebral blood vessel spasms after subarachnoid bleeding, angina pectoris or myocardial infarction caused by coronary vessel spasms, glomerulonephritis, thrombosis, lung disease caused by pulmonary edema such as ARDS, cardiac arrhythmia, eye disease, eye hypertension, glaucoma, glaucomatous retinopathy, optic neuropathy, and macula-lutea degeneration.

The medicine according to the present invention may be administered orally, or via a non-oral means, for example, intrarectally, subcutaneously, intravenously, intramuscularly, transdermally or the like.

To use as a medicine, the compound according to the present invention, or a pharmaceutically acceptable salt or hydrate thereof, may be in the form of any of a solid composition, a liquid composition, or some other composition. The optimum form is selected as necessary. The medicine composition according to the present invention can be prepared by mixing the compound according to the present invention with a pharmaceutically acceptable carrier. Specifically, the composition according to the present invention can be prepared by ordinary formulation techniques as a tablet, pill, capsule, granule, powder, dispersion, liquid, emulsion, suspension, injection or the like, by adding common diluents, fillers, binders, disintegrants, coatings, sugar coatings, pH adjusting agents, dissolving agents, or aqueous or non-aqueous solvents.

The present invention will now be described based on the following specific examples. However, the present invention is not limited to these examples.

Reference Example 1

(2S,5R)-2-(4-bromo-2-chlorophenyl)ethyl-3,6-dimethoxy-2-methyl-5-isopropyl-2,5-dihydropyrazine

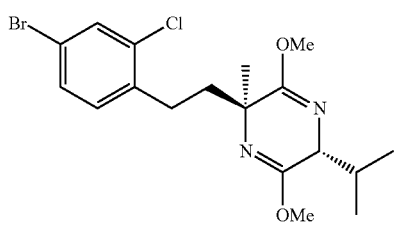

[Formula 61]

Under an argon atmosphere, an n-butyllithium-hexane solution (1.60 mol/L, 25.5 mL) was added at −78° C. into a solution of (5R)-3,6-dimethoxy-2-methyl-5-isopropyl-2,5-dihydropyrazine (7.36 g) in tetrahydrofuran (160 mL) to form a reaction solution. Next, this reaction solution was stirred at −78° C. for 30 minutes. Then, a solution of 4-bromo-2-chloro-1-(3-iodoethyl) benzene (15.34 g) in tetrahydrofuran (26 mL) was added to the reaction solution, and the reaction solution was stirred at −78° C. for 30 minutes and then at 0° C. for 1 hour. Water was added to the reaction solution, and the reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant product was purified by silica gel column chromatography (hexane:ethyl acetate=60:1) to obtain the target product (8.40 g) as a colorless oil.

$^1$H NMR (CDCl$_3$, 400 MHz): δ 0.71 (3H, d, J=6.7 Hz), 1.09 (3H, d, J=6.7 Hz), 1.35 (3H, s), 1.78 (1H, ddd, J=12.8, 11.6, 4.9 Hz), 2.08 (1H, ddd, J=12.8, 11.6, 4.9 Hz), 2.21-2.31 (1H, m), 2.35 (1H, ddd, J=13.4, 11.6, 4.9 Hz), 2.46 (1H, ddd, J=13.4, 11.6, 4.9 Hz), 3.68 (3H, s), 3.69 (3H, s), 4.00 (1H, d, J=3.7 Hz), 7.02 (1H, d, J=7.9 Hz), 7.27 (1H, dd, J=7.9, 1.8 Hz), 7.47 (1H, d, J=1.8 Hz).

ESIMS (+): 415 [M+H]$^+$.

Reference Example 2

(2R,5R)-2-allyl-2-(4-bromo-2-chlorophenyl)ethyl-3,6-dimethoxy-5-isopropyl-2,5-dihydropyrazine

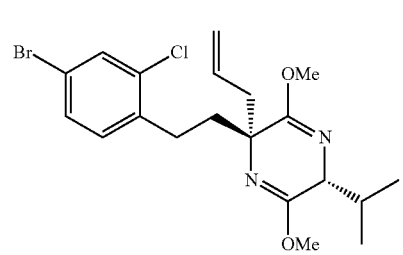

[Formula 62]

The target product (6.04 g) was obtained as a colorless oil by reacting (5R)-2-allyl-3,6-dimethoxy-5-isopropyl-2,5-dihydropyrazine (3.64 g) in the same manner as in Reference Example 1.

H NMR (CDCl$_3$, 400 MHz): δ 0.69 (3H, d, J=6.7 Hz), 1.10 (3H, d, J=6.7 Hz), 1.79 (1H, ddd, J=12.8, 11.6, 4.9 Hz), 2.02 (1H, ddd, J=12.8, 11.6, 4.9 Hz), 2.27-2.48 (4H, m), 2.54 (1H, dd, J=13.4, 7.3 Hz), 3.69 (3H, s), 3.70 (3H, s), 3.95 (1H, d, J=3.1 Hz), 4.97 (1H, dd, 10.4, 2.4 Hz), 5.01 (1H, d, J=17.7 Hz), 5.61-5.72 (1H, m), 7.01 (1H, d, J=7.9 Hz), 7.27 (1H, dd, J=7.9, 1.8 Hz), 7.47 (1H, d, J=1.8 Hz).

ESIMS (+): 441 [M+H]$^+$.

Reference Example 3

Methyl(S)-4-(4-bromo-2-chlorophenyl)-2-t-butoxycarbonylamino-2-methyl butyrate

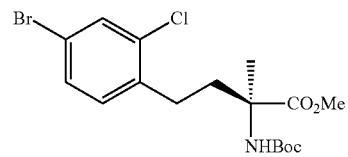

[Formula 63]

0.5 mol/L hydrochloric acid (200 mL) was added to a solution of the compound of Reference Example 1 (8.40 g) in 1,4-dioxane (400 mL) to form a first reaction solution. This first reaction solution was stirred at normal temperature for 1 hour, and then left to stand at normal temperature overnight. Then, the first reaction solution was concentrated, neutralized with a saturated sodium hydrogen carbonate aqueous solution, and extracted with ethyl acetate. The extract was washed with water and saturated brine, and then dried over anhydrous sodium sulfate. After the anhydrous sodium sulfate was removed by filtration, the extract was concentrated, and the resultant residue was dissolved in acetonitrile (16 mL). Di-tert-butoxydicarbonate (11.0 g), was added to this solution to form a second reaction solution. This second reaction solution was stirred at normal temperature for 1 hour and then left to stand at normal temperature overnight. Water was added to the second reaction solution, and the second reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant product was purified by silica gel column chromatography (hexane:ethyl acetate=4:1) to obtain the target product (6.58 g) as a colorless oil.

$^1$H NMR (CDCl$_3$, 400 MHz): δ 1.45 (9H, s), 1.58 (3H, s), 2.09 (1H, ddd, J=13.4, 12.2, 5.5 Hz), 2.39 (1H, br s), 2.51 (1H, td, J=12.8, 4.9 Hz), 2.65 (1H, td, J=12.8, 4.9 Hz), 3.75 (3H, s), 5.42 (1H, br s), 7.04 (1H, d, J=7.9 Hz), 7.30 (1H, dd, J=7.9, 1.8 Hz), 7.48 (1H, d, J=1.8 Hz).

ESIMS (+): 420 [M+H]$^+$.

Reference Example 4

Methyl(R)-2-allyl-4-(4-bromo-2-chlorophenyl)-2-t-butoxycarbonylamino butyrate

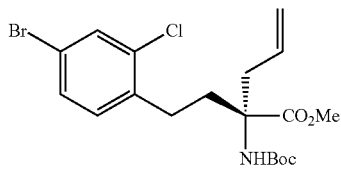

[Formula 64]

A solution of 50% trifluoroacetic acid-water (108 mL) was added to the compound of Reference Example 2 (5.44 g) to form a first reaction solution. This first reaction solution was stirred at normal temperature for 1 hour, and then left to stand at normal temperature overnight. Then, the first reaction solution was neutralized with a saturated sodium hydrogen carbonate aqueous solution, and extracted with ethyl acetate. The extract was washed with water and saturated brine, and then dried over anhydrous sodium sulfate. After the anhydrous sodium sulfate was removed by filtration, the extract was concentrated, and the resultant residue was dissolved in acetonitrile (86 mL). Di-tert-butoxydicarbonate (11.0 g) was added to this solution to form a second reaction solution. This second reaction solution was stirred at normal temperature for 1 hour and then left to stand at normal temperature overnight. Water was added to the second reaction solution, and the second reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant product was purified by silica gel column chromatography (hexane:ethyl acetate=6:1) to obtain the target product (6.16 g) as a colorless oil.

$^1$H NMR (CDCl$_3$, 400 MHz): δ 1.45 (9H, s), 2.08 (1H, ddd, J=13.4, 11.0, 5.5 Hz), 2.39-2.51 (2H, m), 2.51-2.61 (1H, m), 2.67 (1H, td, J=12.8, 4.9 Hz), 3.00-3.14 (1H, m), 3.74 (3H, s), 5.07 (1H, d, J=4.9 Hz), 5.10 (1H, s), 5.52-5.69 (1H, m), 7.03 (1H, d, J=7.9 Hz), 7.29 (1H, dd, J=7.9, 1.8 Hz), 7.48 (1H, d, J=1.8 Hz).

ESIMS (+): 446 [M+H]$^+$.

Reference Example 5

(S)-4-(4-bromo-2-chlorophenyl)-2-t-butoxycarbonylamino-2-methylbutan-1-ol

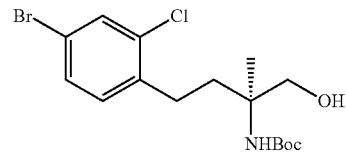

[Formula 65]

Lithium borohydride (259 mg) was added to a solution of the compound of Reference Example 3 (1.00 g) in tetrahydrofuran (24 mL) under ice cooling to form a reaction solution. Next, ethanol (2.4 mL) was added dropwise to the reaction solution, and the reaction solution was then stirred for 2 hours under ice cooling. A 10% citric acid aqueous solution was added to the reaction solution, and the reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant product was purified by silica gel column chromatography (hexane:ethyl acetate=2:1) to obtain the target product (775 mg) as a white solid.

$^1$H NMR (CDCl$_3$, 400 MHz): δ 1.24 (3H, s), 1.44 (9H, s), 1.81 (1H, ddd, J=13.4, 12.2, 5.5 Hz), 2.05 (1H, ddd, J=13.4, 12.2, 5.5 Hz), 2.67 (1H, ddd, J=13.4, 12.2, 5.5 Hz), 2.74 (1H, ddd, J=13.4, 12.2, 5.5 Hz), 3.63-3.74 (2H, m), 4.07 (1H, br s), 4.67 (1H, s), 7.11 (1H, d, J=8.6 Hz), 7.31 (1H, dd, J=8.6, 1.8 Hz), 7.50 (1H, d, J=1.8 Hz).

ESIMS (+): 392 [M+H]$^+$.

Reference Example 6

(R)-2-[2-(4-bromo-2-chlorophenyl)ethyl]-2-t-butoxycarbonylamino-4-penten-1-ol

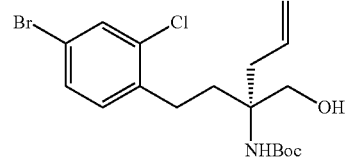

[Formula 66]

The target product (3.20 g) was obtained as a white powder by reacting the compound of Reference Example 4 (6.16 g) in the same manner as in Reference Example 5.

$^1$H NMR (CDCl$_3$, 400 MHz): δ 1.43 (9H, s), 1.80-1.94 (2H, m), 2.32 (1H, td, J=14.1, 7.9 Hz), 2.44 (1H, dd, J=14.1, 6.7 Hz), 2.63-2.77 (2H, m), 3.69-3.79 (2H, m), 4.09 (1H, br s), 4.72 (1H, s), 5.19 (1H, dd, J=6.1, 1.8 Hz), 5.22 (1H, s), 5.80-5.91 (1H, s), 7.11 (1H, d, J=7.9 Hz), 7.31 (1H, dd, J=7.9, 1.8 Hz), 7.49 (1H, d, J=1.8 Hz).

ESIMS (+): 418 [M+H]$^+$.

Reference Example 7

1-(Methoxymethoxy)-4-propylbenzene

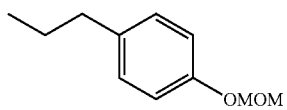

[Formula 67]

Ethyldiisopropylamine (10.3 mL) and chloromethyl methyl ether (4.5 mL) were added to a solution of 4-propylphenol (4.09 g) in methylene chloride (60 mL) under ice cooling to form a reaction solution. This reaction solution was stirred for 15 minutes under ice cooling, and then left overnight at normal temperature. Water was added to the reaction solution, and the reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant product was purified by silica gel column chromatography (hexane:ethyl acetate=9:1) to obtain the target product (4.50 g) as a colorless oil.

$^1$H NMR (CDCl$_3$, 400 MHz): δ 0.93 (3H, t, J=7.3 Hz), 1.55-1.67 (2H, m), 2.53 (2H, t, J=7.3 Hz), 3.48 (3H, s), 5.15 (2H, s), 6.95 (2H, dt, J=8.6, 2.4 Hz), 7.09 (2H, dt, J=8.6, 2.4 Hz).

EIMS (+): 180 [M]$^+$.

Reference Example 8

1-Cyclopropyl-4-(methoxymethoxy)benzene

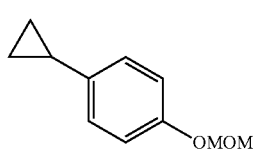

[Formula 68]

The target product (958 mg) was obtained as a colorless oil by reacting 4-cyclopropylphenol (1.00 g) in the same manner as in Reference Example 7.

$^1$H NMR (CDCl$_3$, 400 MHz): δ 0.59-0.62 (2H, m), 0.86-0.93 (2H, m), 1.80-1.90 (1H, m), 3.47 (3H, s), 5.14 (2H, s), 6.94 (2H, dt, J=9.2, 2.4 Hz), 7.01 (2H, dt, J=9.2, 2.4 Hz).

EIMS (+): 178 [M]$^+$.

Reference Example 9

2-(Methoxymethoxy)-5-methylbenzenethiol

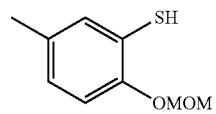

[Formula 69]

Under an argon atmosphere, N,N,N',N'-tetramethylethylenediamine (375 μL) and an n-butyllithium-hexane solution (1.60 mol/L, 1.5 mL) were added under ice cooling to a solution of 1-(methoxymethoxy)-4-methylbenzene (304 mg) in diethyl ether (10 mL) to form a reaction solution. This reaction solution was stirred for 1.5 hours at normal temperature. Then, sulfur (80 mg) was added to the reaction solution under ice cooling, and the reaction solution was stirred for 12 hours. 1 mol/L hydrochloric acid was added to the reaction solution, and the reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant product was purified by silica gel column chromatography (hexane:ethyl acetate=9:1) to obtain the target product (200 mg) as a colorless oil.

$^1$H NMR (CDCl$_3$, 400 MHz): δ 2.24 (3H, s), 3.50 (3H, s), 3.75 (1H, s), 5.21 (2H, s), 6.88 (1H, dd, J=8.6, 1.2 Hz), 6.97 (1H, d, J=8.6 Hz), 7.07 (1H, d, J=1.2 Hz).

EIMS (+): 184 [M]$^+$.

Reference Example 10

5-Ethyl-2-(methoxymethoxy)benzenethiol

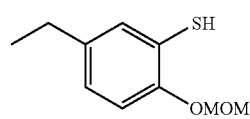

[Formula 70]

The target product (600 mg) was obtained as a colorless oil by reacting 1-ethyl-4-(methoxymethoxy)benzene (665 mg) in the same manner as in Reference Example 9.

$^1$H NMR (CDCl$_3$, 400 MHz): δ 1.19 (3H, t, J=7.9 Hz), 2.54 (2H, q, J=7.9 Hz), 3.51 (3H, s), 3.76 (1H, s), 5.22 (2H, s), 6.91 (1H, dd, J=7.9, 1.8 Hz), 7.00 (1H, d, J=7.9 Hz), 7.09 (1H, d, J=1.8 Hz).

EIMS (+): 198 [M]$^+$.

Reference Example 11

2-(Methoxymethoxy)-5-propylbenzenethiol

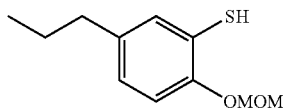

[Formula 71]

The target product (687 mg) was obtained as a colorless oil by reacting the compound of Reference Example 7 (720 mg) in the same manner as in Reference Example 9.

$^1$H NMR (CDCl$_3$, 400 MHz): δ 0.92 (3H, t, J=7.3 Hz), 1.55-1.65 (2H, m), 2.47 (2H, t, J=7.3 Hz), 3.51 (3H, s), 3.76 (1H, s), 5.21 (2H, s), 6.88 (1H, dd, J=8.6, 1.8 Hz), 6.99 (1H, d, J=8.6 Hz), 7.07 (1H, d, J=1.8 Hz).

EIMS (+): 212 [M]$^+$.

Reference Example 12

2-(Methoxymethoxy)-5-isopropylbenzenethiol

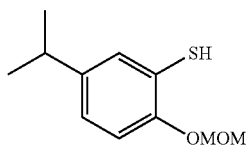

[Formula 72]

The target product (646 mg) was obtained as a colorless oil by reacting 1-(methoxymethoxy)-4-isopropylbenzene (720 mg) in the same manner as in Reference Example 9.

$^1$H NMR (CDCl$_3$, 400 MHz): δ 1.21 (6H, t, J=6.7 Hz), 2.74-2.83 (1H, m), 3.51 (3H, s), 3.78 (1H, s), 5.22 (2H, s), 6.94 (1H, dd, J=8.6, 2.4 Hz), 7.01 (1H, d, J=8.6 Hz), 7.12 (1H, d, J=2.4 Hz).

EIMS (+): 212 [M]$^+$.

Reference Example 13

5-Cyclopropyl-2-(methoxymethoxy)benzenethiol

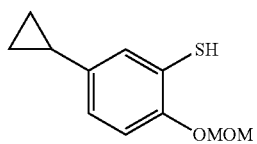

[Formula 73]

The target product (210 mg) was obtained as a colorless oil by reacting the compound of Reference Example 8 (450 mg) in the same manner as in Reference Example 9.

$^1$H NMR (CDCl$_3$, 400 MHz): δ 0.61 (2H, dt, J=6.1, 4.9 Hz), 0.86-0.92 (2H, m), 1.75-1.86 (1H, m), 3.50 (3H, s), 3.76 (1H, s), 5.20 (2H, s), 6.80 (1H, dd, J=8.6, 2.4 Hz), 6.98 (1H, d, J=8.6 Hz), 6.98 (1H, d, J=2.4 Hz).

EIMS (+): 210 [M]$^+$.

Reference Example 14

6-Ethoxy-1,3-benzoxathiol-2-one

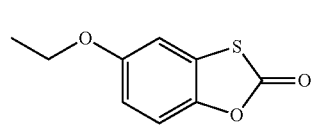

[Formula 74]

Potassium carbonate (533 mg) and ethyl iodide (160 μL) were added to a solution of 6-hydroxy-1,3-benzoxathiol-2-one (336 mg) in N,N-dimethylformamide (10 mL) to form a reaction solution. This reaction solution was stirred for 4 hours at normal temperature. Water was added to the reaction solution. The precipitated crystals were filtrated off, thoroughly washed with water and diisopropyl ether, and then dried under reduced pressure to obtain the target product (245 mg) as a white powder.

$^1$H NMR (CDCl$_3$, 400 MHz): δ 1.42 (3H, t, J=6.7 Hz), 4.02 (2H, q, J=6.7 Hz), 6.84 (1H, dd, J=8.6, 2.4 Hz), 6.91 (1H, d, J=2.4 Hz), 7.18 (1H, d, J=8.6 Hz).

EIMS (+): 196 [M]$^+$.

Reference Example 15

6-Isopropoxy-1,3-benzoxathiol-2-one

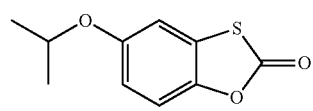

[Formula 75]

Potassium carbonate (829 mg) and isopropyl iodide (300 μL) were added to a solution of 6-hydroxy-1,3-benzoxathiol-2-one (504 mg) in N,N-dimethylformamide (15 mL) to form a reaction solution. This reaction solution was stirred for 4 hours at normal temperature, and then for 8 hours at 40° C. Water was added to the reaction solution, and the reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant product was purified by silica gel column chromatography (hexane:ethyl acetate=4:1) to obtain the target product (300 mg) as a colorless oil.

$^1$H NMR (CDCl$_3$, 400 MHz): δ 1.33 (6H, d, J=6.1 Hz), 4.44-4.53 (1H, m), 6.83 (1H, dd, J=9.2, 2.4 Hz), 6.91 (1H, d, J=2.4 Hz), 7.17 (1H, d, J=9.2 Hz).

EIMS (+): 210 [M]$^+$.

Reference Example 16

5-Ethoxy-2-hydroxybenzenethiol

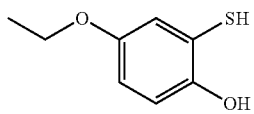
[Formula 76]

Under an argon atmosphere, lithium aluminum hydride (119 mg) was added under ice cooling to a solution of the compound of Reference Example 14 (245 mg) in tetrahydrofuran (12.5 mL) to form a reaction solution. This reaction solution was stirred for 30 minutes under ice cooling. Then, 1 mol/L hydrochloric acid was added to the reaction solution, and the reaction solution was extracted with ethyl acetate. The extract was washed with water and saturated brine in that order, and then dried over anhydrous sodium sulfate. The anhydrous sodium sulfate was removed by filtration, and the solvent was removed by distillation under reduced pressure to obtain the target product (210 mg) as a colorless oil.

$^1$H NMR (CDCl$_3$, 400 MHz): δ 1.38 (3H, t, J=7.3 Hz), 3.10 (1H, s), 3.96 (2H, q, J=7.3 Hz), 5.73 (1H, s), 6.78 (1H, dd, J=9.2, 3.1 Hz), 6.87 (1H, d, J=9.2 Hz), 6.98 (1H, d, J=3.1 Hz).
EIMS (+): 170 [M]$^+$.

Reference Example 17

2-Hydroxy-5-isopropoxybenzenethiol

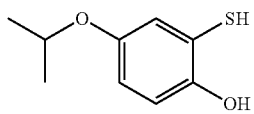
[Formula 77]

The target product (120 mg) was obtained as a colorless oil by reacting the compound of Reference Example 15 (300 mg) in the same manner as in Reference Example 16.

$^1$H NMR (CDCl$_3$, 400 MHz): δ 1.29 (6H, d, J=6.1 Hz), 3.09 (1H, s), 4.33-4.43 (1H, m), 5.74 (1H, s), 6.78 (1H, dd, J=9.2, 3.1 Hz), 6.86 (1H, d, J=9.2 Hz), 7.00 (1H, d, J=3.1 Hz).
EIMS (+): 184 [M]$^+$.

Reference Example 18

(2-Methoxy-5-trifluoromethylphenylthio)ethoxymethane-1-thione

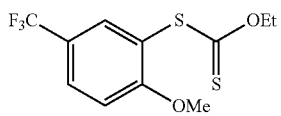
[Formula 78]

Under an argon atmosphere, water (13 mL) and concentrated hydrochloric acid (6.9 mL) were added under ice cooling to a solution of 2-methoxy-5-trifluoromethylaniline (2.50 g) in methanol (13 mL) to form a first reaction solution. This first reaction solution was stirred under ice cooling for 10 minutes, and sodium nitrite (1.26 g) was added thereto and then the first reaction solution was stirred under ice cooling for 1 hour. The first reaction solution was slowly added dropwise to an aqueous solution (13 mL) of potassium ethylxanthate (4.19 g) heated at 65° C. to form a second reaction solution. The second reaction solution was stirred at 65° C. for 1 hour. The temperature of this second reaction solution was returned to normal temperature. Then ice water was added to the second reaction solution, and the second reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant product was purified by silica gel column chromatography (hexane:ethyl acetate=20:1) to obtain the target product (913 mg) as a colorless oil.

$^1$H NMR (CDCl$_3$, 400 MHz): δ 1.31 (3H, t, J=7.3 Hz), 3.92 (3H, s), 4.60 (2H, q, J=7.3 Hz), 7.04 (1H, d, J=8.6 Hz), 7.71 (1H, dd, J=8.6, 2.4 Hz), 7.73 (1H, d, J=2.4 Hz).
EIMS (+): 296 [M]$^+$.

Reference Example 19

2-Methoxy-5-trifluoromethylbenzenethiol

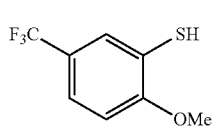
[Formula 79]

The target product (400 mg) was obtained as a colorless oil by reacting the compound of Reference Example 18 (600 mg) in the same manner as in Reference Example 16.

$^1$H NMR (CDCl$_3$, 400 MHz): δ 3.93 (1H, s), 3.95 (3H, s), 6.90 (1H, d, J=8.6 Hz), 7.38 (1H, dd, J=8.6, 2.4 Hz), 7.51 (1H, d, J=2.4 Hz).
EIMS (+): 296 [M]$^+$.

Reference Example 20

(S)-2-t-butoxycarbonylamino-4-[2-chloro-4-(2-methoxymethoxy-5-methylphenylthio)phenyl]-2-methylbutan-1-ol

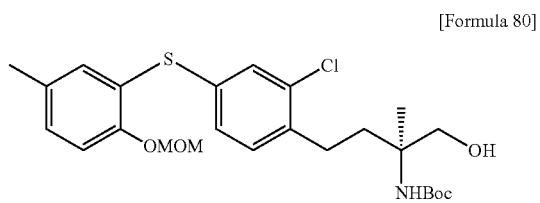
[Formula 80]

Under an argon atmosphere, 4,5-bis(diphenylphosphino)-9,9-dimethylxanthene (52 mg) was added to a solution of a tris(dibenzylideneacetone) dipalladium(0)-chloroform adduct (47 mg) in 1,4-dioxane (1 mL) to form a reaction solution. This reaction solution was heated to reflux for 15 minutes. To the reaction solution, a solution of the compound of Reference Example 5 (178 mg) in 1,4-dioxane (0.7 mL), ethyldiisopropylamine (148 μL), and a solution of the compound of Reference Example 9 (100 mg) in 1,4-dioxane (0.6 mL) were added in this order, and the reaction solution was heated to reflux for 3 hours. Water was added to the reaction solution, and the reaction solution was extracted with ethyl acetate. The extract was washed with water and saturated brine in that order, and then dried over anhydrous sodium sulfate. The solvent was removed by distillation under reduced pressure, and the resultant product was purified by silica gel column chromatography (hexane:ethyl acetate=4:1) to obtain the target product (188 mg) as a colorless oil.

$^1$H NMR (CDCl$_3$, 400 MHz): δ 1.24 (3H, s), 1.44 (9H, s), 1.80 (1H, ddd, J=13.4, 12.2, 5.5 Hz), 2.05 (1H, ddd, J=13.4, 12.2, 5.5 Hz), 2.25 (3H, s), 2.67 (1H, td, J=12.8, 5.5 Hz), 2.74 (1H, td, J=12.8, 5.5 Hz), 3.40 (3H, s), 3.62-3.74 (2H, m), 4.09 (1H, br s), 4.68 (1H, s), 5.16 (2H, s), 7.02-7.07 (3H, m), 7.11 (1H, dd, J=7.9, 1.8 Hz), 7.14 (1H, d, J=7.9 Hz), 7.26 (1H, d, J=1.8 Hz).

ESIMS (+): 496 [M+H]$^+$.

Reference Example 21

(S)-2-t-butoxycarbonylamino-4-[2-chloro-4-(5-ethyl-2-methoxymethoxyphenylthio)phenyl]-2-methylbutan-1-ol

[Formula 81]

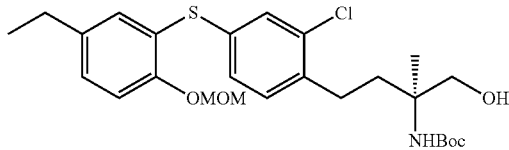

The target product (205 mg) was obtained as a colorless oil by reacting the compound of Reference Example 10 (100 mg) and the compound of Reference Example 5 (165 mg) in the same manner as in Reference Example 20.

$^1$H NMR (CDCl$_3$, 400 MHz): δ 1.17 (3H, t, J=7.3 Hz), 1.24 (3H, s), 1.44 (9H, s), 1.79 (1H, ddd, J=13.4, 12.2, 5.5 Hz), 2.04 (1H, ddd, J=13.4, 12.2, 5.5 Hz), 2.55 (2H, q, J=7.3 Hz), 2.67 (1H, td, J=12.8, 4.9 Hz), 2.74 (1H, td, J=12.8, 4.9 Hz), 3.40 (3H, s), 3.62-3.75 (2H, m), 4.09 (1H, br s), 4.68 (1H, s), 5.17 (2H, s), 7.06-7.12 (4H, m), 7.14 (1H, d, J=7.9 Hz), 7.25 (1H, d, J=1.8 Hz).

ESIMS (+): 510 [M+H]$^+$.

Reference Example 22

(S)-2-t-butoxycarbonylamino-4-[2-chloro-4-(2-methoxymethoxy-5-propylphenylthio)phenyl]-2-methylbutan-1-ol

[Formula 82]

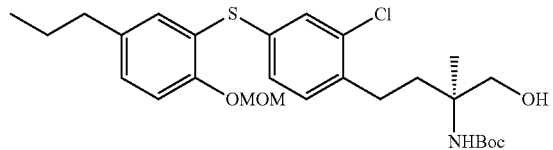

The target product (152 mg) was obtained as a colorless oil by reacting the compound of Reference Example 11 (110 mg) and the compound of Reference Example 5 (170 mg) in the same manner as in Reference Example 20.

$^1$H NMR (CDCl$_3$, 400 MHz): δ 0.90 (3H, t, J=7.3 Hz), 1.24 (3H, s), 1.44 (9H, s), 1.51-1.61 (2H, m), 1.79 (1H, ddd, J=13.6, 12.2, 5.5 Hz), 2.04 (1H, ddd, J=13.6, 12.2, 5.5 Hz), 2.48 (2H, q, J=7.3 Hz), 2.67 (1H, td, J=12.8, 4.9 Hz), 2.74 (1H, td, J=12.8, 4.9 Hz), 3.40 (3H, s), 3.63-3.74 (2H, m), 4.09 (1H, br s), 4.67 (1H, s), 5.16 (2H, s), 7.08 (3H, s), 7.10 (1H, d, J=1.8 Hz), 7.13 (1H, d, J=7.9 Hz), 7.24 (1H, d, J=1.8 Hz).

ESIMS (+): 524 [M+H]$^+$.

Reference Example 23

(S)-2-t-butoxycarbonylamino-4-[2-chloro-4-(2-methoxymethoxy-5-isopropylphenylthio)phenyl]-2-methylbutan-1-ol

[Formula 83]

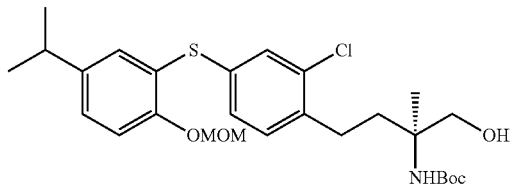

The target product (264 mg) was obtained as a colorless oil by reacting the compound of Reference Example 12 (139 mg) and the compound of Reference Example 5 (200 mg) in the same manner as in Reference Example 20.

$^1$H NMR (CDCl$_3$, 400 MHz): δ 1.19 (6H, t, J=6.7 Hz), 1.24 (3H, s), 1.44 (9H, s), 1.79 (1H, ddd, J=13.4, 12.2, 5.5 Hz), 2.03 (1H, ddd, J=13.4, 12.2, 5.5 Hz), 2.67 (1H, td, J=12.8, 4.9 Hz), 2.74 (1H, td, J=12.8, 4.9 Hz), 2.78-2.87 (1H, m), 3.39 (3H, s), 3.63-3.74 (2H, m), 4.08 (1H, br s), 4.67 (1H, s), 5.16 (2H, s), 7.06-7.16 (5H, m), 7.24 (1H, d, J=1.8 Hz).

ESIMS (+): 524 [M+H]$^+$.

Reference Example 24

(S)-2-t-butoxycarbonylamino-4-[2-chloro-4-(5-cyclopropyl-2-methoxymethoxy-phenylthio)phenyl]-2-methylbutan-1-ol

[Formula 84]

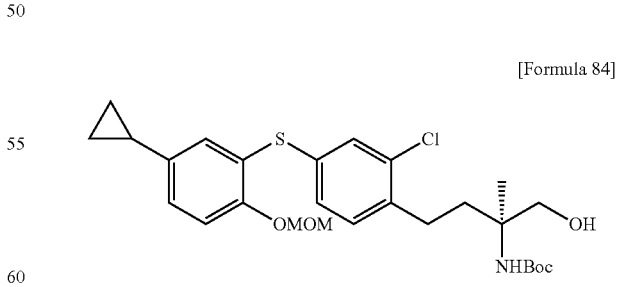

The target product (262 mg) was obtained as a colorless oil by reacting the compound of Reference Example 13 (129 mg) and the compound of Reference Example 5 (200 mg) in the same manner as in Reference Example 20.

$^1$H NMR (CDCl$_3$, 400 MHz): δ 0.58 (2H, dt, J=6.1, 4.9 Hz), 0.86-0.92 (2H, m), 1.24 (3H, s), 1.44 (9H, s), 1.74-1.85

(2H, m), 1.98-2.08 (1H, m), 2.67 (1H, td, J=12.8, 4.9 Hz), 2.74 (1H, td, J=12.8, 4.9 Hz), 3.38 (3H, s), 3.63-3.74 (2H, m), 4.06 (1H, br s), 4.67 (1H, s), 5.15 (2H, s), 6.96 (1H, dd, J=7.9, 1.8 Hz), 7.00 (1H, d, J=1.8 Hz), 7.05 (1H, d, J=7.9 Hz), 7.09 (1H, dd, J=7.9, 1.8 Hz), 7.13 (1H, d, J=7.9 Hz), 7.24 (1H, d, J=1.8 Hz).

ESIMS (+): 522 [M+H]$^+$.

Reference Example 25

(S)-2-t-butoxycarbonylamino-4-[2-chloro-4-(2-hydroxy-5-methoxyphenylthio)phenyl]-2-methylbutan-1-ol

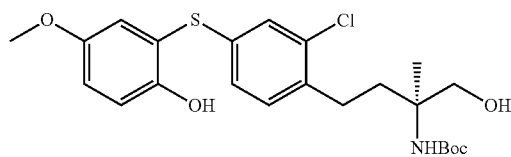

[Formula 85]

The target product (233 mg) was obtained as a colorless oil by reacting 2-hydroxy-5-methoxybenzenethiol (100 mg) and the compound of Reference Example 5 (209 mg) in the same manner as in Reference Example 20.

$^1$H NMR (CDCl$_3$, 400 MHz): δ 1.23 (3H, s), 1.43 (9H, s), 1.78 (1H, ddd, J=13.4, 12.2, 4.9 Hz), 2.00 (1H, ddd, J=13.4, 12.2, 4.9 Hz), 2.59-2.76 (2H, m), 3.61-3.73 (2H, m), 3.77 (3H, s), 4.06 (1H, br s), 4.65 (1H, s), 6.03 (1H, s), 6.91 (1H, dd, J=7.9, 1.8 Hz), 6.97 (1H, dd, J=7.9, 3.1 Hz), 7.01 (1H, d, J=7.9 Hz), 7.02 (1H, d, J=3.1 Hz), 7.06 (1H, d, J=1.8 Hz), 7.11 (1H, d, J=7.9 Hz).

ESIMS (+): 468 [M+H]$^+$.

Reference Example 26

(S)-2-t-butoxycarbonylamino-4-[2-chloro-4-(5-ethoxy-2-hydroxyphenylthio)phenyl]-2-methylbutan-1-ol

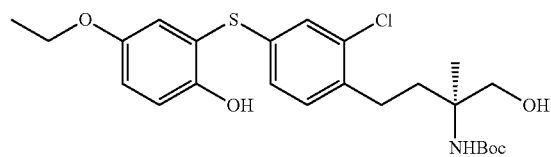

[Formula 86]

The target product (204 mg) was obtained as a colorless oil by reacting the compound of Reference Example 16 (104 mg) and the compound of Reference Example 5 (200 mg) in the same manner as in Reference Example 20.

$^1$H NMR (CDCl$_3$, 400 MHz): δ 1.22 (3H, s), 1.39 (3H, t, J=7.3 Hz). 1.43 (9H, s), 1.77 (1H, ddd, J=13.4, 12.2, 4.9 Hz), 2.00 (1H, ddd, J=13.4, 12.2, 4.9 Hz), 2.64 (1H, td, J=12.8, 4.9 Hz), 2.71 (1H, td, J=12.8, 4.9 Hz), 3.65 (1H, dd, J=11.6, 4.9 Hz), 3.60 (1H, dd, J=11.6, 7.3 Hz), 3.97 (2H, q, J=7.3 Hz), 4.10 (1H, br s), 4.66 (1H, s), 6.03 (1H, s), 6.91 (1H, dd, J=7.9, 1.8 Hz), 6.96 (1H, dd, J=8.6, 2.4 Hz), 7.00 (1H, d, J=8.6 Hz), 7.02 (1H, d, J=2.4 Hz), 7.06 (1H, d, J=1.8 Hz), 7.10 (1H, d, J=7.9 Hz).

ESIMS (+): 482 [M+H]$^+$.

Reference Example 27

(S)-2-t-butoxycarbonylamino-4-[2-chloro-4-(2-hydroxy-5-isopropoxyphenylthio)phenyl]-2-methylbutan-1-ol

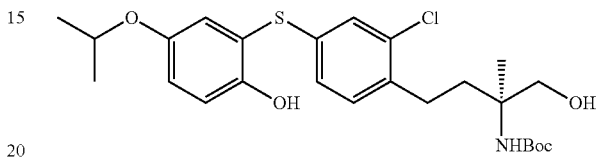

[Formula 87]

The target product (252 mg) was obtained as a colorless oil by reacting the compound of Reference Example 17 (113 mg) and the compound of Reference Example 5 (200 mg) in the same manner as in Reference Example 20.

$^1$H NMR (CDCl$_3$, 400 MHz): δ 1.22 (3H, s), 1.30 (6H, d, J=6.1 Hz), 1.43 (9H, s), 1.77 (1H, ddd, J=13.4, 11.6, 5.5 Hz), 2.00 (1H, ddd, J=13.4, 11.6, 5.5 Hz), 2.59-2.75 (2H, m), 3.61-3.73 (2H, m), 4.07 (1H, br s), 4.35-4.46 (1H, m), 4.65 (1H, s), 6.04 (1H, s), 6.91 (1H, dd, J=7.9, 2.4 Hz), 6.95 (1H, dd, J=8.6, 2.4 Hz), 6.99 (1H, d, J=8.6 Hz), 7.04 (1H, d, J=2.4 Hz), 7.06 (1H, d, J=1.8 Hz), 7.10 (1H, d, J=7.9 Hz).

ESIMS (+): 496 [M+H]$^+$.

Reference Example 28

(S)-2-t-butoxycarbonylamino-4-[4-(5-benzyloxy-2-hydroxyphenylthio)-2-chlorophenyl]-2-methylbutan-1-ol

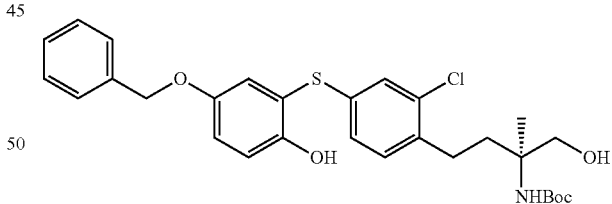

[Formula 88]

The target product (132 mg) was obtained as a colorless oil by reacting 5-benzyloxy-2-hydroxybenzenethiol (142 mg, Z. J. Song et al., Proc Natl Acad Sci USA, 101 (16), 5776 (2004)) and the compound of Reference Example 5 (200 mg) in the same manner as in Reference Example 20.

$^1$H NMR (CDCl$_3$, 400 MHz): δ 1.23 (3H, s), 1.43 (9H, s), 1.78 (1H, ddd, J=13.4, 12.2, 4.9 Hz), 2.01 (1H, ddd, J=13.4, 12.2, 4.9 Hz), 2.59-2.78 (2H, m), 3.62-3.74 (2H, m), 4.04 (1H, br s), 4.65 (1H, s), 5.01 (2H, s), 6.04 (1H, s), 6.90 (1H, dd, J=7.9, 1.8 Hz), 7.00 (1H, dd, J=7.9, 2.4 Hz), 7.04 (1H, dd, J=7.9, 2.4 Hz), 7.06 (1H, d, J=2.4 Hz), 7.10 (1H, d, J=7.9 Hz), 7.11 (1H, d, J=2.4 Hz), 7.30-7.45 (5H, m).

ESIMS (+): 544 [M+H]$^+$.

Reference Example 29

(S)-2-t-butoxycarbonylamino-4-[2-chloro-4-(5-chloro-2-methoxyphenylthio)phenyl]-2-methylbutan-1-ol

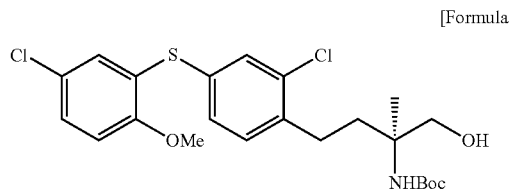

[Formula 89]

The target product was obtained as a colorless oil by reacting the compound of Reference Example 5 (200 mg) and the compound described in Example 1(1) of WO 05018529 pamphlet (5-chloro-2-methoxybenzenethiol, 107 mg) in the same manner as in Reference Example 20.

$^1$H NMR (CDCl$_3$, 400 MHz): δ 1.26 (3H, s), 1.45 (9H, s), 1.83 (1H, ddd, J=13.4, 11.6, 5.5 Hz), 2.08 (1H, ddd, J=13.4, 11.6, 5.5 Hz), 2.71 (1H, td, J=12.8, 4.9 Hz), 2.78 (1H, td, J=12.8, 4.9 Hz), 3.68 (1H, dd, J=11.6, 5.5 Hz), 3.72 (1H, dd, J=11.6, 7.3 Hz), 3.86 (3H, s), 4.10 (1H, br s), 4.69 (1H, s), 6.04 (1H, s), 6.81 (1H, d, J=9.2 Hz), 6.97 (1H, d, J=2.4 Hz), 7.15-7.24 (3H, m), 7.36 (1H, d, J=1.2 Hz).
ESIMS (+): 486 [M+H]$^+$.

Reference Example 30

(S)-2-t-butoxycarbonylamino-4-[4-(2-t-butoxycarbonyloxy-5-chlorophenylthio)-2-chlorophenyl]-2-methylbutan-1-ol

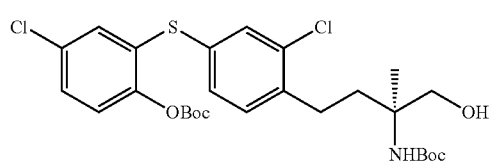

[Formula 90]

Under an argon atmosphere, a boron tribromide-methylene chloride solution (1 mol/L, 1.4 mL) was added under ice cooling to a solution of the compound of Reference Example 29 (228 mg) in methylene chloride (5 mL) to form a first reaction solution. This first reaction solution was stirred under ice cooling for 1 hour. Then, a saturated sodium hydrogen carbonate aqueous solution was added to the first reaction solution, and the first reaction solution was extracted with ethyl acetate. The extract was washed with water and saturated brine in that order, and then dried over anhydrous sodium sulfate. After the anhydrous sodium sulfate was removed by filtration, the solvent was removed by distillation under reduced pressure, and the resultant residue was dissolved in an acetonitrile (5 mL)/methanol (0.2 mL) mixed solvent. Triethylamine (197 μL) and di-tert-butoxydicarbonate (307 mg) were added to the solution to form a second reaction solution. This second reaction solution was stirred at normal temperature for 2 hours and then left to stand overnight. Then, water was added to the second reaction solution, and the second reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant product was purified by silica gel column chromatography (hexane:ethyl acetate=2:1) to obtain the target product (188 mg) as a colorless oil.

$^1$H NMR (CDCl$_3$, 400 MHz): δ 1.25 (3H, s), 1.44 (9H, s), 1.53 (9H, s), 1.82 (1H, ddd, J=13.4, 12.2, 4.9 Hz), 2.07 (1H, ddd, J=13.4, 12.2, 4.9 Hz), 2.70 (1H, td, J=12.8, 4.9 Hz), 2.77 (1H, td, J=12.8, 4.9 Hz), 3.67 (1H, dd, J=11.6, 5.5 Hz), 3.72 (1H, dd, J=11.6, 7.3 Hz), 4.11 (1H, br s), 4.69 (1H, s), 7.11 (1H, d, J=8.6 Hz), 7.14 (1H, d, J=2.4 Hz), 7.21 (2H, d, J=1.2 Hz), 7.23 (1H, dd, J=8.6, 2.4 Hz), 7.39 (1H, d, J=1.2 Hz).
CIMS (+): 572 [M+H]$^+$.

Reference Example 31

(S)-2-t-butoxycarbonylamino-4-[4-(2-t-butoxycarbonyloxy-5-trifluoromethylphenylthio)-2-chlorophenyl]-2-methylbutan-1-ol

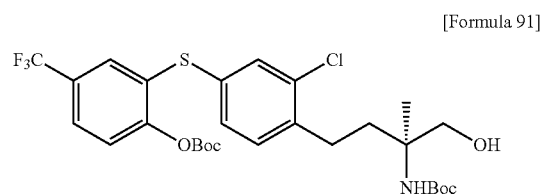

[Formula 91]

A diphenyl sulfide was obtained by reacting the compound of Reference Example 19 (127 mg) and the compound of Reference Example 5 (200 mg) in the same manner as in Reference Example 20. Then, the target product (160 mg) was obtained as a colorless oil by reacting this diphenyl sulfide in the same manner as in Reference Example 30.

$^1$H NMR (CDCl$_3$, 400 MHz): δ 1.25 (3H, s), 1.44 (9H, s), 1.54 (9H, s), 1.83 (1H, ddd, J=14.1, 12.2, 5.5 Hz), 2.07 (1H, ddd, J=14.1, 12.2, 5.5 Hz), 2.65-2.82 (2H, m), 3.67 (1H, dd, J=11.6, 5.5 Hz), 3.72 (1H, dd, J=11.6, 7.3 Hz), 4.06 (1H, br s), 4.68 (1H, s), 7.20 (2H, d, J'=1.8 Hz), 7.31 (1H, d, J=7.9 Hz), 7.40 (1H, d, J=1.8 Hz), 7.46 (1H, d, J=1.8 Hz), 7.54 (1H, dd, J=7.9, 1.8 Hz).
ESIMS (+): 606 [M+H]$^+$.

Reference Example 32

(R)-2-allyl-2-t-butoxycarbonylamino-4-[2-chloro-4-(2-methoxy-5-trifluoromethylphenylthio)phenyl]butan-1-ol

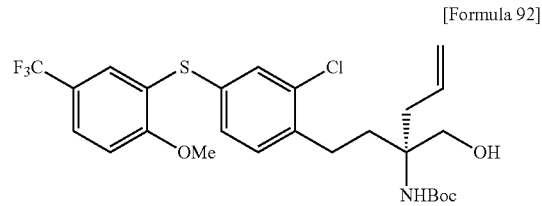 [SMILES: C=CC[C@@](CO)(CCc1ccc(Sc2cc(C(F)(F)F)ccc2O)cc1Cl)NC(=O)OC(C)(C)C]

[Formula 92]

The target product (1.60 g) was obtained as a colorless oil by reacting the compound of Reference Example 19 (750 mg) and the compound of Reference Example 6 (1.26 g) in the same manner as in Reference Example 20.

$^1$H NMR (CDCl$_3$, 400 MHz): δ 1.47 (9H, s), 1.92 (1H, dd, J=6.1, 1.8 Hz), 1.95 (1H, dd, J=6.1, 1.8 Hz), 2.37 (1H, dd, J=14.1, 7.9 Hz), 2.48 (1H, dd, J=14.1, 6.7 Hz), 2.73-2.82 (2H, m), 3.71-3.84 (2H, m), 3.95 (3H, s), 4.12 (1H, br s) 4.76 (1H, s), 5.22 (1H, d, J=2.4 Hz), 5.25 (1H, s), 5.86-5.96 (1H, m), 6.98 (1H, d, J=8.6 Hz), 7.19 (1H, dd, J=7.9, 1.8 Hz), 7.24 (1H, d, J=7.9 Hz), 7.35 (1H, d, J=1.8 Hz), 7.36 (1H, t, J=1.8 Hz), 7.53 (1H, dd, J=8.6, 1.8 Hz).

ESIMS (+): 546 [M+H]$^+$.

Reference Example 33

(R)-2-allyl-2-t-butoxycarbonylamino-4-[2-chloro-4-(2-hydroxy-5-trifluoromethylphenylthio)phenyl]butan-1-ol

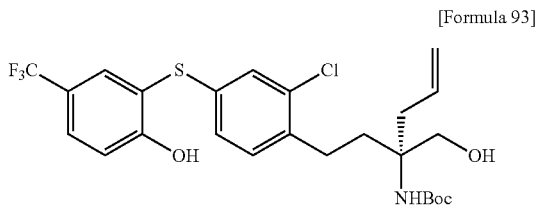

[Formula 93]

Under an argon atmosphere, a boron tribromide-methylene chloride solution (1 mol/L, 8.5 mL) was added under ice cooling to a solution of the compound of Reference Example 32 (1.55 g) in methylene chloride (30 mL) to form a first reaction solution. This first reaction solution was stirred under ice cooling for 1 hour. Then, a saturated sodium hydrogen carbonate aqueous solution was added to the first reaction solution, and the first reaction solution was extracted with ethyl acetate. The extract was washed with water and saturated brine in that order, and then dried over anhydrous sodium sulfate. After the anhydrous sodium sulfate was removed by filtration, the solvent was removed by distillation under reduced pressure, and the resultant residue was dissolved in an acetonitrile (30 mL) solvent. Di-tert-butoxydicarbonate (930 mg) was added to this solution to form a second reaction solution. This second reaction solution was stirred at normal temperature for 2 hours and then left to stand overnight. Then, water was added to the second reaction solution, and the second reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant product was purified by silica gel column chromatography (hexane:ethyl acetate=2:1) to obtain the target product (940 mg) as a colorless oil.

$^1$H NMR (CDCl$_3$, 400 MHz): δ 1.43 (9H, s), 1.82-1.88 (2H, m), 2.31 (1H, dd, J=14.1, 8.6 Hz), 2.43 (1H, dd, J=14.1, 6.7 Hz), 2.69 (2H, dt, J=11.0, 6.7 Hz), 3.67-3.78 (2H, m), 4.07 (1H, br s) 4.71 (1H, s), 5.18 (1H, dd, J=6.1, 1.8 Hz), 5.21 (1H, s), 5.78-5.90 (1H, m), 6.74 (1H, s), 6.91 (1H, dd, J=7.9, 2.4 Hz), 7.08 (1H, d, J=2.4 Hz), 7.15 (2H, t, J=7.9 Hz), 7.63 (1H, dd, J=7.9, 1.8 Hz), 7.80 (1H, d, J=2.4 Hz).

ESIMS (+): 532 [M+H]$^+$.

Reference Example 34

(S)-2-t-butoxycarbonylamino-4-[4-(2-t-butoxycarbonyloxy-5-trifluoromethylphenylthio)-2-chlorophenyl]-2-propylbutan-1-ol

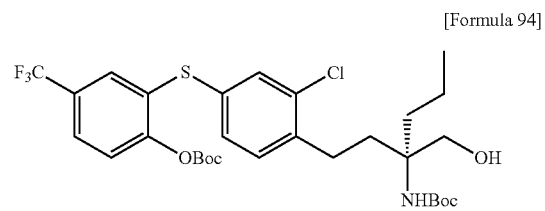

[Formula 94]

A palladium on activated carbon/ethylene diamine complex (100 mg) was added to a solution of the compound of Example 33 (473 mg) in ethyl acetate (9 mL) to form a first reaction solution. This first reaction solution was stirred at normal temperature for 20 hours under hydrogen purging. The first reaction solution was filtrated through Celite, and the solvent was removed by distillation. The resultant residue was dissolved in acetonitrile (9 mL). Triethylamine (145 μL) and di-tert-butoxydicarbonate (284 mg) were added to this solution to form a second reaction solution. This second reaction solution was stirred at normal temperature for 2 hours and then left to stand overnight. Then, water was added to the second reaction solution, and the second reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant product was purified by silica gel column chromatography (hexane:ethyl acetate=2:1) to obtain the target product (434 mg) as a colorless oil.

$^1$H NMR (CDCl$_3$, 400 MHz): δ 0.96 (3H, t, J=7.3 Hz), 1.30-1.42 (2H, m), 1.44 (9H, s), 1.54 (9H, s), 1.54-1.60 (2H, m), 1.83 (1H, ddd, J=13.4, 12.2, 5.5 Hz), 1.94 (1H, ddd, J=13.4, 12.2, 5.5 Hz), 2.62-2.77 (2H, m), 3.74 (2H, d, J=6.1 Hz), 4.10 (1H, br s) 4.62 (1H, s), 7.20 (2H, s), 7.30 (1H, d, J=8.6 Hz), 7.39 (1H, s), 7.47 (1H, d, J=1.8 Hz), 7.53 (1H, dd, J=8.6, 1.8 Hz).

ESIMS (+): 634 [M+H]$^+$.

Reference Example 35

(S)-2-t-butoxycarbonylamino-4-[2-chloro-4-(2-methoxymethoxy-5-methylphenylthio)phenyl]-1-dimethoxyphosphoryloxy-2-methylbutane

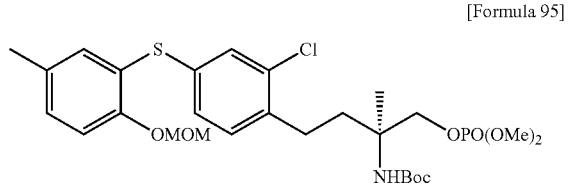

[Formula 95]

Carbon tetrabromide (130 mg) and trimethyl phosphite (46 μL) were added under ice cooling to a solution of the compound of Example 20 (97 mg) in pyridine (0.5 mL) to form a reaction solution. This reaction solution was stirred for 2 hours under ice cooling. Then, water was added to the reaction solution, and the reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant product was purified by silica gel column chromatography (hexane:ethyl acetate=1:1) to obtain the target product (84 mg) as a colorless oil.

$^1$H NMR (CDCl$_3$, 400 MHz): δ 1.35 (3H, s), 1.44 (9H, s), 1.76 (1H, ddd, J=14.1, 12.2, 6.1 Hz), 2.05-2.13 (1H, m), 2.25 (3H, s), 2.62-2.75 (2H, m), 3.40 (3H, s), 3.78 (6H, d, J=11.0 Hz), 4.02 (1H, dd, J=9.8, 5.5 Hz), 4.22 (1H, dd, J=9.8, 5.5 Hz), 4.62 (1H, s), 5.16 (2H, s), 7.02-7.07 (3H, m), 7.11 (2H, d, J=1.8 Hz), 7.25 (1H, d, J=1.8 Hz).

ESIMS (+): 604[M+H]$^+$.

Reference Example 36

(S)-2-t-butoxycarbonylamino-4-[2-chloro-4-(5-ethyl-2-methoxymethoxyphenylthio)phenyl]-1-dimethoxyphosphoryloxy-2-methylbutane

[Formula 96]

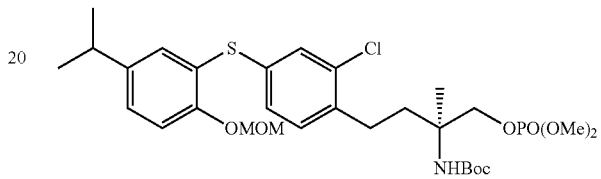

The target product (114 mg) was obtained as a colorless oil by reacting the compound of Reference Example 21 (100 mg) in the same manner as in Reference Example 35.

$^1$H NMR (CDCl$_3$, 400 MHz): δ 1.17 (3H, t, J=7.3 Hz), 1.35 (3H, s), 1.44 (9H, s), 1.75 (1H, ddd, J=13.4, 11.6, 5.5 Hz), 1.98-2.15 (1H, m), 2.55 (2H, q, J=7.3 Hz), 2.61-2.76 (2H, m), 3.39 (3H, s), 3.78 (6H, d, J=11.0 Hz), 4.02 (1H, dd, J=9.8, 5.5 Hz), 4.23 (1H, dd, J=9.8, 5.5 Hz), 4.62 (1H, s), 5.16 (2H, s), 7.05-7.13 (5H, m), 7.24 (1H, d, J=1.2 Hz).

ESIMS (+): 618 [M+H]$^+$.

Reference Example 37

(S)-2-t-butoxycarbonylamino-4-[2-chloro-4-(2-methoxymethoxy-5-propylphenylthio)phenyl]-1-dimethoxyphosphoryloxy-2-methylbutane

[Formula 97]

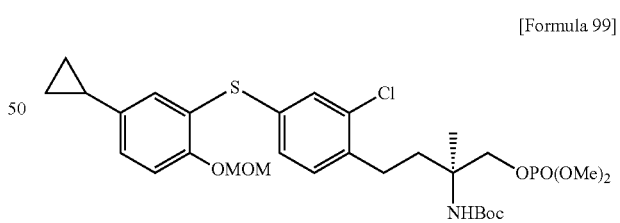

The target product (112 mg) was obtained as a colorless oil by reacting the compound of Reference Example 22 (100 mg) in the same manner as in Reference Example 35.

$^1$H NMR (CDCl$_3$, 400 MHz): δ 0.90 (3H, t, J=7.3 Hz), 1.35 (3H, s), 1.44 (9H, s), 1.51-1.61 (2H, m), 1.75 (1H, ddd, J=13.4, 11.6, 5.5 Hz), 1.97-2.13 (1H, m), 2.48 (2H, t, J=7.3 Hz), 2.61-2.76 (2H, m), 3.39 (3H, s), 3.78 (6H, d, J=11.0 Hz), 4.02 (1H, dd, J=9.8, 5.5 Hz), 4.23 (1H, dd, J=9.8, 5.5 Hz), 4.62 (1H, s), 5.16 (2H, s), 7.05-7.13 (5H, m), 7.24 (1H, d, J=1.2 Hz).

ESIMS (+): 632 [M+H]$^+$.

Reference Example 38

(S)-2-t-butoxycarbonylamino-4-[2-chloro-4-(2-methoxymethoxy-5-isopropylphenylthio)phenyl]-1-dimethoxyphosphoryloxy-2-methylbutane

[Formula 98]

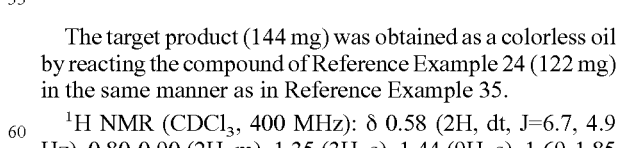

The target product (86 mg) was obtained as a colorless oil by reacting the compound of Reference Example 23 (132 mg) in the same manner as in Reference Example 35.

$^1$H NMR (CDCl$_3$, 400 MHz): δ 1.19 (6H, t, J=7.3 Hz), 1.35 (3H, s), 1.44 (9H, s), 1.75 (1H, ddd, J=13.4, 12.2, 5.5 Hz), 2.00-2.15 (1H, m), 2.61-2.76 (2H, m), 2.76-2.87 (1H, m), 3.39 (3H, s), 3.78 (6H, d, J=11.0 Hz), 4.02 (1H, dd, J=9.8, 5.5 Hz), 4.23 (1H, dd, J=9.8, 5.5 Hz), 4.62 (1H, s), 5.16 (2H, s), 7.05-7.13 (5H, m), 7.23 (1H, d, J=1.8 Hz).

ESIMS (+): 632 [M+H]$^+$.

Reference Example 39

(S)-2-t-butoxycarbonylamino-4-[2-chloro-4-(5-cyclopropyl-2-methoxymethoxyphenylthio)phenyl]-1-dimethoxyphosphoryloxy-2-methylbutane

[Formula 99]

The target product (144 mg) was obtained as a colorless oil by reacting the compound of Reference Example 24 (122 mg) in the same manner as in Reference Example 35.

$^1$H NMR (CDCl$_3$, 400 MHz): δ 0.58 (2H, dt, J=6.7, 4.9 Hz), 0.80-0.90 (2H, m), 1.35 (3H, s), 1.44 (9H, s), 1.69-1.85 (2H, m), 1.96-2.14 (1H, m), 2.61-2.76 (2H, m), 3.38 (3H, s), 3.78 (6H, d, J=11.0 Hz), 4.02 (1H, dd, J=9.8, 5.5 Hz), 4.22 (1H, dd, J=9.8, 5.5 Hz), 4.62 (1H, s), 5.14 (2H, s), 6.96 (1H, dd, J=8.6, 1.8 Hz), 7.00 (1H, d, J=1.8 Hz), 7.03-7.13 (3H, m), 7.23 (1H, d, J=1.8 Hz).

ESIMS (+): 630 [M+H]$^+$.

Reference Example 40

(S)-2-t-butoxycarbonylamino-4-[2-chloro-4-(2-hydroxy-5-methoxy phenylthio)phenyl]-1-dimethoxyphosphoryloxy-2-methylbutane

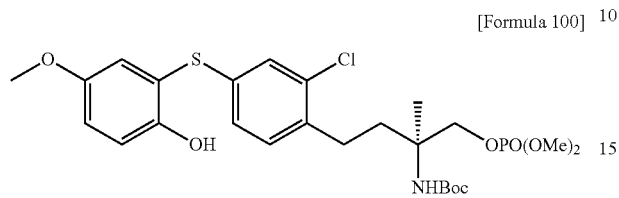

[Formula 100]

The target product (89 mg) was obtained as a colorless oil by reacting the compound of Reference Example 25 (110 mg) in the same manner as in Reference Example 35.

$^1$H NMR (CDCl$_3$, 400 MHz): δ 1.34 (3H, s), 1.43 (9H, s), 1.73 (1H, ddd, J=13.4, 11.6, 5.5 Hz), 1.99-2.09 (1H, m), 2.64 (1H, td, J=13.4, 5.5 Hz), 2.68 (1H, td, J=13.4, 5.5 Hz), 3.77 (3H, s), 3.77 (3H, d, J=11.0 Hz), 3.78 (3H, d, J=11.0 Hz), 4.00 (1H, dd, J=9.8, 4.9 Hz), 4.20 (1H, dd, J=9.8, 4.9 Hz), 4.61 (1H, s), 6.05 (1H, s), 6.91 (1H, dd, J=7.9, 1.8 Hz), 6.97 (1H, dd, J=8.6, 3.1 Hz), 7.01 (1H, d, J=7.9 Hz), 7.02 (1H, d, J=3.1 Hz), 7.06 (1H, d, J=1.8 Hz), 7.08 (1H, d, J=8.6 Hz).

ESIMS (+): 576 [M+H]$^+$.

Reference Example 41

(S)-2-t-butoxycarbonylamino-4-[2-chloro-4-(5-ethoxy-2-hydroxyphenylthio)phenyl]-1-dimethoxyphosphoryloxy-2-methylbutane

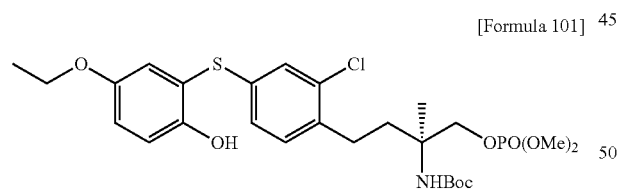

[Formula 101]

The target product (108 mg) was obtained as a colorless oil by reacting the compound of Reference Example 26 (146 mg) in the same manner as in Reference Example 35.

$^1$H NMR (CDCl$_3$, 400 MHz): δ 1.34 (3H, s), 1.39 (3H, t, J=7.3 Hz), 1.43 (9H, s), 1.73 (1H, ddd, J=14.1, 12.2, 5.5 Hz), 1.99-2.09 (1H, m), 2.64 (1H, td, J=13.4, 5.5 Hz), 2.68 (1H, td, J=13.4, 5.5 Hz), 3.77 (3H, d, J=11.0 Hz), 3.78 (3H, d, J=11.0 Hz), 3.97 (2H, q, J=7.3 Hz), 4.00 (1H, dd, J=9.8, 4.9 Hz), 4.20 (1H, dd, J=9.8, 4.9 Hz), 4.61 (1H, s), 6.04 (1H, s), 6.91 (1H, dd, J=7.9, 1.8 Hz), 6.96 (1H, dd, J=8.6, 2.4 Hz), 7.00 (1H, d, J=8.6 Hz), 7.02 (1H, d, J=2.4 Hz), 7.05 (1H, d, J=1.8 Hz), 7.08 (1H, d, J=7.9 Hz).

ESIMS (+): 590 [M+H]$^+$.

Reference Example 42

(S)-2-t-butoxycarbonylamino-4-[2-chloro-4-(2-hydroxy-5-isopropoxyphenylthio)phenyl]-1-dimethoxyphosphoryloxy-2-methylbutane

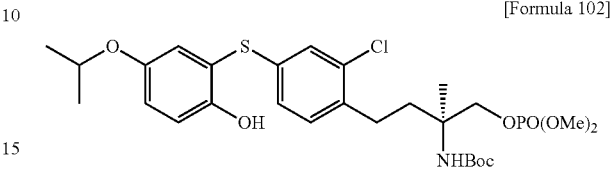

[Formula 102]

The target product (90 mg) was obtained as a colorless oil by reacting the compound of Reference Example 27 (129 mg) in the same manner as in Reference Example 35.

$^1$H NMR (CDCl$_3$, 400 MHz): δ 1.30 (6H, d, J=6.1 Hz), 1.34 (3H, s), 1.43 (9H, s), 1.73 (1H, ddd, J=13.4, 11.0, 6.1 Hz), 1.98-2.10 (1H, m), 2.59-2.75 (2H, m), 3.77 (3H, d, J=11.0 Hz), 3.78 (3H, d, J=11.0 Hz), 4.00 (1H, dd, J=9.8, 4.9 Hz), 4.20 (1H, dd, J=9.8, 4.9 Hz), 4.36-4.46 (1H, m), 4.60 (1H, s), 6.04 (1H, s), 6.90 (1H, dd, J=7.9, 2.4 Hz), 6.95 (1H, dd, J=9.2, 2.4 Hz), 6.99 (1H, d, J=9.2 Hz), 7.04 (1H, d, J=2.4 Hz), 7.06 (1H, d, J=2.4 Hz), 7.08 (1H, d, J=7.9 Hz).

ESIMS (+): 604 [M+H]$^+$.

Reference Example 43

(S)-4-[4-(5-benzyloxy-2-hydroxyphenylthio)-2-chlorophenyl]-2-t-butoxycarbonylamino-1-dimethoxyphosphoryloxy-2-methylbutane

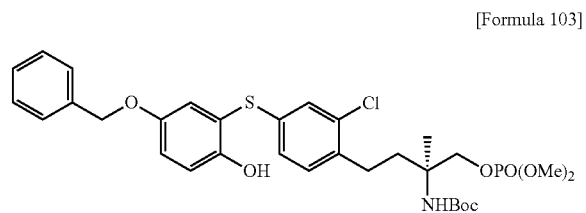

[Formula 103]

The target product (158 mg) was obtained as a colorless oil by reacting the compound of Reference Example 28 (132 mg) in the same manner as in Reference Example 35.

$^1$H NMR (CDCl$_3$, 400 MHz): δ 1.34 (3H, s), 1.43 (9H, s), 1.74 (1H, ddd, J=13.4, 12.2, 5.5 Hz), 1.95-2.14 (1H, m), 2.59-2.73 (2H, m), 3.77 (3H, d, J=11.0 Hz), 3.78 (3H, d, J=11.0 Hz), 4.00 (1H, dd, J=9.8, 4.9 Hz), 4.21 (1H, dd, J=9.8, 4.9 Hz), 4.61 (1H, s), 5.01 (2H, s), 6.06 (1H, s), 6.89 (1H, dd, J=7.9, 1.8 Hz), 7.00 (1H, d, J=9.2 Hz), 7.04 (2H, dd, J=9.2, 1.8 Hz), 7.08 (1H, d, J=7.9 Hz), 7.10 (1H, d, J=2.4 Hz), 7.30-7.43 (5H, m).

ESIMS (+): 652 [M+H]$^+$.

Reference Example 44

(S)-2-t-butoxycarbonylamino-4-[4-(2-t-butoxycarbonyloxy-5-chlorophenylthio)-2-chlorophenyl]-1-dimethoxyphosphoryloxy-2-methylbutane

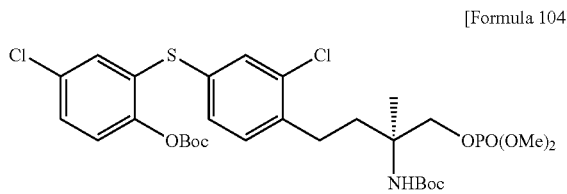

[Formula 104]

The target product (105 mg) was obtained as a colorless oil by reacting the compound of Reference Example 30 (94 mg) in the same manner as in Reference Example 35.

$^1$H NMR (CDCl$_3$, 400 MHz): δ 1.36 (3H, s). 1.45 (9H, s), 1.53 (9H, s), 1.78 (1H, ddd, J=13.4, 11.6, 5.5 Hz), 2.05-2.17 (1H, m), 2.65-2.79 (2H, m), 3.78 (3H, d, J=11.0 Hz), 3.79 (3H, d, J=11.0 Hz), 4.03 (1H, dd, J=9.8, 4.9 Hz), 4.24 (1H, dd, J=9.8, 4.9 Hz), 4.64 (1H, s), 7.11 (1H, d, J=8.6 Hz), 7.14 (1H, d, J=2.4 Hz), 7.16-7.21 (2H, m), 7.23 (1H, dd, J=8.6, 2.4 Hz), 7.39 (1H, d, J=2.4 Hz).

ESIMS (+): 680 [M+H]$^+$.

Reference Example 45

(S)-2-t-butoxycarbonylamino-4-[4-(2-t-butoxycarbonyloxy-5-trifluoromethylphenylthio)-2-chlorophenyl]-1-dimethoxyphosphoryloxy-2-methylbutane

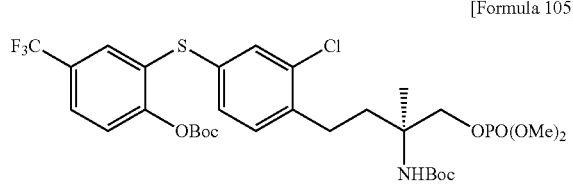

[Formula 105]

The target product (80 mg) was obtained as a colorless oil by reacting the compound of Reference Example 31 (90 mg) in the same manner as in Reference Example 35.

$^1$H NMR (CDCl$_3$, 400 MHz): δ 1.36 (3H, s). 1.44 (9H, s), 1.54 (9H, s), 1.78 (1H, ddd, J=13.4, 12.2, 5.5 Hz), 2.06-2.18 (1H, m), 2.65-2.80 (2H, m), 3.78 (3H, d, J=11.0 Hz), 3.79 (3H, d, J=11.0 Hz), 4.03 (1H, dd, J=9.8, 4.9 Hz), 4.23 (1H, dd, J=9.8, 4.9 Hz), 4.63 (1H, s), 7.19 (2H, d, J=1.2 Hz), 7.30 (1H, d, J=8.6 Hz), 7.39 (1H, d, J=1.2 Hz), 7.46 (1H, d, J=1.8 Hz), 7.53 (1H, dd, J=8.6, 1.8 Hz).

ESIMS (+): 714 [M+H]$^+$.

Reference Example 46

(R)-2-allyl-2-t-butoxycarbonylamino-4-[2-chloro-4-(2-hydroxy-5-trifluoromethylphenylthio)phenyl]-1-dimethoxyphosphoryloxybutane

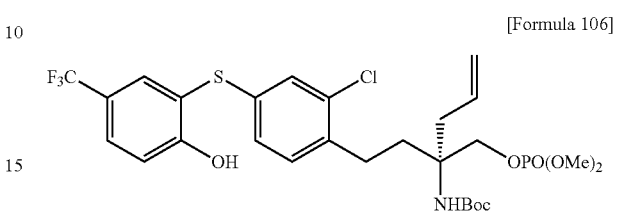

[Formula 106]

The target product (350 mg) was obtained as a colorless oil by reacting the compound of Reference Example 33 (473 mg) in the same manner as in Reference Example 35.

$^1$H NMR (CDCl$_3$, 400 MHz): δ 1.43 (9H, s), 1.75-1.78 (1H, m), 1.90-2.03 (1H, m), 2.41-2.55 (2H, m), 2.64-2.75 (2H, m), 3.78 (6H, d, J=11.0 Hz), 4.08 (1H, dd, J=9.8, 4.9 Hz), 4.19 (1H, dd, J=9.8, 4.9 Hz), 4.58 (1H, s), 5.18 (1H, s), 5.21 (1H, d, J=6.1 Hz), 5.73-5.87 (1H, m), 6.80 (1H, s), 6.90 (1H, dd, J=7.9, 1.8 Hz), 7.09 (1H, d, J=1.8 Hz), 7.12 (1H, d, J=7.9 Hz), 7.15 (1H, d, J=8.6 Hz), 7.63 (1H, dd, J=8.6, 1.8 Hz), 7.80 (1H, d, J=1.8 Hz).

ESIMS (+): 640 [M+H]$^+$.

Reference Example 47

(S)-2-t-butoxycarbonylamino-4-[4-(2-t-butoxycarbonyloxy-5-trifluoromethylphenylthio)-2-chlorophenyl]-1-dimethoxyphosphoryloxy-2-propylbutane

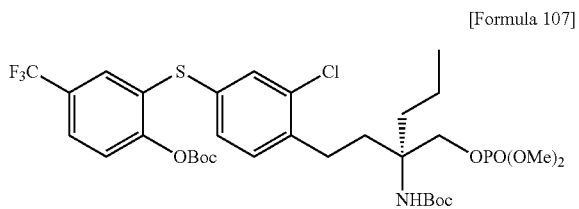

[Formula 107]

The target product (222 mg) was obtained as a colorless oil by reacting the compound of Reference Example 34 (209 mg) in the same manner as in Reference Example 35.

$^1$H NMR (CDCl$_3$, 400 MHz): δ 0.96 (3H, t, J=7.3 Hz), 1.31-1.42 (3H, m). 1.44 (9H, s), 1.54 (9H, s), 1.59-1.72 (1H, m), 1.75-1.85 (1H, m), 1.95-2.11 (1H, m), 2.66-2.74 (2H, m), 3.78 (3H, d, J=11.0 Hz), 3.79 (3H, d, J=11.0 Hz), 4.11 (1H, dd, J=9.8, 4.9 Hz), 4.25 (1H, dd, J=9.8, 4.9 Hz), 4.51 (1H, s), 7.19 (2H, d, J=1.8 Hz), 7.30 (1H, d, J=7.9 Hz), 7.39 (1H, s), 7.46 (1H, d, J=1.8 Hz), 7.53 (1H, dd, J=7.9, 1.8 Hz).

ESIMS (+): 742 [M+H]$^+$.

Example 1

(S)-2-amino-4-[2-chloro-4-(2-hydroxy-5-methylphenylthio)phenyl]-2-methylbutylphosphoric acid monoester

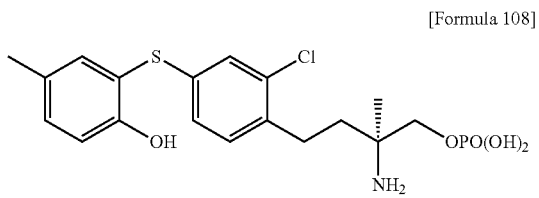

[Formula 108]

Iodotrimethylsilane (97 μL) was added dropwise under ice cooling and under an argon atmosphere to a solution of the compound of Reference Example 35 (84 mg) in acetonitrile (1.4 mL) to form a reaction solution. This reaction solution was stirred under ice cooling for 30 minutes. Then water (10 mL) was added to the reaction solution, and the reaction solution was then further stirred under ice cooling for 30 minutes. The precipitated crystals were then filtrated off, thoroughly washed with water and ethyl acetate, and then dried to obtain the target product (42 mg) as a white powder.

Optical rotation: $[\alpha]_D^{24}$-8.32 (c 0.50, MeOH).

$^1$H NMR (DMSO-d$_6$-dTFA, 400 MHz): δ 1.27 (3H, s), 1.69-1.85 (2H, m), 2.17 (3H, s), 2.66 (2H, t, J=8.6 Hz), 3.85 (1H, dd, J=11.0, 4.9 Hz), 3.92 (1H, dd, J=11.0, 4.9 Hz), 6.86 (1H, d, J=8.6 Hz), 7.01-7.10 (4H, m), 7.25 (1H, d, J=8.6 Hz).

HRESIMS (+): 432.07951 (432.08013 calcd. for $C_{18}H_{24}ClNO_5PS$).

Elemental analysis: measured C, 47.06%; H, 5.35%; N, 2.95%; calcd. for $C_{18}H_{23}ClNO_5PS \cdot 1.5 H_2O$: C, 47.11%; H, 5.71%; N, 3.05%.

Example 2

(S)-2-amino-4-[2-chloro-4-(5-ethyl-2-hydroxyphenylthio)phenyl]-2-methylbutylphosphoric acid monoester

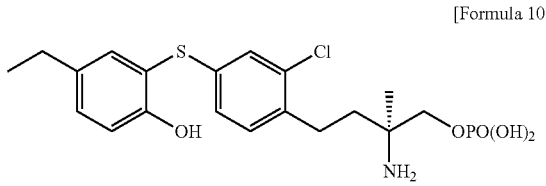

[Formula 109]

The target product (65 mg) was obtained as a white powder by reacting the compound of Reference Example 36 (114 mg) in the same manner as in Example 1.

Optical rotation: $[\alpha]_D^{25}$-9.94 (c 0.50, MeOH).

$^1$H NMR (DMSO-d$_6$-dTFA, 400 MHz): δ 1.09 (3H, t, J=7.3 Hz), 1.27 (3H, s), 1.67-1.86 (2H, m), 2.47 (2H, q, J=7.3 Hz), 2.66 (2H, t, J=8.6 Hz), 3.86 (1H, dd, J=11.0, 4.9 Hz), 3.93 (1H, dd, J=11.0, 4.9 Hz), 6.88 (1H, d, J=7.9 Hz), 7.04 (2H, dd, J=7.9, 1.8 Hz), 7.07-7.14 (2H, m), 7.25 (1H, d, J=8.6 Hz).

HRESIMS (+): 446.09569 (446.09578 calcd. for $C_{19}H_{26}ClNO_5PS$)

Elemental analysis: measured C, 48.89%; H, 5.66%; N, 2.75%; calcd. for $C_{19}H_{25}ClNO_5PS \cdot H_2O$ C, 49.19%; H, 5.87%; N, 3.02%.

Example 3

(S)-2-amino-4-[2-chloro-4-(2-hydroxy-5-propylphenylthio)phenyl]-2-methylbutylphosphoric acid monoester

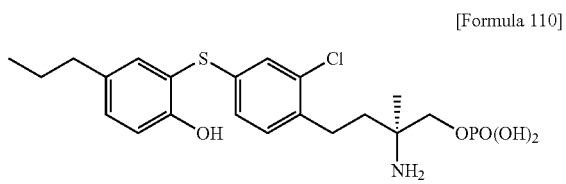

[Formula 110]

The target product (60 mg) was obtained as a white powder by reacting the compound of Reference Example 37 (112 mg) in the same manner as in Example 1.

Optical rotation: $[\alpha]_D^{25}$-9.86 (c 0.50, MeOH).

$^1$H NMR (DMSO-d$_6$-dTFA, 400 MHz): δ 0.82 (3H, t, J=7.3 Hz), 1.27 (3H, s), 1.43-1.56 (2H, m), 1.68-1.85 (2H, m), 2.42 (2H, t, J=7.3 Hz), 2.65 (1H, d, J=7.9 Hz), 2.67 (1H, d, J=7.9 Hz), 3.86 (1H, dd, J=11.0, 4.9 Hz), 3.92 (1H, dd, J=11.0, 4.9 Hz), 6.88 (1H, d, J=7.9 Hz), 7.00-7.11 (4H, m), 7.24 (1H, d, J=8.6 Hz).

HRESIMS (+): 460.11106 (460.11143 calcd. for $C_{20}H_2OClNO_5PS$).

Example 4

(S)-2-amino-4-[(2-chloro-4-(2-hydroxy-5-isopropylphenylthio)phenyl]-2-methylbutylphosphoric acid monoester

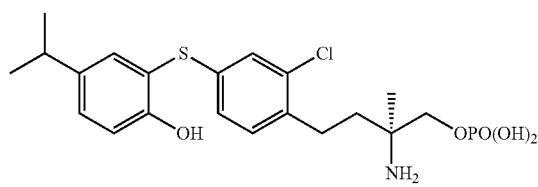

[Formula 111]

The target product (40 mg) was obtained as a white powder by reacting the compound of Reference Example 38 (86 mg) in the same manner as in Example 1.

Optical rotation: $[\alpha]_D^{25}$-8.12 (c 0.50, MeOH).

$^1$H NMR (DMSO-d$_6$-dTFA, 400 MHz): δ 1.12 (6H, d, J=6.7 Hz), 1.27 (3H, s), 1.67-1.87 (2H, m), 2.66 (2H, t, J=8.6 Hz), 2.74-2.81 (1H, m), 3.86 (1H, dd, J=11.0, 4.9 Hz), 3.93 (1H, dd, J=11.0, 4.9 Hz), 6.89 (1H, d, J=7.9 Hz), 7.03 (1H, dd, J=7.9, 1.8 Hz), 7.05 (1H, s), 7.11-7.17 (2H, m), 7.25 (1H, d, J=7.9 Hz).

HRESIMS (+): 460.11124 (460.11143 calcd. for $C_{20}H_{28}ClNO_5PS$)

Elemental analysis: measured C, 50.13%; H, 5.88%; N, 2.72%; calcd. for $C_{20}H_{27}ClNO_5PS \cdot H_2O$ C, 50.26%; H, 6.12%; N, 2.93%.

Example 5

(S)-2-amino-4-[2-chloro-4-(5-cyclopropyl-2-hydroxyphenylthio)phenyl]-2-methylbutylphosphoric acid monoester

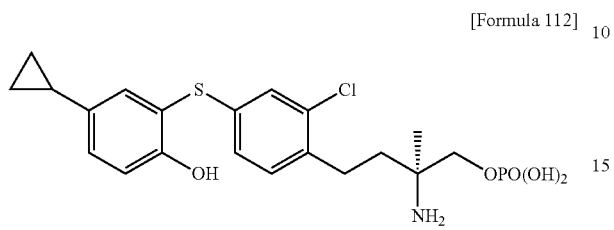

[Formula 112]

The target product (99 mg) was obtained as a white powder by reacting the compound of Reference Example 39 (144 mg) in the same manner as in Example 1.

Optical rotation: $[\alpha]_D^{25}$ -8.15 (c 0.50, MeOH).

$^1$H NMR (DMSO-$d_6$-dTFA, 400 MHz): δ 0.52 (2H, dt, J=6.1, 4.3 Hz), 0.80-0.86 (2H, m), 1.28 (3H, s), 1.67-1.86 (3H, m), 2.66 (2H, t, J=8.6 Hz), 3.86 (1H, dd, J=11.0, 4.9 Hz), 3.93 (1H, dd, J=11.0, 4.9 Hz), 6.85 (1H, d, J=8.6 Hz), 6.96 (1H, dd, J=8.6, 2.4 Hz), 7.01 (1H, d, J=2.4 Hz), 7.04 (1H, dd, J=7.9, 1.8 Hz), 7.05 (1H, s), 7.11-7.17 (2H, m), 7.25 (1H, d, J=7.9 Hz).

HRESIMS (+): 458.09631 (458.09578 calcd. for $C_{20}H_{26}ClNO_5PS$).

Example 6

(S)-2-amino-4-[2-chloro-4-(2-hydroxy-5-methoxyphenylthio)phenyl]-2-methylbutylphosphoric acid monoester

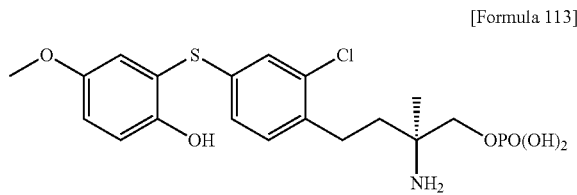

[Formula 113]

The target product (50 mg) was obtained as a white powder by reacting the compound of Reference Example 40 (89 mg) in the same manner as in Example 1.

Optical rotation: $[\alpha]_D^{25}$ -8.31 (c 0.50, MeOH).

$^1$H NMR (DMSO-$d_6$-dTFA, 400 MHz): δ 1.23 (3H, s), 1.64-1.84 (2H, m), 2.66 (2H, t, J=7.9 Hz), 3.63 (3H, s), 3.76 (2H, d, J=11.0 Hz), 6.73 (1H, d, J=3.1 Hz), 6.83 (1H, dd, J=8.6, 3.1 Hz), 6.87 (1H, d, J=8.6 Hz), 7.08 (1H, dd, J=7.9, 1.8 Hz), 7.12 (1H, d, J=1.8 Hz), 7.28 (1H, d, J=7.9 Hz).

HRESIMS (+): 448.07498 (448.07505 calcd. for $C_{18}H_{24}ClNO_6PS$).

Elemental analysis: measured C, 45.69%; H, 5.08%; N, 2.96%; calcd. for $C_{18}H_{23}ClNO_6PS$. 1.2; $H_2O$ C, 46.06%; H, 5.45%; N, 2.98%.

Example 7

(S)-2-amino-4-[2-chloro-4-(5-ethoxy-2-hydroxyphenylthio)phenyl]-2-methylbutylphosphoric acid monoester

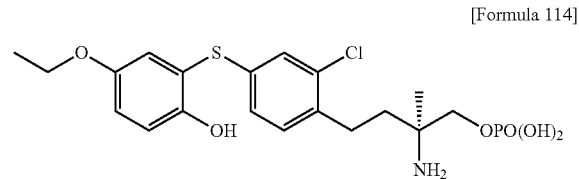

[Formula 114]

The target product (72 mg) was obtained as a white powder by reacting the compound of Reference Example 41 (108 mg) in the same manner as in Example 1.

Optical rotation: $[\alpha]_D^{25}$ -8.50 (c 0.50, MeOH).

$^1$H NMR (DMSO-$d_6$-dTFA, 400 MHz): δ 1.23 (3H, t, J=6.7 Hz), 1.28 (3H, s), 1.70-1.88 (2H, m), 2.68 (2H, t, J=7.9 Hz), 3.87 (2H, q, J=6.7 Hz), 3.88 (1H, dd, J=11.0, 4.9 Hz), 3.93 (1H, dd, J=11.0, 4.9 Hz), 6.71 (1H, d, J=2.4 Hz), 6.83 (1H, dd, J=9.2, 2.4 Hz), 6.86 (1H, d, J=9.2 Hz), 7.11 (1H, dd, J=7.9, 1.8 Hz), 7.13 (1H, d, J=1.8 Hz), 7.28 (1H, d, J=7.9 Hz).

HRESIMS (+): 462.09023 (462.09070 calcd. for $C_{19}H_{26}ClNO_6PS$)

Elemental analysis: measured C, 47.55%; H, 5.32%; N, 2.55%; calcd. for $C_{19}H_{25}ClNO_6PS$. $H_2O$ C, 47.55%; H, 5.67%; N, 2.92%.

Example 8

(S)-2-amino-4-[2-chloro-4-(2-hydroxy-5-isopropoxyphenylthio)phenyl]-2-methylbutylphosphoric acid monoester

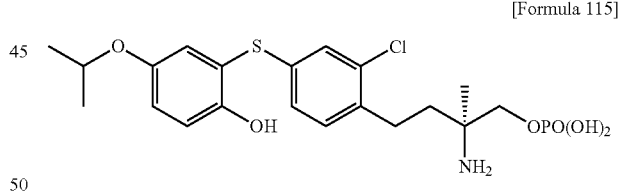

[Formula 115]

The target product (41 mg) was obtained as a white powder by reacting the compound of Reference Example 42 (90 mg) in the same manner as in Example 1.

Optical rotation: $[\alpha]_D^{25}$ -8.51 (c 0.50, MeOH).

$^1$H NMR (DMSO-$d_6$-dTFA, 400 MHz): δ 1.16 (6H, d, J=6.1 Hz), 1.28 (3H, s), 1.71-1.86 (2H, m), 2.68 (2H, t, J=8.6 Hz), 3.88 (1H, dd, J=11.0, 4.9 Hz), 3.93 (1H, dd, J=11.0, 4.9 Hz), 4.31-4.40 (1H, m), 6.69 (1H, d, J=3.1 Hz), 6.81 (1H, dd, J=8.6, 3.1 Hz), 6.85 (1H, d, J=8.6 Hz), 7.12 (1H, dd, J=7.9, 1.8 Hz), 7.14 (1H, d, J=1.8 Hz), 7.28 (1H, d, J=7.9 Hz).

HRESIMS (+): 476.10592 (476.10635 calcd. for $C_{20}H_{28}ClNO_6PS$).

Elemental analysis: measured C, 49.21%; H, 5.61%; N, 2.72%; calcd. for $C_{20}H_{27}ClNO_6PS$. $0.7H_2O$ C, 49.17%; H, 5.86%; N, 2.87%.

Example 9

(S)-2-amino-4-[4-(5-benzyloxy-2-hydroxyphenylthio)-2-chlorophenyl]-2-methylbutylphosphoric acid monoester

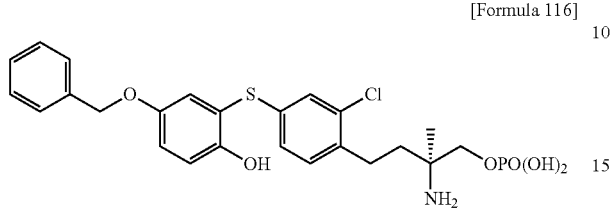

[Formula 116]

The target product (26 mg) was obtained as a white powder by reacting the compound of Reference Example 43 (59 mg) in the same manner as in Example 1.

Optical rotation: $[\alpha]_D^{25}$-9.77 (c 0.50, MeOH).

$^1$H NMR (DMSO-d$_6$-dTFA, 400 MHz): δ 1.27 (3H, s), 1.68-1.86 (2H, m), 2.67 (2H, t, J=8.6 Hz), 3.86 (1H, dd, J=11.0, 4.9 Hz), 3.92 (1H, dd, J=11.0, 4.9 Hz), 4.95 (2H, s), 6.78 (1H, d, J=3.1 Hz), 6.85 (1H, dd, J=9.2, 3.1 Hz), 6.85 (1H, d, J=9.2 Hz), 7.08 (1H, dd, J=7.9, 1.8 Hz), 7.12 (1H, d, J=1.8 Hz), 7.28-7.31 (6H, m).

HRESIMS (+): 524.10694 (524.10635 calcd. for C$_{24}$H$_{28}$ClNO$_6$PS).

Elemental analysis: measured C, 52.62%; H, 5.05%; N, 2.50%; calcd. for C$_{24}$H$_{27}$ClNO$_6$PS. 1.2H$_2$O C, 52.83%; H, 5.43%; N, 2.57%.

Example 10

(S)-2-amino-4-[2-chloro-4-(5-chloro-2-hydroxyphenylthio)phenyl]-2-methylbutylphosphoric acid monoester

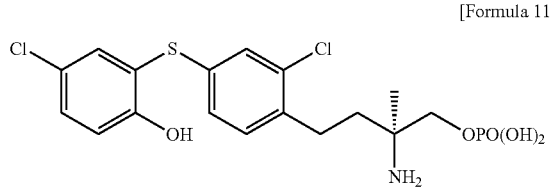

[Formula 117]

The target product (56 mg) was obtained as a white powder by reacting the compound of Reference Example 44 (105 mg) in the same manner as in Example 1.

Optical rotation: $[\alpha]_D^{25}$-8.28 (c 0.50, MeOH).

$^1$H NMR (DMSO-d$_6$-dTFA, 400 MHz): δ 1.29 (3H, s), 1.70-1.90 (2H, m), 2.70 (2H, t, J=8.6 Hz), 3.87 (1H, dd, J=11.0, 4.9 Hz), 3.94 (1H, dd, J=11.0, 4.9 Hz), 6.94 (1H, d, J=8.6 Hz), 7.08 (1H, d, J=2.4 Hz), 7.19 (1H, dt, J=7.9, 1.8 Hz), 7.23 (1H, dt, J=8.6, 2.4 Hz), 7.26 (1H, t, J=8.6 Hz), 7.33 (1H, d, J=7.9 Hz).

HRESIMS (+): 452.02541 (452.02551 calcd. for C$_{17}$H$_{21}$Cl$_2$NO$_5$PS)

Elemental analysis: measured C, 43.98%; H, 4.46%; N, 3.15%; calcd. for C$_{17}$H$_{20}$Cl$_2$NO$_5$PS. 0.5; H$_2$O C, 44.26%; H, 4.59%; N, 3.04%.

Example 11

(S)-2-amino-4-[2-chloro-4-(2-hydroxy-5-trifluoromethylphenylthio)phenyl]-2-methylbutylphosphoric acid monoester

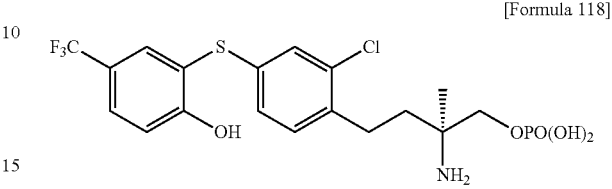

[Formula 118]

The target product (30 mg) was obtained as a white powder by reacting the compound of Reference Example 45 (71 mg) in the same manner as in Example 1.

Optical rotation: $[\alpha]_D^{24}$-7.12 (c 0.50, MeOH).

$^1$H NMR (DMSO-d$_6$-dTFA, 400 MHz): δ 1.28 (3H, s), 1.71-1.88 (2H, m), 2.70 (2H, t, J=8.6 Hz), 3.87 (1H, dd, J=11.0, 4.9 Hz), 3.94 (1H, dd, J=11.0, 4.9 Hz), 7.09 (1H, d, J=8.6 Hz), 7.18 (1H, dd, J=8.6, 1.8 Hz), 7.27 (1H, d, J=1.8 Hz), 7.33 (1H, d, J=8.6 Hz), 7.39 (1H, d, J=1.8 Hz), 7.55 (1H, d, J=8.6 Hz).

HRESIMS (+): 486.05108 (486.05187 calcd. for C$_{18}$H$_{21}$ClF$_3$NO$_5$PS)

Elemental analysis: measured C, 42.61%; H, 4.00%; N, 2.76%; calcd. for C$_{18}$H$_{20}$ClF$_3$NO$_5$PS. H$_2$O C, 42.91%; H, 4.40%; N, 2.78%.

Example 12

(R)-2-allyl-2-amino-4-[2-chloro-4-(2-hydroxy-5-trifluoromethyl phenylthio)phenyl]-butylphosphoric acid monoester

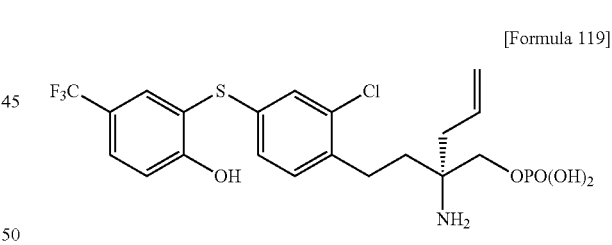

[Formula 119]

The target product (89 mg) was obtained as a white powder by reacting the compound of Reference Example 46 (156 mg) in the same manner as in Example 1.

Optical rotation: $[\alpha]_D^{25}$-7.41 (c 0.50, MeOH).

$^1$H NMR (DMSO-d$_6$-dTFA, 400 MHz): δ 1.65-1.73 (2H, m), 2.39 (2H, d, J=7.3 Hz), 2.66-2.74 (2H, m), 3.42-3.53 (2H, m), 5.19 (1H, dd, J=10.4, 1.8 Hz), 5.24 (1H, dd, J=17.1, 1.8 Hz), 5.55 (1H, s), 5.75-5.88 (1H, m), 7.10 (1H, d, J=8.6 Hz), 7.18 (1H, dd, J=8.6, 1.8 Hz), 7.25 (1H, d, J=1.8 Hz), 7.31 (1H, d, J=8.6 Hz), 7.36 (1H, d, J=1.8 Hz), 7.55 (1H, d, J=8.6 Hz), 7.94 (3H, br s).

HRESIMS (+): 512.06693 (512.06752 calcd. for C$_{20}$H$_{23}$ClF$_3$NO$_5$PS)

Elemental analysis: measured C, 45.80%; H, 4.08%; N, 2.61%; calcd. for C$_{20}$H$_{22}$ClF$_3$NO$_5$PS. 0.5H$_2$O C, 46.12%; H, 4.45%; N, 2.69%.

Example 13

(S)-2-amino-4-[(2-chloro-4-(2-hydroxy-5-trifluoromethylphenylthio)phenyl]-2-propylbutylphosphoric acid monoester

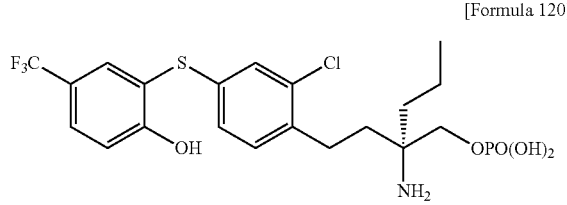

[Formula 120]

The target product (50 mg) was obtained as a white powder by reacting the compound of Reference Example 47 (122 mg) in the same manner as in Example 1.

Optical rotation: $[\alpha]_D^{25}$ -7.67 (c 0.50, MeOH).

$^1$H NMR (DMSO-$d_6$-dTFA, 400 MHz): δ 0.90 (3H, t, J=7.3 Hz), 1.26-1.40 (2H, m), 1.54-1.66 (2H, m), 1.70-1.82 (2H, m), 2.61-2.75 (2H, m), 3.86-3.97 (2H, m), 7.10 (1H, d, J=7.9 Hz), 7.19 (1H, dd, J=7.9, 1.8 Hz), 7.27 (1H, d, J=1.8 Hz), 7.34 (1H, d, J=7.9 Hz), 7.40 (1H, d, J=1.8 Hz), 7.56 (1H, d, J=8.6 Hz).

HRESIMS (+): 514.08255 (514.08317 calcd. for $C_{20}H_{25}ClF_3NO_5PS$).

Reference Example 48

2-Chloro-4-(2-methoxyphenylthio)benzaldehyde

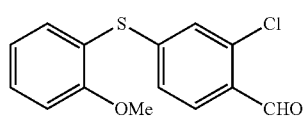

[Formula 121]

The target product (5.50 g) was obtained as a colorless oil by reacting 2-methoxybenzenethiol (2.80 g) and 2-chloro-4-fluorobenzaldehyde (3.17 g) based on the same experiment operations as in Reference Example 1 of WO 03029205 pamphlet.

$^1$H NMR (CDCl$_3$, 400 MHz): δ 3.83 (3H, s), 6.98-7.08 (4H, m), 7.49 (1H, td, J=7.9, 1.2 Hz), 7.52 (1H, dd, J=7.9, 1.2 Hz), 7.74 (1H, d, J=7.9 Hz), 10.34 (1H, s).

EIMS (+): 278 [M]$^+$.

Reference Example 49

[2-Chloro-4-(2-methoxyphenylthio)phenyl]acetaldehyde

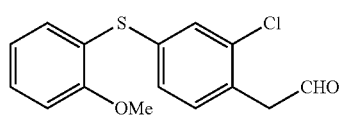

[Formula 122]

The target product (5.60 g) was obtained as a colorless oil by reacting the compound of Reference Example 48 (5.50 g) based on the same experiment operations in Reference Example 326 of WO 04074297 pamphlet.

$^1$H NMR (CDCl$_3$, 400 MHz): δ 3.80 (2H, d, J=1.8 Hz), 3.86 (3H, s), 6.92-6.99 (2H, m), 7.12 (2H, d, J=1.8 Hz), 7.29 (2H, dd, J=7.9, 1.8 Hz), 7.35 (1H, td, J=7.9, 1.8 Hz), 9.73 (1H, t, J=1.8 Hz).

EIMS (+): 292 [M]$^+$.

Reference Example 50

2-Chloro-1-(2-iodoethyl)-4-(2-methoxyphenylthio)benzene

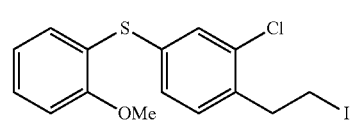

[Formula 123]

The target product (5.40 g) was obtained as a colorless oil by reacting the compound of Reference Example 49 (5.60 g) based on the same experiment operations as in Reference Example 327 of WO 04074297 pamphlet.

$^1$H NMR (CDCl$_3$, 400 MHz): δ 3.25 (2H, ddd, J=8.6, 6.7, 1.8 Hz), 3.34 (2H, ddd, J=8.6, 6.7, 1.8 Hz), 3.86 (3H, s), 6.90-6.96 (2H, m), 7.10 (1H, dd, J=7.9, 1.8 Hz), 7.14 (1H, d, J=7.9 Hz), 7.21-7.26 (2H, m), 7.32 (1H, td, J=7.9, 1.8 Hz).

EIMS (+): 404 [M]$^+$.

Reference Example 51

(2S,5R)-2-[2-chloro-4-(2-methoxyphenylthio)phenyl]ethyl-3,6-dimethoxy-2-methyl-5-isopropyl-2,5-dihydropyrazine

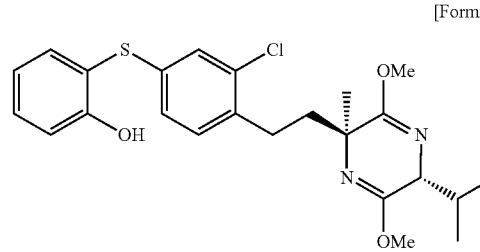

[Formula 127]

The target product (843 mg) was obtained as a colorless oil by reacting the compound of Reference Example 50 (1.23 g) in the same manner as in Reference Example 1:

$^1$H NMR (CDCl$_3$, 400 MHz): δ 0.71 (3H, d, J=6.7 Hz), 1.09 (3H, d, J=6.7 Hz), 1.36 (3H, s), 1.80 (1H, ddd, J=12.8, 11.6, 4.9 Hz), 2.11 (1H, ddd, J=12.8, 11.6, 4.9 Hz), 2.21-2.33 (1H, m), 2.38 (1H, ddd, J=12.8, 11.6, 4.9 Hz), 2.46 (1H, ddd, J=12.8, 11.6, 4.9 Hz), 3.68 (3H, s), 3.69 (3H, s), 3.87 (3H, s), 3.99 (1H, d, J=3.7 Hz), 6.85-6.93 (2H, m), 7.07 (1H, d, J=7.9 Hz), 7.11 (1H, dd, J=7.9, 1.8 Hz), 7.12 (1H, dd, J=7.9, 1.8 Hz), 7.21-7.26 (2H, m).

ESIMS (+): 475 [M+H]$^+$.

Reference Example 52

Methyl(S)-4-[2-chloro-4-(2-methoxyphenylthio)phenyl]-2-t-butoxycarbonylamino-2-methyl butyrate

[Formula 125]

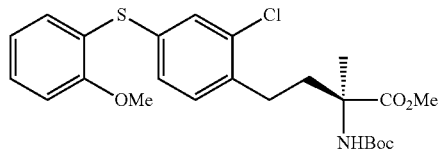

The target product (457 mg) was obtained as a colorless oil by reacting the compound of Reference Example 51 (542 mg) in the same manner as in Reference Example 3.

$^1$H NMR (CDCl$_3$, 400 MHz): δ 1.45 (9H, s), 1.58 (3H, s), 2.11 (1H, ddd, J=13.4, 11.6, 4.9 Hz), 2.38 (1H, br s), 2.52 (1H, td, J=12.8, 4.9 Hz), 2.67 (1H, td, J=12.8, 4.9 Hz), 3.74 (3H, s), 3.86 (3H, s), 5.41 (1H, br s), 6.91 (2H, td, J=7.9, 1.8 Hz), 7.08 (1H, d, J=7.9 Hz), 7.10 (1H, d, J=1.8 Hz), 7.14 (1H, td, J=7.9, 1.8 Hz), 7.28 (2H, td, J=7.9, 1.8 Hz).

ESIMS (+): 480 [M+H]$^+$.

Reference Example 53

(S)-2-t-butoxycarbonylamino-4-[2-chloro-4-(2-methoxyphenylthio)phenyl]-2-methylbutan-1-ol

[Formula 126]

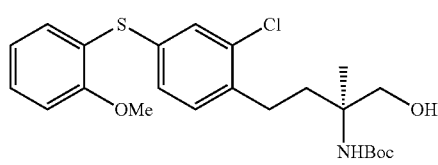

The target product (457 mg) was obtained as a colorless oil by reacting the compound of Reference Example 52 (542 mg) in the same manner as in Reference Example 5.

$^1$H NMR (CDCl$_3$, 400 MHz): δ 1.25 (3H, s), 1.44 (9H, s), 1.81 (1H, ddd, J=13.4, 12.2, 4.9 Hz), 2.06 (1H, ddd, J=13.4, 12.2, 4.9 Hz), 2.68 (1H, td, J=12.8, 4.9 Hz), 2.75 (1H, td, J=12.8, 4.9 Hz), 3.63-3.75 (2H, m), 3.87 (3H, s), 4.09 (1H, br s), 4.68 (1H, s), 6.91 (2H, td, J=7.3, 1.2 Hz), 7.09-7.18 (3H, m), 7.28 (1H, dd, J=7.3, 1.2 Hz).

ESIMS (+): 452 [M+H]$^+$.

Reference Example 54

(S)-2-t-butoxycarbonylamino-4-[4-(2-t-butoxycarbonyloxyphenylthio)-2-chlorophenyl]-1-dimethoxyphosphoryloxy-2-methylbutane

[Formula 127]

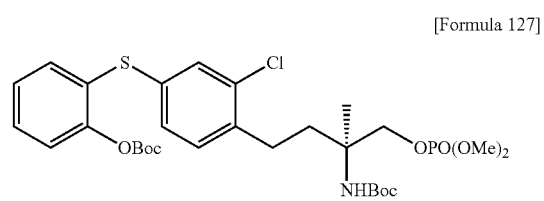

An O-butoxycarbonyl compound (363 mg) was obtained by reacting the compound of Reference Example 53 (457 mg) in the same manner as in Reference Example 30. Then, the target product (169 mg) was obtained as a colorless oil by reacting this O-butoxycarbonyl compound (199 mg) in the same manner as in Reference Example 35.

$^1$H NMR (CDCl$_3$, 400 MHz): δ 1.35 (3H, s), 1.44 (9H, s), 1.52 (9H, s), 1.76 (1H, ddd, J=13.4, 11.0, 5.5 Hz), 2.02-2.16 (1H, m), 2.61-2.77 (2H, m), 3.78 (3H, d, J=11.0 Hz), 3.79 (3H, d, J=11.0 Hz), 4.02 (1H, dd, J=9.8, 5.5 Hz), 4.22 (1H, dd, J=9.8, 5.5 Hz), 4.63 (1H, s), 7.09-7.17 (2H, m), 7.19 (2H, d, J=7.9 Hz), 7.27-7.35 (3H, m).

ESIMS (+): 646 [M+H]$^+$.

Example 14

(S)-2-amino-4-[2-chloro-4-(2-hydroxyphenylthio)phenyl]-2-methylbutylphosphoric acid monoester

[Formula 128]

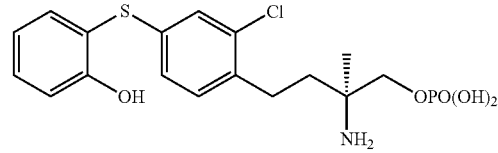

The target product (80 mg) was obtained as a white powder by reacting the compound of Reference Example 54 (199 mg) in the same manner as in Example 1.

Optical rotation: [α]$_D^{27}$ -9.06 (c 0.50, MeOH).

$^1$H NMR (DMSO-d$_6$-dTFA, 400 MHz): δ 1.26 (3H, s), 1.66-1.85 (2H, m), 2.65 (2H, t, J=8.6 Hz), 3.84 (1H, dd, J=11.0, 5.5 Hz), 3.91 (1H, dd, J=11.0, 5.5 Hz), 6.81 (1H, t, J=7.3 Hz), 6.94 (1H, d, J=7.3 Hz), 7.06 (1H, d, J=7.3 Hz, 7.07 (1H, s), 7.21 (2H, d, J=7.9 Hz), 7.25 (1H, d, J=7.9 Hz).

HRESIMS (+): 418.06445 (418.06448 calcd. for C$_{17}$H$_{22}$ClNO$_5$PS)

Elemental analysis: measured C, 47.91%; H, 4.94%; N, 3.21%; calcd. for C$_{17}$H$_{21}$ClNO$_5$PS. 0.4H$_2$O C, 48.04%; H, 5.17%; N, 3.30%.

Reference Example 55

6-t-butyldimethylsilyloxy-1,3-benzoxathiol-2-one

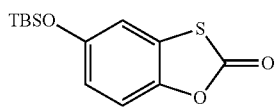
[Formula 129]

Imidazole (972 mg) and t-butylchlorodimethylsilane (2.15 g) were added to a solution of 6-hydroxy-1,3-benzoxathiol-2-one (2.00 g) in N,N-dimethylformamide (60 mL) to form a reaction solution. This reaction solution was stirred for 4 hours at normal temperature. Water was added to the reaction solution, and the reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant residue was purified by silica gel column chromatography (hexane:ethyl acetate=20:1) to obtain the target product (3.00 g) as a colorless oil.

$^1$H NMR (CDCl$_3$, 400 MHz): δ 0.20 (6H, s), 0.98 (9H, s), 6.77 (1H, dd, J=8.6, 2.4 Hz), 6.87 (1H, d, J=2.4 Hz), 7.14 (1H, d, J=8.6 Hz).

CIMS (+): 283 [M+H]$^+$.

Reference Example 56

5-t-butyldimethylsilyloxy-2-hydroxybenzenethiol

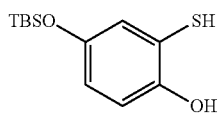
[Formula 130]

The target product (2.72 g) was obtained as a colorless oil by reacting the compound of Reference Example 55 (3.00 g) in the same manner as in Reference Example 16.

$^1$H NMR (CDCl$_3$, 400 MHz): δ 0.16 (6H, s), 0.97 (9H, s), 3.06 (1H, s), 5.73 (1H, s), 6.71 (1H, dd, J=8.6, 2.4 Hz), 6.81 (1H, d, J=2.4 Hz), 6.93 (1H, d, J=8.6 Hz).

CIMS (+): 257 [M+H]$^+$.

Reference Example 57

(S)-2-t-butoxycarbonylamino-4-[4-(5-t-butyldimethylsilyloxy-2-hydroxyphenylthio)-2-chlorophenyl]-2-methylbutan-1-ol

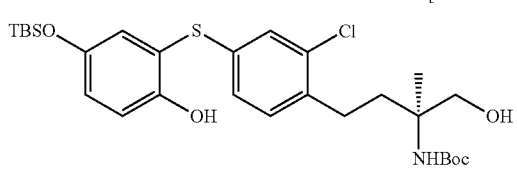
[Formula 131]

The target product (633 mg) was obtained as a colorless oil by reacting the compound of Reference Example 5 (800 mg) and the compound of Reference Example 56 (627 mg) in the same manner as in Reference Example 20.

$^1$H NMR (CDCl$_3$, 400 MHz): δ 0.17 (6H, s), 0.97 (9H, s), 1.23 (3H, s), 1.43 (9H, s), 1.77 (1H, ddd, J=13.4, 12.2, 5.5 Hz), 2.00 (1H, ddd, J=13.4, 12.2, 5.5 Hz), 2.58-2.76 (2H, m), 3.65 (1H, dd, J=11.6, 4.9 Hz), 3.70 (1H, dd, J=11.6, 7.3 Hz), 4.07 (1H, br s), 4.65 (1H, s), 6.05 (1H, s), 6.90 (2H, td, J=8.6, 2.4 Hz), 6.94 (1H, d, J=8.6 Hz), 6.98 (1H, d, J=2.4 Hz), 7.03 (1H, d, J=2.4 Hz), 7.10 (1H, d, J=8.6 Hz).

ESIMS (+): 568 [M+H]$^+$.

Reference Example 58

(S)-2-t-butoxycarbonylamino-4-[4-(5-t-butyldimethylsilyloxy-2-methoxymethoxyphenylthio)-2-chlorophenyl]-2-methylbutan-1-ol

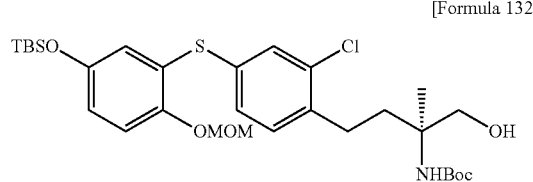
[Formula 132]

Potassium carbonate (185 mg) and chloromethyl methyl ether (102 μL) were added under ice cooling to a solution of the compound of Reference Example 57 (760 mg) in acetone (13.4 mL) to form a reaction solution. This reaction solution was stirred for 3 hours under ice cooling. Water was added to the reaction solution, and the reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant residue was purified by silica gel column chromatography (hexane:ethyl acetate=3:1) to obtain the target product (639 mg) as a colorless oil.

$^1$H NMR (CDCl$_3$, 400 MHz): δ 0.08 (6H, s), 0.91 (9H, s), 1.25 (3H, s), 1.44 (9H, s), 1.80 (1H, ddd, J=13.4, 12.2, 5.5 Hz), 2.02 (1H, ddd, J=13.4, 12.2, 5.5 Hz), 2.69 (1H, td, J=12.8, 4.9 Hz), 2.76 (1H, td, J=12.8, 4.9 Hz), 3.45 (3H, s), 3.67 (1H, dd, J=11.6, 4.9 Hz), 3.72 (1H, dd, J=11.6, 7.3 Hz), 4.08 (1H, br s), 4.68 (1H, s), 5.13 (2H, s), 6.53 (1H, d, J=3.1 Hz), 6.68 (1H, dd, J=9.2, 3.1 Hz), 7.00 (1H, d, J=9.2 Hz), 7.18 (2H, d, J=1.8 Hz), 7.32 (1H, d, J=1.8 Hz).

ESIMS (+): 612 [M+H]$^+$.

Reference Example 59

(S)-2-t-butoxycarbonylamino-4-[2-chloro-4-(5-hydroxy-2-methoxy methoxyphenylthio)phenyl]-2-methylbutan-1-ol

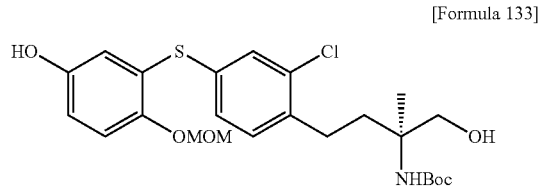
[Formula 133]

A tetrabutylammonium fluoride-tetrahydrofuran solution (1.0 mol/L, 1.0 mL) was added under ice cooling to a solution of the compound of Reference Example 58 (639 mg) in tetrahydrofuran (10 mL) to form a reaction solution. This reaction solution was stirred for 30 minutes under ice cooling. Water was added to the reaction solution, and the reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant residue was purified by silica gel column chromatography (hexane:ethyl acetate=1:1) to obtain the target product (486 mg) as a colorless oil.

¹H NMR (DMSO-d₆, 400 MHz): δ5.17 (3H, s), 1.37 (9H, s), 1.65-1.77 (1H, m), 1.81-1.95 (1H, m), 2.60 (2H, t, J=8.6 Hz), 3.29 (3H, s), 3.36-3.41 (2H, m), 4.72 (1H, t, J=5.5 Hz), 5.08 (2H, s), 6.28 (1H, s), 6.42 (1H, d, J=3.1 Hz), 6.63 (1H, dd, J=9.2, 3.1 Hz), 6.98 (1H, d, J=9.2 Hz), 7.22 (1H, dd, J=7.9, 1.8 Hz), 7.28 (1H, d, J=1.8 Hz), 7.30 (1H, d, J=7.9 Hz), 9.24 (1H, s).

ESIMS (+): 498 [M+H]⁺.

Reference Example 60

(S)-2-t-butoxycarbonylamino-4-[2-chloro-4-(2-methoxymethoxy-5-trifluoromethanesulfonyloxyphenylthio)phenyl]-2-methylbutan-1-ol

[Formula 134]

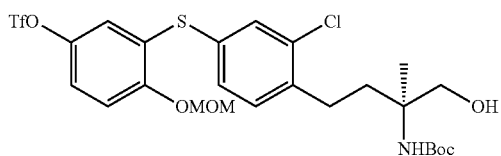

Under an argon atmosphere, triethylamine (273 μL) and N-phenyltrifluoromethanesulfonimide (366 mg) were added under ice cooling to a solution of the compound of Reference Example 59 (486 mg) in methylene chloride (5 mL) to form a reaction solution. This reaction solution was stirred for 2 hours at normal temperature. Water was added to the reaction solution, and the reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant residue was purified by silica gel column chromatography (hexane:ethyl acetate=2:1) to obtain the target product (586 mg) as a colorless oil.

¹H NMR (CDCl₃, 400 MHz): δ 1.26 (3H, s), 1.45 (9H, s), 1.84 (1H, ddd, J=14.1, 12.2, 5.5 Hz), 2.06 (1H, ddd, J=14.1, 12.2, 5.5 Hz), 2.74 (1H, td, J=12.8, 4.9 Hz), 2.81 (1H, td, J=12.8, 4.9 Hz), 3.47 (3H, s), 3.68 (1H, dd, J=11.6, 4.9 Hz), 3.73 (1H, dd, J=11.6, 7.3 Hz), 4.08 (1H, br s), 4.69 (1H, s), 5.24 (2H, s), 6.78 (1H, d, J=3.1 Hz), 7.05 (1H, dd, J=9.2, 3.1 Hz), 7.16 (1H, d, J=9.2 Hz), 7.27 (2H, s), 7.43 (1H, d, J=1.8 Hz).

ESIMS (+): 630 [M+H]⁺.

Reference Example 61

(S)-2-t-butoxycarbonylamino-4-[2-chloro-4-(5-cyano-2-methoxymethoxyphenylthio)phenyl]-2-methylbutan-1-ol

[Formula 135]

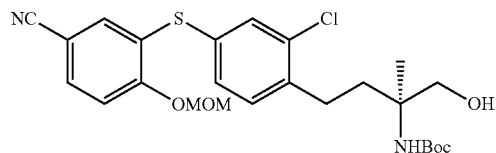

Under an argon atmosphere, 1,1'-bis(diphenylphosphino)-ferrocene (17.6 mg) was added into a solution of tetrakistriphenylphosphine palladium(0) (36.7 mg) in N,N-dimethylformamide (1.6 mL) to form a reaction solution. This reaction solution was stirred for 10 minutes at normal temperature. Then, zinc cyanide (74.5 mg) and the compound of Reference Example 60 (200 mg) were added to the reaction solution, and the reaction solution was stirred for 4 hours at 80° C. Then, tetrakistriphenylphosphine palladium(0) (36.7 mg), 1,1'-bis(diphenylphosphino)-ferrocene (17.6 mg), and zinc cyanide (74.5 mg) were further added to the reaction solution, and the reaction solution was stirred for 2 hours at 80° C. Water was added to the reaction solution, and the reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant residue was purified by silica gel column chromatography (hexane:ethyl acetate=2:1) to obtain the target product (97 mg) as a colorless oil.

¹H NMR (CDCl₃, 400 MHz): δ 1.26 (3H, s), 1.45 (9H, s), 1.84 (1H, ddd, J=14.1, 12.2, 5.5 Hz), 2.07 (1H, ddd, J=14.1, 12.2, 5.5 Hz), 2.69-2.85 (2H, m), 3.47 (3H, s), 3.66-3.75 (2H, m), 4.06 (1H, br s), 4.69 (1H, s), 5.24 (2H, s), 6.78 (1H, d, J=3.1 Hz), 7.05 (1H, dd, J=9.2, 3.1 Hz), 7.16 (1H, d, J=9.2 Hz), 7.27 (2H, s), 7.43 (1H, d, J=1.2 Hz).

ESIMS (+): 490 [M+H]⁺.

Reference Example 62

(S)-4-[4-(5-acetyl-2-methoxymethoxyphenylthio)-2-chlorophenyl]-2-t-butoxycarbonylamino-2-methylbutan-1-ol

[Formula 136]

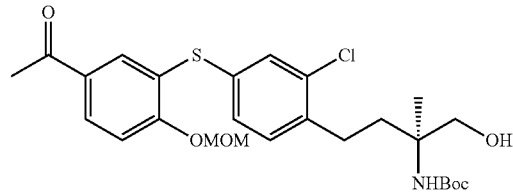

Under an argon atmosphere, 1,3'-bis(diphenylphosphino)-propane (26.2 mg) was added to a solution of palladium(II) acetate (7.1 mg) in N,N-dimethylformamide (1.5 mL) to form a reaction solution. This reaction solution was stirred for 30 minutes at normal temperature. Then, triethylamine (44 μL), butylvinyl ether (205 μL), and a solution of the compound of Reference Example 60 (200 mg) in N,N-dimethylformamide (3.5 mL) were added to the reaction solution, and the reaction solution was stirred for 18 hours at 80° C. A saturated ammonium chloride aqueous solution was added to the reaction solution, and the reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant residue was purified by silica gel column chromatography (hexane:ethyl acetate=2:1) to obtain the target product (117 mg) as a colorless oil.

$^1$H NMR (CDCl$_3$, 400 MHz): δ 1.25 (3H, s), 1.44 (9H, s), 1.81 (1H, ddd, J=14.1, 12.2, 5.5 Hz), 2.04 (1H, ddd, J=14.1, 12.2, 5.5 Hz), 2.50 (3H, s), 2.64-2.81 (2H, m), 3.38 (3H, s), 3.63-3.74 (2H, m), 4.07 (1H, br s), 4.68 (1H, s), 5.27 (2H, s), 7.13-7.21 (3H, m), 7.31 (1H, d, J=1.8 Hz), 7.82 (1H, d, J=1.8 Hz), 7.87 (1H, dd, J=8.6, 1.8 Hz).

ESIMS (+): 524 [M+H]$^+$.

Reference Example 63

(S)-2-t-butoxycarbonylamino-4-[2-chloro-4-(5-cyano-2-methoxymethoxyphenylthio)phenyl]-1-dimethoxyphosphoryloxy-2-methylbutane

[Formula 137]

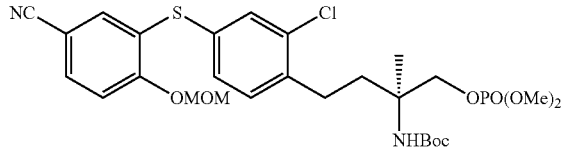

The target product (62 mg) was obtained as a colorless oil by reacting the compound of Reference Example 61 (97 mg) in the same manner as in Reference Example 35.

$^1$H NMR (CDCl$_3$, 400 MHz): δ 1.38 (3H, s), 1.45 (9H, s), 1.82 (1H, ddd, J=13.4, 12.2, 5.5 Hz), 2.07-2.21 (1H, m), 2.69-2.84 (2H, m), 3.45 (3H, s), 3.79 (3H, d, J=11.0 Hz), 3.80 (3H, d, J=11.0 Hz), 4.04 (1H, dd, J=9.8, 5.5 Hz), 4.25 (1H, dd, J=9.8, 5.5 Hz), 4.65 (1H, s), 5.29 (2H, s), 7.15 (1H, d, J=1.8 Hz), 7.17, (1H, d, J=8.6 Hz), 7.25-7.27 (2H, m), 7.42 (1H, t, J=1.8 Hz), 7.46 (1H, J=8.6 Hz).

ESIMS (+): 615 [M+H]$^+$.

Reference Example 64

(S)-4-[4-(5-acetyl-2-methoxymethoxyphenylthio)-2-chlorophenyl]-2-t-butoxycarbonylamino-1-dimethoxyphosphoryloxy-2-methylbutane

[Formula 138]

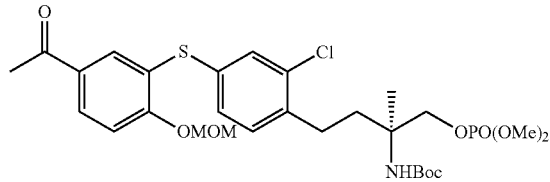

The target product (112 mg) was obtained as a colorless oil by reacting the compound of Reference Example 62 (117 mg) in the same manner as in Reference Example 35.

$^1$H NMR (CDCl$_3$, 400 MHz): δ 1.36 (3H, s), 1.44 (9H, s), 1.76 (1H, ddd, J=13.4, 12.2, 5.5 Hz), 1.98-2.17 (1H, m), 2.50 (3H, s), 2.64-2.76 (2H, m), 3.38 (3H, s), 3.78 (3H, d, J=11.0 Hz), 3.79 (3H, d, J=11.0 Hz), 4.02 (1H, dd, J=9.8, 4.9 Hz), 4.23 (1H, dd, J=9.8, 4.9 Hz), 4.63 (1H, s), 5.26 (2H, s), 7.16 (2H, S), 7.20 (1H, t, J=7.9 Hz), 7.29 (1H, s), 7.84 (1H, d, J=1.8 Hz), 7.88 (1H, dd, J=8.6, 1.8 Hz).

ESIMS (+): 632 [M+H]$^+$.

Example 15

(S)-2-amino-4-[2-chloro-4-(5-cyano-2-hydroxyphenylthio)phenyl]-2-methylbutylphosphoric acid monoester

[Formula 139]

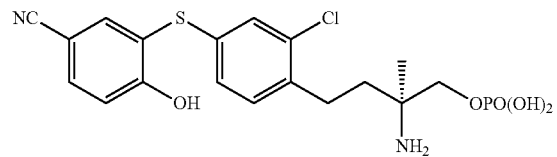

The target product (30 mg) was obtained as a white powder by reacting the compound of Reference Example 63 (62 mg) in the same manner as in Example 1.

Optical rotation: [α]$_D^{25}$-6.74 (c 0.50, MeOH).

$^1$H NMR (DMSO-d$_6$-dTFA, 400 MHz): δ 1.27 (3H, s), 1.69-1.87 (2H, m), 2.70 (2H, t, J=8.6 Hz), 3.86 (1H, dd, J=11.0, 4.9 Hz), 3.93 (1H, dd, J=11.0, 4.9 Hz), 7.04 (1H, d, J=7.9 Hz), 7.20 (1H, dd, J=7.9, 1.2 Hz), 7.26-7.44 (2H, m), 7.48 (1H, d, J=1.8 Hz), 7.63 (1H, dd, J=7.9, 1.8 Hz).

HRESIMS (+): 443.05981 (443.05973 calcd. for C$_{18}$H$_{21}$ClN$_2$O$_5$PS)

Example 16

(S)-4-[4-(5-acetyl-2-hydroxyphenylthio)-2-chlorophenyl]-2-amino-2-methylbutylphosphoric acid monoester

[Formula 140]

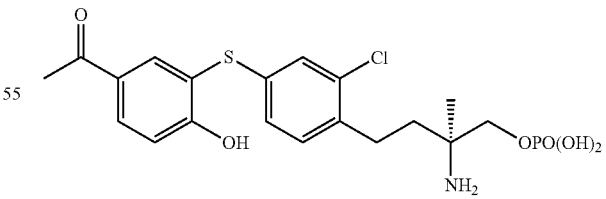

The target product (69 mg) was obtained as a white powder by reacting the compound of Reference Example 64 (112 mg) in the same manner as in Example 1.

Optical rotation: [α]$_D^{25}$-9.53 (c 0.50, MeOH).

$^1$H NMR (DMSO-d$_6$-dTFA, 400 MHz): δ 1.27 (3H, s), 1.68-1.86 (2H, m), 2.43 (3H, s), 2.68 (2H, t, J=8.6 Hz), 3.85 (1H, dd, J=11.0, 4.9 Hz), 3.92 (1H, dd, J=11.0, 4.9 Hz), 7.01

(1H, d, J=7.9 Hz), 7.13 (1H, dd, J=7.9, 1.2 Hz), 7.19 (1H, d, J=1.8 Hz), 7.29 (1H, d, J=7.9 Hz), 7.77 (1H, d, J=1.8 Hz), 7.85 (1H, dd, J=7.9, 1.8 Hz).

HRESIMS (+): 460.07487 (460.07505 calcd. for $C_{19}H_{24}ClNO_6PS$)

Elemental analysis: measured C, 47.44%; H, 5.07%; N, 2.59%; calcd. for $C_{19}H_{22}ClNO_6PS \cdot H_2O$ C, 47.75%; H, 5.27%; N, 2.93%.

Reference Example 65

(S)-2-t-butoxycarbonylamino-4-[2-chloro-4-(2-hydroxy-5-trifluoromethylphenylthio)phenyl]-2-methylbutan-1-ol

[Formula 141]

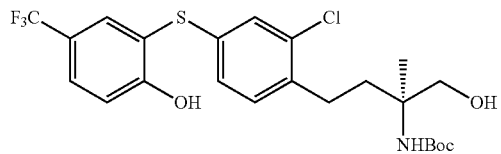

A diphenyl sulfide was obtained by reacting the compound of Reference Example 19 (400 mg) and the compound of Reference Example 5 (554 mg) in the same manner as in Reference Example 20. Then, the target product (480 mg) was obtained as a colorless oil by reacting this diphenyl sulfide in the same manner as in Reference Example 33.

$^1$H NMR (CDCl$_3$, 400 MHz): δ 1.22 (3H, s), 1.43 (9H, s), 1.79 (1H, ddd, J=13.4, 12.2, 5.5 Hz), 2.01 (1H, ddd, J=13.4, 12.2, 5.5 Hz), 2.60-2.76 (2H, m), 3.61-3.73 (2H, m), 4.00 (1H, br s), 4.65 (1H, s), 6.74 (1H, s), 6.91 (1H, dd, J=7.9, 1.8 Hz), 7.09 (1H, d, J=1.8 Hz), 7.12-7.18 (2H, m), 7.63 (1H, dd, J=8.6, 2.4 Hz), 7.80 (1H, d, J=2.4 Hz).

ESIMS (+): 506 [M+H]$^+$.

Reference Example 66

(S)-2-t-butoxycarbonylamino-4-[2-chloro-4-(2-methoxymethoxy-5-trifluoromethylphenylthio)phenyl]-2-methylbutan-1-ol

[Formula 142]

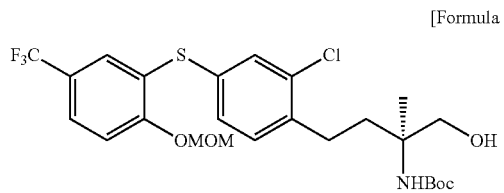

The target product (302 mg) was obtained as a colorless oil by reacting the compound of Reference Example 65 (300 mg) in the same manner as in Reference Example 58.

$^1$H NMR (CDCl$_3$, 400 MHz): δ 1.25 (3H, s), 1.44 (9H, s), 1.82 (1H, ddd, J=13.4, 12.2, 5.5 Hz), 2.06 (1H, ddd, J=13.4, 12.2, 5.5 Hz), 2.66-2.83 (2H, m), 3.41 (3H, s), 3.65-3.74 (2H, m), 4.03 (1H, br s), 4.67 (1H, s), 5.25 (2H, s), 7.16-7.24 (3H, m), 7.35 (1H, d, J=1.8 Hz), 7.36 (1H, d, J=1.8 Hz), 7.47 (1H, dd, J=8.6, 1.8 Hz).

ESIMS (+): 550 [M+H]$^+$.

Reference Example 67

(S)-2-t-butoxycarbonylamino-4-[2-chloro-4-(2-methoxymethoxy-5-trifluoromethylphenylthio)phenyl]-2-methylbutan-1-al

[Formula 143]

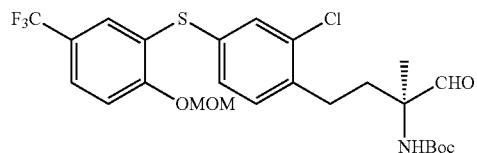

Under an argon atmosphere, a solution of dimethyl sulfide in methylene chloride (1 mL) was added at −78° C. to a solution of oxalyl chloride (67.5 μL) in methylene chloride (5 mL) to form a reaction solution. This reaction solution was stirred at −78° C. for 10 minutes. Then, a solution of the compound of Reference Example 66 (213 mg) in methylene chloride (2 mL) was added to the reaction solution, and the reaction solution was stirred at −78° C. for 1.5 hours. Triethylamine (378 μL) was added to the reaction solution, and then stirred for 30 minutes under ice cooling. Then, a saturated ammonium chloride aqueous solution was added to the reaction solution, and the reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant residue was purified by silica gel column chromatography (hexane:ethyl acetate=3:1) to obtain the target product (201 mg) as a colorless oil.

$^1$H NMR (CDCl$_3$, 400 MHz): δ 1.41 (3H, s), 1.46 (9H, s), 1.91-2.08 (1H, m), 2.16-2.31 (1H, m), 2.57 (1H, ddd, J=13.4, 12.2, 4.9 Hz), 2.68 (1H, ddd, J=13.4, 12.2, 4.9 Hz), 3.41 (3H, s), 5.24 (1H, br s), 5.25 (2H, s), 7.14 (1H, d, J=7.9 Hz), 7.17 (1H, dd, J=7.9, 1.8 Hz), 7.21 (1H, d, J=7.9 Hz), 7.33 (1H, d, J=1.8 Hz), 7.38 (1H, d, J=1.8 Hz), 7.48 (1H, dd, J=7.9, 1.8 Hz), 9.40 (1H, s).

ESIMS (−): 546 [M−H]$^+$.

Reference Example 68

Dimethyl(S)-3-t-butoxycarbonylamino-5-[(2-chloro-4-(2-methoxymethoxy-5-trifluoromethylphenylthio)phenyl]-3-methyl-1-pentenylphosphonate

[Formula 144]

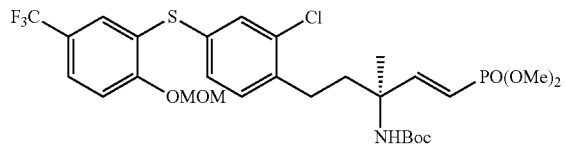

Under an argon atmosphere, an n-butyllithium-hexane solution (1.60 mol/L, 25.5 mL) was added at −78° C. to a solution of tetramethyl methylenediphosphonate (111 mg) in tetrahydrofuran (3 mL) to form a reaction solution. This reaction solution was stirred at −78° C. for 30 minutes. Then, a solution of the compound of Reference Example 67 (111 mg) in tetrahydrofuran (1 mL) was added to the reaction solution. The reaction solution was stirred at −78° C. for 2 hours, and then stirred for 2 hours at normal temperature. Then, a saturated ammonium chloride aqueous solution was added to the reaction solution, and the reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant residue was purified by silica gel column chromatography (hexane:ethyl acetate=2:1, and then ethyl acetate) to obtain the target product (160 mg) as a colorless oil.

$^1$H NMR (CDCl$_3$, 400 MHz): δ 1.44 (3H, s), 1.46 (9H, s), 1.90 (1H, td, J=12.2, 4.9 Hz), 2.06-2.17 (1H, m), 2.61-2.78 (2H, m), 3.41 (3H, s), 3.73 (6H, d, J=11.0 Hz), 4.65 (1H, br s), 5.25 (2H, s), 5.70 (1H, t, J=17.7 Hz), 6.82 (1H, dd, J=22.6, 17.7 Hz), 7.16-7.18 (2H, m), 7.21 (1H, d, J=8.6 Hz), 7.34 (1H, d, J=1.8 Hz), 7.34 (1H, d, J=1.8 Hz), 7.48 (1H, dd, J=8.6, 1.8 Hz).

ESIMS (+): 654 [M+H]$^+$.

Reference Example 69

Dimethyl(S)-3-t-butoxycarbonylamino-5-[2-chloro-4-(2-methoxymethoxy-5-trifluoromethylphenylthio)phenyl]-3-methyl-1-pentylphosphonate

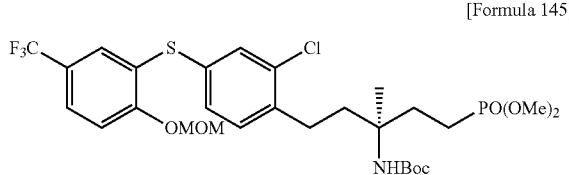

[Formula 145]

10% Palladium-active carbon (200 mg) was added to a solution of the compound of Reference Example 68 (160 mg) in ethyl acetate (16 mL) to form a reaction solution. This reaction solution was, under hydrogen purging, stirred for 20 hours at normal temperature. The reaction solution was filtrated using Celite, and then the solvent was removed by distillation. The resultant residue was purified by silica gel column chromatography (hexane:ethyl acetate=2:1) to obtain the target product (150 mg) as a colorless oil.

$^1$H NMR (CDCl$_3$, 400 MHz): δ 1.30 (3H, s), 1.46 (9H, s), 1.77-1.86 (4H, m), 2.04-2.15 (1H, m), 2.16-2.28 (1H, m), 2.66-2.82 (2H, m), 3.45 (3H, s), 3.79 (6H, d, J=11.0 Hz), 4.44 (1H, br s), 5.30 (2H, s), 7.17-7.28 (3H, m), 7.38-7.42 (2H, m), 7.52 (1H, dd, J=7.9, 2.4 Hz).

ESIMS (+): 656 [M+H]$^+$.

Example 17

(S)-3-amino-5-[2-chloro-4-(2-hydroxy-5-trifluoromethylphenylthio)phenyl]-3-methylpentylphosphonic acid

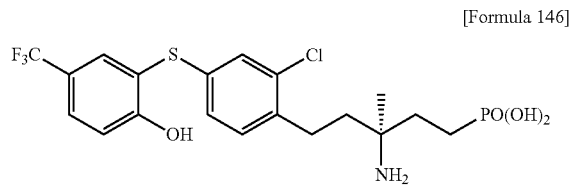

[Formula 146]

The target product (19 mg) was obtained as a white powder by reacting the compound of Reference Example 69 (70 mg) in the same manner as in Example.

Optical rotation: [α]$_D^{25}$ -14.62 (c 0.11, MeOH).

$^1$H NMR (DMSO-d$_6$-dTFA, 400 MHz): δ 1.23 (3H, s), 1.37-1.52 (2H, m), 1.64-1.86 (4H, m), 2.56-2.70 (2H, m), 7.08 (2H, d, J=8.6 Hz), 7.21 (1H, s), 7.24-7.33 (1H, m), 7.41 (1H, s), 7.51 (1H, d, J=8.6 Hz).

HRESIMS (+): 484.07277 (484.07260 calcd. for C$_{19}$H$_{23}$ClF$_3$NO$_4$PS)<

Reference Example 70

(2S,5R)-2-(4-bromo-2-chlorophenyl)ethyl-3,6-dimethoxy-2-propyl-5-isopropyl-2,5-dihydropyrazine

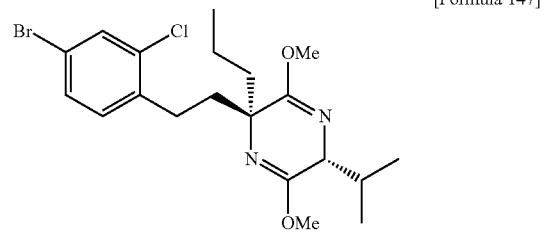

[Formula 147]

The target product (8.01 g) was obtained as a colorless oil by reacting (5R)-3,6-dimethoxy-2-propyl-5-isopropyl-2,5-dihydropyrazine (5.21 g) in the same manner as in Reference Example 1.

$^1$H NMR (CDCl$_3$, 400 MHz): δ 0.70 (3H, d, J=6.7 Hz), 0.86 (3H, t, J=7.3 Hz), 1.11 (3H, d, J=6.7 Hz), 1.15-1.30 (2H, m), 1.49-1.62 (1H, m), 1.71-1.84 (2H, m), 1.98 (1H, td, J=12.4, 4.8 Hz), 2.29-2.47 (3H, m), 3.69 (3H, s), 3.70 (3H, s), 3.95 (1H, d, J=3.0 Hz), 7.01 (1H, d, J=7.9 Hz), 7.27 (1H, dd, J=7.9, 1.8 Hz), 7.46 (1H, d, J=1.8 Hz).

ESIMS (+): 443 [M+H]$^+$.

Reference Example 71

(2S,5R)-2-(4-bromo-2-chlorophenyl)ethyl-2-butyl-3,6-dimethoxy-5-isopropyl-2,5-dihydropyrazine

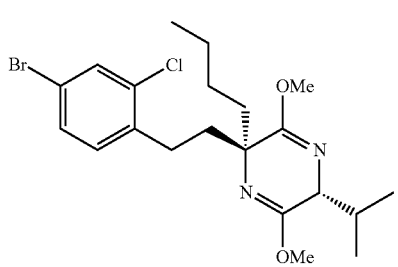

[Formula 148]

The target product (2.52 g) was obtained as a colorless oil by reacting (5R)-2-butyl-3,6-dimethoxy-5-isopropyl-2,5-dihydropyrazine (3.83 g) in the same manner as in Reference Example 1.

$^1$H NMR (CDCl$_3$, 400 MHz): δ 0.71 (3H, d, J=6.7 Hz), 0.85 (3H, t, J=7.3 Hz), 0.94-1.06 (1H, m), 1.11 (3H, d, J=6.7 Hz), 1.12-1.30 (3H, m), 1.57-1.64 (1H, m), 1.74-1.84 (2H, m), 1.98 (1H, dt, J=12.2, 4.9 Hz), 2.30-2.45 (3H, m), 3.70 (3H, s), 3.71 (3H, s), 3.95 (1H, d, J=3.7 Hz), 7.00 (1H, d, J=8.6 Hz), 7.25-7.29 (1H, m), 7.46 (1H, d, J=1.8 Hz).

EIMS (+): 456 [M]$^+$

Reference Example 72

Methyl(S)-4-(4-bromo-2-chlorophenyl)-2-t-butoxycarbonylamino-2-propylbutyrate

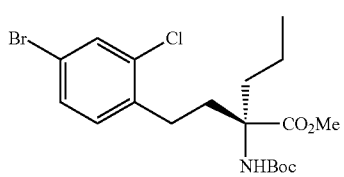

[Formula 149]

The target product (35.6 g) was obtained as a colorless oil by reacting the compound of Reference Example 70 (53.4 g) in the same manner as in Reference Example 4.

$^1$H NMR (CDCl$_3$, 400 MHz): δ 0.89 (3H, t, J=7.3 Hz), 0.96-1.10 (1H, m), 1.25-1.39 (1H, m), 1.46 (9H, s), 1.69 (1H, ddd, J=13.9, 11.5. 4.8 Hz), 1.99-2.10 (1H, m), 2.20-2.35 (1H, m), 2.42 (1H, ddd, J=13.9, 11.5, 4.8 Hz), 2.49-2.60 (1H, m), 2.64 (1H, td, J=13.9, 4.8 Hz), 3.74 (3H, s), 5.62 (1H, br s), 7.03 (1H, d, J=8.5 Hz), 7.29 (1H, dd, J=8.5, 1.8 Hz), 7.48 (1H, J=1.8 Hz).

ESIMS (+): 448 [M+H]$^+$.

Reference Example 73

Methyl(S)-4-(4-bromo-2-chlorophenyl)-2-t-butoxycarbonylamino-2-butyl butyrate

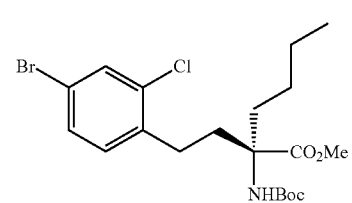

[Formula 150]

The target product (1.26 g) was obtained as a colorless oil by reacting the compound of Reference Example 71 (2.52 g) in the same manner as in Reference Example 4.

$^1$H NMR (CDCl$_3$, 400 MHz): δ 0.87 (3H, t, J=6.7 Hz), 0.95-1.02 (1H, m), 1.22-1.32 (3H, m), 1.46 (9H, s), 1.65-1.75 (1H, m), 2.00-2.10 (1H, m), 2.22-2.34 (1H, m), 2.38-2.48 (1H, m), 2.50-2.70 (2H, m), 3.75 (3H, s), 5.62 (1H, br), 7.02 (1H, d, J=8.6 Hz), 7.28 (1H, dd, J=8.6, 2.4 Hz), 7.47 (1H, d, J=2.4 Hz).

ESIMS (+): 462 [M+H]$^+$.

Reference Example 74

(S)-2-[2-(4-bromo-2-chlorophenyl)ethyl]-2-t-butoxycarbonylaminopentan-1-ol

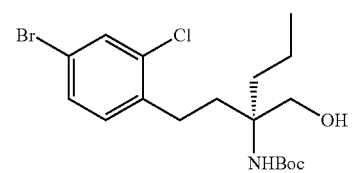

[Formula 151]

The target product (28.6 g) was obtained as a white powder by reacting the compound of Reference Example 72 (35.6 g) in the same manner as in Reference Example 5.

$^1$H NMR (CDCl$_3$, 400 MHz): δ 0.96 (3H, t, J=7.3 Hz), 1.29-1.42 (2H, m), 1.44 (9H, s), 1.53-1.62 (2H, m), 1.81 (1H, ddd, J=13.9, 11.5, 5.4 Hz), 1.93 (1H, ddd, J=13.9, 11.5, 5.4 Hz), 2.59-2.75 (2H, m), 3.73 (2H, d, J=6.7 Hz), 4.15 (1H, br s), 4.62 (1H, br s), 7.11 (1H, d, J=7.9 Hz), 7.31 (1H, dd, J=7.9, 1.8 Hz), 7.49 (1H, d, J=1.8 Hz).

ESIMS (+): 420 [M+H]$^+$.

Reference Example 75

(S)-2-[2-(4-bromo-2-chlorophenyl)ethyl]-2-t-butoxy-carbonylaminohexan-1-ol

[Formula 152]

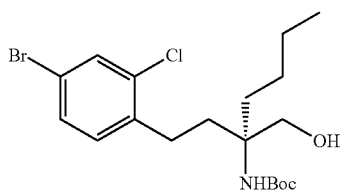

The target product (1.17 g) was obtained as a white powder by reacting the compound of Reference Example 73 (1.26 g) in the same manner as in Reference Example 5.
$^1$H NMR (CDCl$_3$, 400 MHz): δ 0.93 (3H, t, J=7.3 Hz), 1.30-1.40 (4H, m), 1.44 (9H, s), 1.58-1.62 (2H, m), 1.78-1.86 (1H, m), 1.88-1.94 (1H, m), 2.60-2.72 (2H, m), 3.73 (2H, d, J=6.2 Hz), 4.13 (1H, br), 4.62 (1H, br), 7.10 (1H, d, J=8.6 Hz), 7.31 (1H, dd, J=8.6, 2.4 Hz), 7.49 (1H, d, J=2.4 Hz).
ESIMS (+): 434 [M+H]$^+$.

Reference Example 76

5-t-Butyl-2-(methoxymethoxy)benzenethiol

[Formula 153]

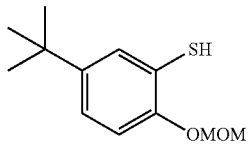

The target product (3.78 g) was obtained as a colorless oil by reacting 1-t-butyl-4-(methoxymethoxy)benzene (10.0 g) in the same manner as in Reference Example 9.
$^1$H NMR (CDCl$_3$, 400 MHz): δ 1.27 (9H, s), 3.51 (3H, s), 3.78 (1H, br), 5.22 (2H, s), 7.01 (1H, d, J=8.6 Hz), 7.09 (1H, dd, J=8.6, 1.8 Hz), 7.26 (1H, d, J=1.8 Hz).
EIMS (+): 226 [M]$^+$.

Reference Example 77

2-(Methoxymethoxy)-5-phenylbenzenethiol

[Formula 154]

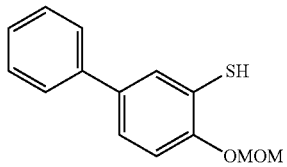

The target product (4.58 g) was obtained as a colorless oil by reacting 4-(methoxymethoxy)biphenyl (10.0 g) in the same manner as in Reference Example 9.
$^1$H NMR (CDCl$_3$, 400 MHz): δ 3.53 (3H, s), 3.86 (1H, s), 5.29 (2H, s), 7.15 (1H, d, J=8.6 Hz), 7.27-7.38 (2H, m), 7.39-7.45 (2H, m), 7.48-7.56 (3H, m).
EIMS (+): 246 [M]$^+$.

Reference Example 78

(S)-2-t-butoxycarbonylamino-4-[2-chloro-4-(2-methoxymethoxy-5-propylphenylthio)phenyl]-2-propylbutan-1-ol

[Formula 155]

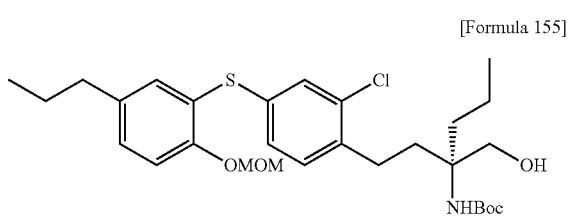

The target product (2.90 g) was obtained as a colorless oil by reacting the compound of Reference Example 11 (2.00 g) and the compound of Reference Example 74 (1.21 g) in the same manner as in Reference Example 20.
$^1$H NMR (CDCl$_3$, 400 MHz): δ 0.90 (3H, t, J=7.3 Hz), 0.95 (3H, t, J=7.3 Hz), 1.30-1.40 (2H, m), 1.44 (9H, s), 1.55-1.60 (2H, m), 1.74-1.84 (2H, m), 1.88-1.94 (2H, m), 2.48 (2H, t, J=7.3 Hz), 2.60-2.70 (2H, m), 3.39 (3H, s), 3.73 (2H, d, J=6.1 Hz), 4.16 (1H, br), 4.62 (1H, br), 5.16 (2H, s), 7.05-7.08 (3H, m), 7.09-7.10 (1H, m), 7.11-7.13 (1H, m), 7.22-7.24 (1H, m).
ESIMS (+): 552 [M+H]$^+$.

Reference Example 79

(S)-2-t-butoxycarbonylamino-4-[2-chloro-4-(2-methoxymethoxy-5-isopropylphenylthio)phenyl]-2-propylbutan-1-ol

[Formula 156]

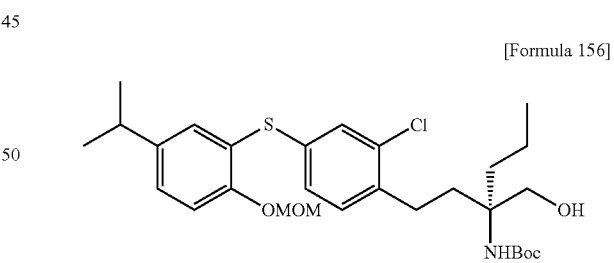

The target product (770 mg) was obtained as a colorless oil by reacting the compound of Reference Example 12 (350 mg) and the compound of Reference Example 74 (584 mg) in the same manner as in Reference Example 20.
$^1$H NMR (CDCl$_3$, 400 MHz): δ 0.95 (3H, t, J=7.3 Hz), 1.18 (6H, d, J=6.7 Hz), 1.30-1.40 (2H, m), 1.44 (9H, s), 1.45-1.60 (2H, m), 1.75-1.83 (1H, m), 1.86-1.95 (1H, m), 2.59-2.71 (2H, m), 2.82 (1H, sept, J=6.7 Hz), 3.39 (3H, s), 3.70-3.72 (2H, m), 4.19 (1H, br), 4.63 (1H, br), 5.16 (2H, s), 7.08-7.16 (5H, m), 7.23 (1H, d, J=1.8 Hz).
ESIMS (+): 552 [M+H]$^+$.

Reference Example 80

(S)-2-t-butoxycarbonylamino-4-[2-chloro-4-(5-cyclopropyl-2-methoxymethoxyphenylthio)phenyl]-2-propylbutan-1-ol

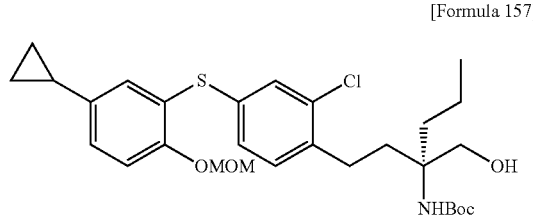

[Formula 157]

The target product (760 mg) was obtained as a colorless oil by reacting the compound of Reference Example 13 (350 mg) and the compound of Reference Example 74 (584 mg) in the same manner as in Reference Example 20.

$^1$H NMR (CDCl$_3$, 400 MHz): δ 0.55-0.60 (2H, m), 0.85-0.92 (2H, m), 0.95 (3H, t, J=7.3 Hz), 1.30-1.40 (2H, m), 1.44 (9H, s), 1.52-1.60 (2H, m), 1.72-1.85 (2H, m), 1.91 (1H, dt, J=11.6, 5.5 Hz), 2.60-2.75 (2H, m), 3.38 (3H, s), 3.73 (2H, d, J=6.1 Hz), 4.18 (1H, br), 4.63 (1H, br), 5.15 (2H, s), 6.96 (1H, dd, J=8.6, 2.4 Hz), 6.99 (1H, d, J=2.4 Hz), 7.02-7.12 (3H, m), 7.23 (1H, d, J=1.8 Hz).

ESIMS (+): 550 [M+H]$^+$.

Reference Example 81

(S)-2-t-butoxycarbonylamino-4-[2-chloro-4-(5-t-butyl-2-methoxy methoxyphenylthio)phenyl]-2-propylbutan-1-ol

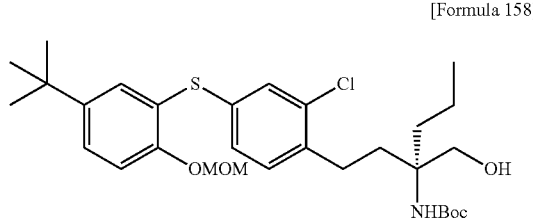

[Formula 158]

The target product (532 mg) was obtained as a colorless oil by reacting the compound of Reference Example 76 (269 mg) and the compound of Reference Example 74 (428 mg) in the same manner as in Reference Example 20.

$^1$H NMR (CDCl$_3$, 400 MHz): δ 0.95 (3H, t, J=7.3 Hz), 1.26 (9H, s), 1.28-1.40 (2H, m), 1.43 (9H, s), 1.50-1.61 (2H, m), 1.72-1.82 (1H, m), 1.84-1.96 (1H, m), 2.58-2.72 (2H, m), 3.38 (3H, s), 3.72 (2H, d, J=6.7 Hz), 4.18 (1H, br), 4.62 (1H, br), 5.16 (2H, s), 7.06 (1H, dd, J=8.6, 1.8 Hz), 7.07-7.14 (2H, m), 7.21 (1H, d, J=1.8 Hz), 7.30 (1H, dd, J=8.6, 3.0 Hz), 7.33 (1H, d, J=3.0 Hz).

ESIMS (+): 566 [M+H]$^+$.

Reference Example 82

(S)-2-t-butoxycarbonylamino-4-[2-chloro-4-(2-methoxymethoxy-5-biphenylthio)phenyl]-2-propylbutan-1-ol

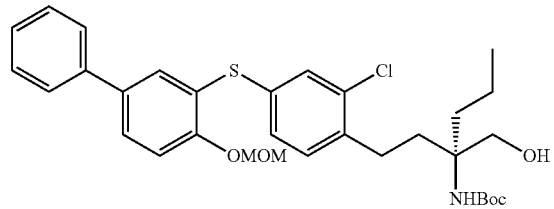

[Formula 159]

The target product (453 mg) was obtained as a colorless oil by reacting the compound of Reference Example 77 (118 mg) and the compound of Reference Example 74 (428 mg) in the same manner as in Reference Example 20.

$^1$H NMR (CDCl$_3$, 400 MHz): δ 0.95 (3H, t, J=7.3 Hz), 1.28-1.40 (2H, m), 1.43 (9H, s), 1.54-1.62 (2H, m), 1.75-1.85 (1H, m), 1.88-1.96 (1H, m), 2.60-2.74 (2H, m), 3.42 (3H, s), 3.72 (2H, d, J=6.1 Hz), 4.16 (1H, br), 4.62 (1H, br), 5.24 (2H, s), 7.14-7.16 (2H, m), 7.22 (1H, d, J=8.6 Hz), 7.28-7.34 (2H, m), 7.34-7.42 (2H, m), 7.44-7.50 (4H, m).

ESIMS (+): 586 [M+H]$^+$.

Reference Example 83

(S)-2-t-butoxycarbonylamino-4-[4-(5-benzyloxy-2-hydroxyphenylthio)-2-chlorophenyl]-2-propylbutan-1-ol

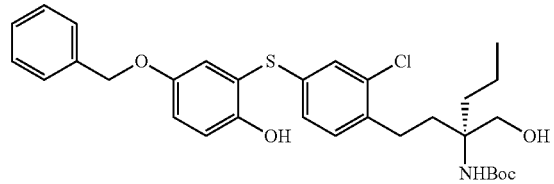

[Formula 160]

The target product (705 mg) was obtained as a colorless oil by reacting 5-benzyloxy-2-hydroxybenzenethiol (161 mg) and the compound of Reference Example 74 (583 mg) in the same manner as in Reference Example 20.

$^1$H NMR (CDCl$_3$, 400 MHz): δ 0.95 (3H, t, J=7.3 Hz), 1.20-1.40 (2H, m), 1.43 (9H, s), 1.52-1.58 (2H, m), 1.72-1.94 (2H, m), 2.55-2.70 (2H, m), 3.71 (2H, d, J=6.7 Hz), 4.15 (1H, br), 4.61 (1H, br), 5.00 (2H, s), 6.06 (1H, s), 6.89 (1H, dd, J=8.5, 1.8 Hz), 6.99 (1H, d, J=8.5 Hz), 7.02-7.07 (2H, m), 7.08-7.12 (2H, m), 7.30-7.42 (5H, m).

ESIMS (+): 572 [M+H]$^+$.

Reference Example 84

(S)-2-t-butoxycarbonylamino-4-[2-chloro-4-(2-methoxy-5-trifluoromethylphenylthio)phenyl]-2-butylbutan-1-ol

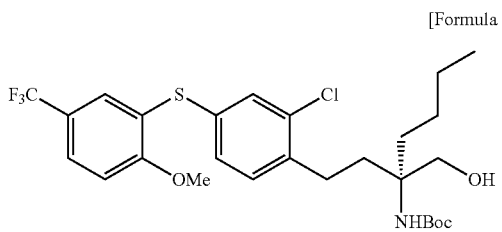

[Formula 161]

The target product (479 mg) was obtained as a colorless oil by reacting the compound of Reference Example 19 (230 mg) and the compound of Reference Example 75 (400 mg) in the same manner as in Reference Example 20.

$^1$H NMR (CDCl$_3$, 400 MHz): δ 0.94 (3H, t, J=7.3 Hz), 1.20-1.40 (4H, m), 1.44 (9H, s), 1.57-1.62 (2H, m), 1.78-1.88 (1H, m), 1.90-2.00 (1H, m), 2.60-2.78 (2H, m), 3.74 (2H, d, J=6.7 Hz), 3.92 (3H, s), 4.20 (1H, br), 4.63 (1H, br), 6.95 (1H, d, J=8.6 Hz), 7.15-7.21 (2H, m), 7.31-7.35 (2H, m), 7.47-7.54 (1H, m).

ESIMS (+): 562 [M+H]$^+$.

Reference Example 85

(S)-2-t-butoxycarbonylamino-4-[4-(2-t-butoxycarbonyloxy-5-trifluoromethylphenylthio)-2-chlorophenyl]-2-butylbutan-1-ol

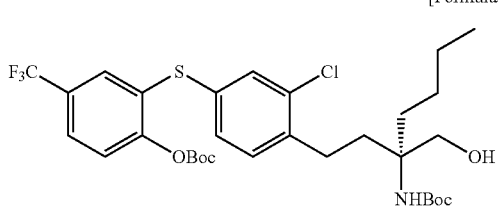

[Formula 162]

The target product (319 mg) was obtained as a colorless oil by reacting the compound of Reference Example 84 (440 mg) in the same manner as in Reference Example 30.

$^1$H NMR (CDCl$_3$, 400 MHz): δ 0.93 (3H, t, J=7.3 Hz), 1.20-1.40 (4H, m), 1.44 (9H, s), 1.54 (9H, s), 1.56-1.62 (2H, m), 1.77-1.87 (1H, m), 1.90-1.97 (1H, m), 2.60-2.80 (2H, m), 3.73 (2H, d, J=6.1 Hz), 4.13 (1H, br), 4.62 (1H, br), 7.20 (2H, m), 7.30 (1H, d, J=8.6 Hz), 7.39 (1H, s), 7.47 (1H, d, J=1.8 Hz), 7.53 (1H, dd, J=8.6, 1.8 Hz).

ESIMS (+): 648 [M+H]$^+$.

Reference Example 86

(S)-2-t-butoxycarbonylamino-4-[2-chloro-4-(2-methoxymethoxy-5-propylphenylthio)phenyl]-1-dimethoxyphosphoryloxy-2-propylbutane

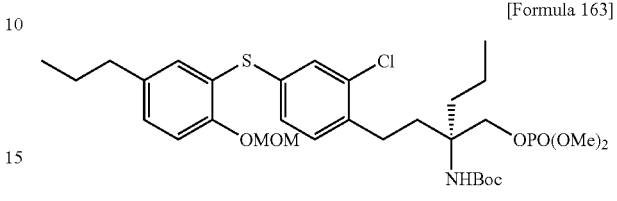

[Formula 163]

The target product (1.90 g) was obtained as a colorless oil by reacting the compound of Reference Example 78 (2.90 g) in the same manner as in Reference Example 35.

$^1$H NMR (CDCl$_3$, 400 MHz): δ 0.90 (3H, t, J=7.3 Hz), 0.95 (3H, t, J=7.3 Hz), 1.30-1.40 (2H, m), 1.43 (9H, s), 1.52-1.60 (2H, m), 1.61-1.71 (2H, m), 1.72-1.82 (1H, m), 1.85-2.05 (1H, m), 2.48 (2H, t, J=7.3 Hz), 2.66 (2H, t, J=8.6 Hz), 3.39 (3H, s), 3.77 (3H, d, J=11.0 Hz), 3.78 (3H, d, J=11.0 Hz), 4.06-4.14 (1H, m), 4.23 (1H, dd, J=10.3, 4.9 Hz), 4.50 (1H, br), 5.16 (2H, s), 7.06-7.12 (5H, m), 7.22 (1H, d, J=1.8 Hz).

ESIMS (+): 660 [M+H]$^+$.

Reference Example 87

(S)-2-t-butoxycarbonylamino-4-[2-chloro-4-(2-methoxymethoxy-5-isopropylphenylthio)phenyl]-1-dimethoxyphosphoryloxy-2-propylbutane

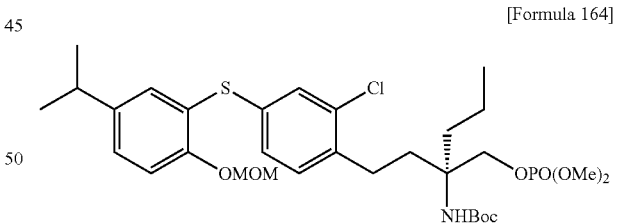

[Formula 164]

The target product (687 mg) was obtained as a colorless oil by reacting the compound of Reference Example 79 (650 mg) in the same manner as in Reference Example 35.

$^1$H NMR (CDCl$_3$, 400 MHz): δ 0.95 (3H, t, J=7.2 Hz), 1.18 (6H, d, J=6.8 Hz), 1.20-1.40 (4H, m), 1.44 (9H, s), 1.58-1.82 (2H, m), 2.66 (2H, t, J=8.4 Hz), 2.82 (1H, sept, J=6.8 Hz), 3.39 (3H, s), 3.77 (3H, d, J=11.0 Hz), 3.78 (3H, d, J=11.0 Hz), 4.08-4.14 (1H, m), 4.20-4.26 (1H, m), 4.50 (1H, br), 5.16 (2H, s), 7.02-7.20 (5H, m), 7.23 (1H, d, J=1.6 Hz).

ESIMS (+): 660 [M+H]$^+$.

Reference Example 88

(S)-2-t-butoxycarbonylamino-4-[2-chloro-4-(5-cyclopropyl-2-methoxymethoxyphenylthio)phenyl]-1-dimethoxyphosphoryloxy-2-propylbutane

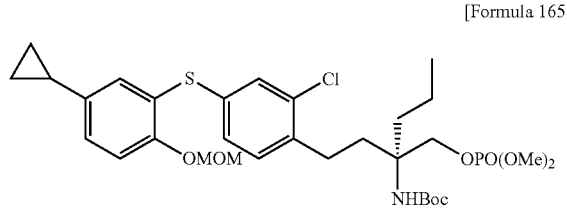

[Formula 165]

The target product (622 mg) was obtained as a colorless oil by reacting the compound of Reference Example 80 (710 mg) in the same manner as in Reference Example 35.

$^1$H NMR (CDCl$_3$, 400 MHz): δ 0.55-0.60 (2H, m), 0.85-0.90 (2H, m), 0.95 (3H, t, J=7.3 Hz), 1.30-1.40 (2H, m), 1.44 (9H, s), 1.54-1.68 (2H, m), 1.72-1.84 (2H, m), 1.95-2.05 (1H, m), 2.66 (2H, t, J=8.6 Hz), 3.38 (3H, s), 3.77 (3H, d, J=11.0 Hz), 3.78 (3H, d, J=11.0 Hz), 4.11 (1H, dd, J=9.7, 4.9 Hz), 4.23 (1H, dd, J=9.7, 4.9 Hz), 4.50 (1H, br), 5.14 (2H, s), 6.96 (1H, dd, J=8.6, 2.4 Hz), 6.99 (1H, d, J=2.4 Hz), 7.02-7.12 (3H, m), 7.23 (1H, d, J=1.8 Hz).

ESIMS (+): 658 [M+H]$^+$.

Reference Example 89

(S)-2-t-butoxycarbonylamino-4-[2-chloro-4-(5-t-butyl-2-methoxy methoxyphenylthio)phenyl]-1-dimethoxyphosphoryloxy-2-propylbutane

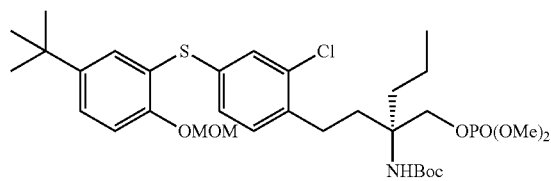

[Formula 166]

The target product (308 mg) was obtained as a colorless oil by reacting the compound of Reference Example 81 (400 mg) in the same manner as in Reference Example 35.

$^1$H NMR (CDCl$_3$, 400 MHz): δ 0.95 (3H, t, J=7.3 Hz), 1.26 (9H, s), 1.30-1.40 (2H, m), 1.44 (9H, s), 1.60-1.80 (3H, m), 1.90-2.05 (1H, m), 2.62-2.76 (2H, m), 3.38 (3H, s), 3.77 (3H, d, J=11.0 Hz), 3.78 (3H, d, J=11.0 Hz), 4.09-4.14 (1H, m), 4.23 (1H, dd, J=9.8, 4.0 Hz), 4.49 (1H, br), 5.16 (2H, s), 7.05 (1H, dd, J=8.0, 1.8 Hz), 7.08-7.12 (2H, m), 7.21 (1H, d, J=1.8 Hz), 7.30 (1H, dd, J=8.6, 2.4 Hz), 7.33 (1H, d, J=2.4 Hz).

ESIMS (+): 674 [M+H]$^+$.

Reference Example 90

(S)-2-t-butoxycarbonylamino-4-[2-chloro-4-(2-methoxymethoxy-5-biphenylthio)phenyl]-1-dimethoxyphosphoryloxy-2-propylbutane

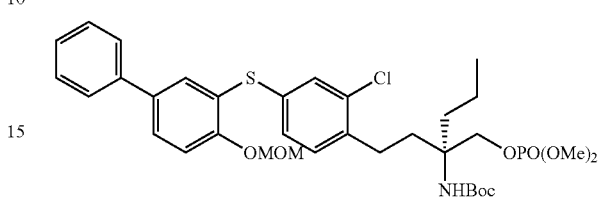

[Formula 167]

The target product (421 mg) was obtained as a colorless oil by reacting the compound of Reference Example 82 (360 mg) in the same manner as in Reference Example 35.

$^1$H NMR (CDCl$_3$, 400 MHz): δ 0.95 (3H, t, J=7.3 Hz), 1.30-1.38 (2H, m), 1.43 (9H, m), 1.60-1.70 (2H, m), 1.72-1.82 (1H, m), 1.85-2.02 (1H, m), 2.62-2.72 (2H, m), 3.42 (3H, s), 3.77 (3H, d, J=11.0 Hz), 3.78 (3H, d, J=11.0 Hz), 4.09-4.14 (1H, m), 4.20-4.28 (1H, m), 4.50 (1H, br), 5.23 (2H, s), 7.10-7.17 (2H, m), 7.20-7.25 (1H, m), 7.28-7.34 (2H, m), 7.36-7.43 (2H, m), 7.45-7.51 (4H, m).

ESIMS (+): 694 [M+H]$^+$.

Reference Example 91

(S)-4-[4-(5-benzyloxy-2-hydroxyphenylthio)-2-chlorophenyl]-2-t-butoxycarbonylamino-1-dimethoxyphosphoryloxy-2-propylbutane

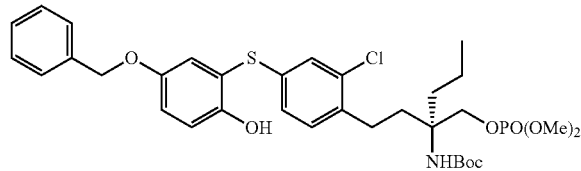

[Formula 168]

The target product (445 mg) was obtained as a colorless oil by reacting the compound of Reference Example 83 (450 mg) in the same manner as in Reference Example 35.

$^1$H NMR (CDCl$_3$, 400 MHz): δ 0.94 (3H, t, J=7.3 Hz), 1.28-1.38 (2H, m), 1.43 (9H, s), 1.58-1.68 (2H, m), 1.72-1.82 (1H, m), 1.90-2.05 (1H, m), 2.58-2.68 (2H, m), 3.77 (3H, d, J=11.0 Hz), 3.78 (3H, d, J=11.0 Hz), 4.02-4.12 (1H, m), 4.22 (1H, dd, J=10.4, 5.5 Hz), 5.00 (2H, s), 6.07 (1H, s), 6.88 (1H, dd, J=8.0, 2.4 Hz), 6.99 (1H, d, J=8.0 Hz), 7.02-7.12 (4H, m), 7.30-7.38 (1H, m), 7.35-7.42 (4H, m).

ESIMS (+): 680 [M+H]$^+$.

Reference Example 92

(S)-2-t-butoxycarbonylamino-4-[4-(2-t-butoxycarbonyloxy-5-trifluoromethylphenylthio)-2-chlorophenyl]-1-dimethoxyphosphoryloxy-2-butylbutane

[Formula 169]

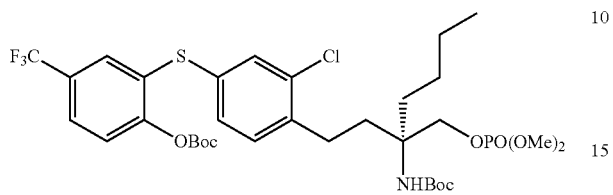

The target product (258 mg) was obtained as a colorless oil by reacting the compound of Reference Example 85 (260 mg) in the same manner as in Reference Example 35.

$^1$H NMR (CDCl$_3$, 400 MHz): δ 0.93 (3H, t, J=7.3 Hz), 1.27-1.40 (4H, m), 1.44 (9H, s), 1.54 (9H, s), 1.62-1.70 (2H, m), 1.77-1.84 (1H, m), 1.96-2.04 (1H, m), 2.64-2.74 (2H, m), 3.77 (3H, d, J=11.0 Hz), 3.78 (3H, d, J=11.0 Hz), 4.08-4.14 (1H, m), 4.20-4.27 (1H, m), 7.19 (2H, m), 7.30 (1H, d, J=8.6 Hz), 7.39 (1H, s), 7.47 (1H, d, J=1.8 Hz), 7.53 (1H, dd, J=8.6, 1.8 Hz).

ESIMS (+): 756 [M+H]$^+$.

Example 18

(S)-2-amino-4-[2-chloro-4-(2-hydroxy-5-propylphenylthio)phenyl]-2-propylbutylphosphoric acid monoester

[Formula 170]

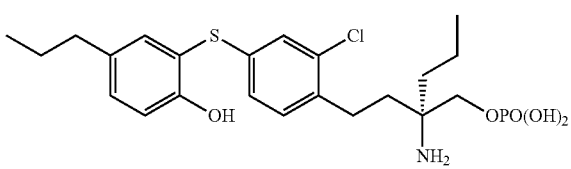

The compound of Reference Example 86 (1.90 g) was dissolved in 10% hydrogen chloride-methanol (19 mL) to form a first reaction solution. This first reaction solution was stirred at 40° C. for 3 hours. The solvent in the first reaction solution was removed by distillation under reduced pressure, and the resultant residue was dissolved in acetonitrile (20 mL). Under an argon atmosphere, iodotrimethylsilane (1.85 mL) was added dropwise under ice cooling to the acetonitrile solution to form a second reaction solution. This second reaction solution was stirred under ice cooling for 30 minutes. Water (80 mL) was added to the second reaction solution, and the reaction solution was stirred under ice cooling for a further 30 minutes. The oily product was then separated by decantation. The obtained oily product was dried, and then recrystallized in acetonitrile-tetrahydrofuran. The solid obtained from the recrystallization was dissolved in a 0.5 mol/L sodium hydroxide aqueous solution (10.0 mL), and 1.0 mol/L hydrochloric acid was then added to the resultant solution to adjust the pH to 3. The precipitated solid was removed by filtration and then dried to obtain the target product (1.00 g) as a white powder.

Optical rotation: [α]$_D^{26}$-2.00 (c 0.51, MeOH).

$^1$H NMR (DMSO-d$_6$, 400 MHz): δ 0.82 (3H, t, J=7.3 Hz), 0.88 (3H, t, J=7.3 Hz), 1.20-1.35 (2H, m), 1.43-1.60 (4H, m), 1.64-1.76 (2H, m), 2.41 (2H, t, J=7.3 Hz), 2.54-2.66 (2H, m), 3.65-3.85 (2H, m), 6.87 (1H, d, J=8.6 Hz), 6.98-7.04 (2H, m), 7.05-7.09 (2H, m), 7.24 (1H, d, J=8.6 Hz).

HRESIMS (+): 488.1430 (488.1427 calcd. for C$_{22}$H$_{32}$ClNO$_5$PS)

Elemental analysis: measured C, 52.49%; H, 6.24%; N, 2.79%; calcd.

for C$_{22}$H$_{31}$ClNO$_5$PS. 0.75H$_2$O C, 52.69%; H, 6.53%; N, 2.79%.

Example 19

(S)-2-amino-4-[2-chloro-4-(2-hydroxy-5-isopropylphenylthio)phenyl]-2-propylbutylphosphoric acid monoester

[Formula 171]

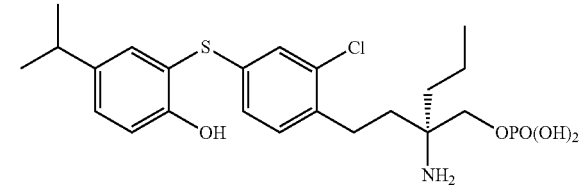

The target product (376 mg) was obtained as a white powder by reacting the compound of Reference Example 87 (640 mg) in the same manner as in Example 1.

Optical rotation: [α]$_D^{25}$-2.08 (c 0.50, MeOH).

$^1$H NMR (DMSO-d$_6$, 400 MHz): δ 0.87 (3H, t, J=7.3 Hz), 1.11 (6H, d, J=6.7 Hz), 1.20-1.40 (2H, m), 1.45-1.60 (2H, m), 1.68 (2H, br), 2.59 (2H, br), 2.76 (1H, sept, J=6.7 Hz), 3.70-3.82 (2H, m), 6.89 (1H, d, J=8.4 Hz), 6.95-7.05 (2H, m), 7.10-7.15 (2H, m), 7.24 (1H, d, J=8.4 Hz).

HRESIMS (+): 488.1433 (488.1427 calcd. for C$_{22}$H$_{32}$ClNO$_5$PS)

Elemental analysis: measured C, 51.93%; H, 6.38%; N, 2.69%; calcd. for C$_{22}$H$_{31}$ClNO$_5$PS. H$_2$O C, 52.22%; H, 6.18%; N, 2.77%.

Example 20

(S)-2-amino-4-[2-chloro-4-(5-cyclopropyl-2-hydroxyphenylthio)phenyl]-2-propylbutylphosphoric acid monoester

[Formula 172]

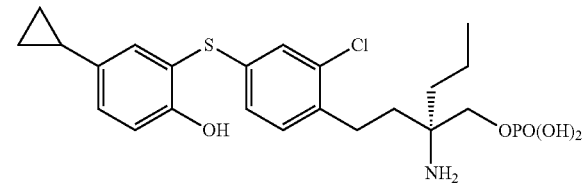

The target product (314 mg) was obtained as a white powder by reacting the compound of Reference Example 88 (622 mg) in the same manner as in Example 1.

Optical rotation: $[\alpha]_D^{26}$ −1.68 (c 0.50, MeOH).

$^1$H NMR (DMSO-$d_6$, 400 MHz): δ 0.50-0.58 (2H, m), 0.80-0.87 (2H, m), 0.91 (3H, t, J=7.4 Hz), 1.28-1.40 (2H, m), 1.50-1.63 (2H, m), 1.68-1.76 (2H, m), 1.78-1.88 (1H, m), 2.58-2.70 (2H, m), 3.70-3.84 (2H, m), 6.87 (1H, d, J=8.4 Hz), 6.97 (1H, dd, J=8.4, 1.8 Hz), 7.00-7.07 (3H, m), 7.28 (1H, d, J=8.0 Hz).

HRESIMS (+): 486.1276 (486.1271 calcd. for $C_{22}H_{30}ClNO_5PS$).

Elemental analysis: measured C, 52.06%; H, 5.97%; N, 2.64%; calcd. for $C_{22}H_{29}ClNO_5PS \cdot 1.2H_2O$ C, 52.06%; H, 5.76%; N, 2.76%.

Example 21

(S)-2-amino-4-[4-(5-t-butyl-2-hydroxyphenylthio)-2-chlorophenyl]-2-propylbutylphosphoric acid monoester

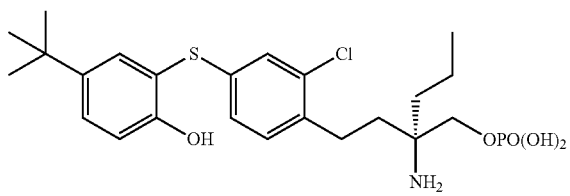

[Formula 173]

The target product (157 mg) was obtained as a white powder by reacting the compound of Reference Example 89 (308 mg) in the same manner as in Example 1.

Optical rotation: $[\alpha]_D^{26}$ −1.94 (c 0.53, MeOH).

$^1$H NMR (DMSO-$d_6$, 400 MHz): δ 0.87 (3H, t, J=7.3 Hz), 1.19 (9H, s), 1.20-1.35 (2H, m), 1.45-1.60 (2H, m), 1.62-1.74 (2H, m), 2.55-2.70 (2H, m), 3.60-3.85 (2H, m), 6.90 (1H, d, J=8.6 Hz), 6.96-7.04 (2H, m), 7.22-7.30 (3H, m).

HRESIMS (+): 502.1582 (502.1584 calcd. for $C_{23}H_{34}ClNO_5PS$)

Elemental analysis: measured C, 53.85%; H, 6.44%; N, 2.55%; calcd. for $C_{23}H_{33}ClNO_5PS \cdot 0.5H_2O$ C, 54.06%; H, 6.71%; N, 2.74%.

Example 22

(S)-2-amino-4-[2-chloro-4-(2-hydroxy-5-biphenylthio)phenyl]-2-propylbutylphosphoric acid monoester

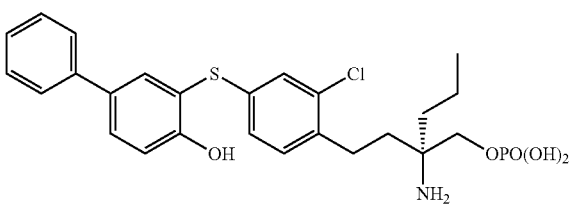

[Formula 174]

The target product (219 mg) was obtained as a white powder by reacting the compound of Reference Example 90 (400 mg) in the same manner as in Example 1.

Optical rotation: $[\alpha]_D^{26}$ −1.32 (c 0.50, MeOH).

$^1$H NMR (DMSO-$d_6$, 400 MHz): δ 0.86 (3H, t, J=7.3 Hz), 1.20-1.35 (2H, m), 1.45-1.62 (2H, m), 1.64-1.76 (2H, m), 2.58-2.68 (2H, m), 3.68-3.80 (2H, m), 7.03-7.10 (2H, m), 7.13 (1H, d, J=1.8 Hz), 7.22-7.30 (2H, m), 7.38 (2H, t, J=8.0 Hz), 7.48-7.58 (4H, m).

HRESIMS (+): 522.1275 (522.1271 calcd. for $C_{25}H_{30}ClNO_5PS$).

Elemental analysis: measured C, 56.58%; H, 5.52%; N, 2.38%; calcd. for $C_{25}H_{29}ClNO_5PS \cdot 0.5H_2O$ C, 56.55%; H, 5.69%; N, 2.64%.

Example 23

(S)-2-amino-4-[4-(5-benzyloxy-2-hydroxyphenylthio)-2-chlorophenyl]-2-propylbutylphosphoric acid monoester

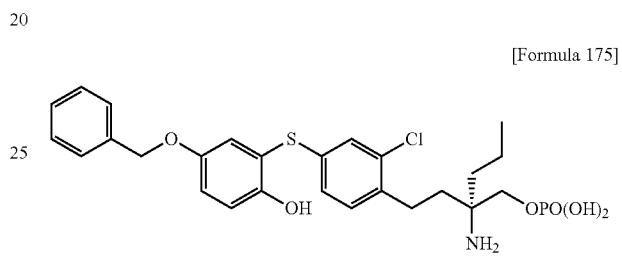

[Formula 175]

The target product (210 mg) was obtained as a white powder by reacting the compound of Reference Example 91 (430 mg) in the same manner as in Example 1.

Optical rotation: $[\alpha]_D^{26}$ −2.15 (c 0.50, MeOH).

$^1$H NMR (DMSO-$d_6$, 400 MHz): δ 0.88 (3H, t, J=7.3 Hz), 1.22-1.38 (2H, m), 1.46-1.62 (2H, m), 1.66-1.80 (2H, m), 2.56-2.70 (2H, m), 3.70-3.82 (2H, m), 4.96 (2H, s), 6.80 (1H, d, J=3.1 Hz), 6.85 (1H, d, J=8.6 Hz), 6.90 (1H, dd, J=8.6, 3.1 Hz), 7.07 (1H, dd, J=8.0, 1.8 Hz), 7.11 (1H, d, J=1.8 Hz), 7.24-7.38 (6H, m).

HRESIMS (+): 552.1384 (552.1377 calcd. for $C_{26}H_{32}ClNO_6PS$).

Elemental analysis: measured C, 54.89%; H, 5.53%; N, 2.52%; calcd. for $C_{26}H_{31}ClNO_6PS \cdot H_2O$ C, 54.78%; H, 5.48%; N, 2.46%.

Example 24

(S)-2-amino-4-[2-chloro-4-(2-hydroxy-5-trifluoromethylphenylthio)phenyl]-2-butylbutylphosphoric acid monoester

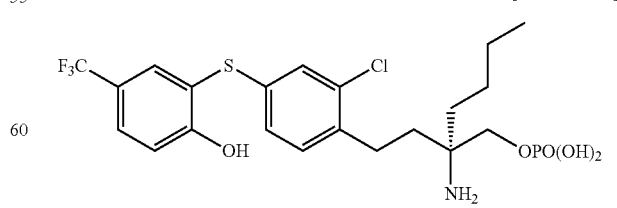

[Formula 176]

The target product (90 mg) was obtained as a white powder by reacting the compound of Reference Example 92 (250 mg) in the same manner as in Example 1.

Optical rotation: $[\alpha]_D^{26}$ -1.76 (c 0.50, MeOH).

$^1$H NMR (DMSO-d$_6$, 400 MHz): δ 0.86 (3H, t, J=7.3 Hz), 1.20-1.32 (4H, m), 1.50-1.64 (2H, m), 1.68-1.80 (2H, m), 2.60-2.70 (2H, m), 3.70-3.80 (2H, m), 7.11 (2H, m), 7.22 (1H, d, J=1.8 Hz), 7.30 (1H, d, J=8.6 Hz), 7.40 (1H, d, J=1.8 Hz), 7.52 (1H, dd, J=8.6, 1.8 Hz).

HRESIMS (+): 528.0985 (528.0988 calcd. for C$_{21}$H$_{27}$ClF$_3$NO$_5$PS).

Elemental analysis: measured C, 47.06%; H, 4.92%; N, 2.22%; calcd. for C$_{21}$H$_{26}$ClF$_3$NO$_5$PS. ½H$_2$O C, 46.98%; H, 5.07%; N, 2.61%.

Example 25

(S)-2-amino-4-[2-chloro-4-(2-hydroxy-5-carboxyphenylthio)phenyl]-2-propylbutylphosphoric acid monoester

[Formula 177]

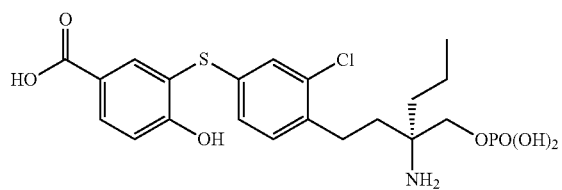

A 1 mol/L potassium hydroxide aqueous solution (2.00 ml) was added to the compound of Example 13 (100 mg), and the resultant solution was stirred at 50° C. for 2 hours. The reaction solution was cooled to room temperature, and 3 mol/L hydrochloric acid was added to adjust the pH to 6, whereby a solid precipitated. The precipitated solid was removed by filtration to obtain the target product (75.0 mg) as a white powder.

Optical rotation: $[\alpha]_D^{25}$ -5.00 (c 0.10, DMSO).

$^1$H NMR (DMSO-d$_6$, 400 MHz): δ 0.87 (3H, t, J=6.7 Hz), 1.30 (2H, br), 1.53 (2H, br), 1.68 (2H, br), 2.62 (2H, br), 3.70-3.75 (2H, m), 6.90 (1H, d, J=8.0 Hz), 7.02-7.06 (1H, m), 7.15 (1H, d, J=1.8 Hz), 7.26 (1H, d, J=8.6 Hz), 7.65-7.72 (2H, m).

HRESIMS (+): 490.0857 (490.0856 calcd. for C$_{20}$H$_{26}$ClNO$_7$PS).

Elemental analysis: measured C, 44.94%; H, 4.89%; N, 2.51%; calcd. for C$_{20}$H$_{25}$ClNO$_7$PS. 0.7 NaCl C, 45.25%; H, 4.75%; N, 2.64%.

Reference Example 93

(S)-2-t-butoxycarbonylamino-4-[2-chloro-4-(2-methoxy-5-trifluoromethylphenylthio)phenyl]-2-propylbutan-1-ol

[Formula 178]

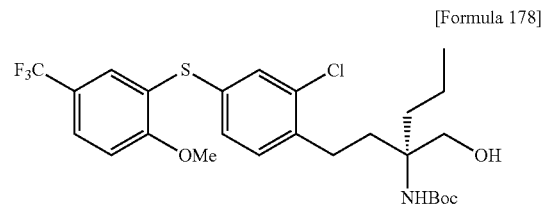 [SMILES: CCC[C@@](CO)(CCc1ccc(Sc2cc(C(F)(F)F)ccc2OC)cc1Cl)NC(=O)OC(C)(C)C]

The target product (19.2 g) was obtained as a colorless oil by reacting the compound of Reference Example 19 (11.0 g) and the compound of Reference Example 74 (18.5 g) in the same manner as in Reference Example 20.

$^1$H NMR (CDCl$_3$, 400 MHz): δ 0.96 (3H, t, J=7.3 Hz), 1.29-1.43 (2H, m), 1.44 (9H, s), 1.59 (2H, dd, J=7.3, 1.8 Hz), 1.83 (1H, ddd. J=13.9, 12.1, 5.4 Hz), 1.96 (1H, ddd, J=13.9, 12.1, 5.4 Hz), 2.63-2.78 (2H, m), 3.75 (2H, d, J=6.7 Hz), 3.92 (3H, s), 4.17 (1H, br s), 4.64 (1H, s), 6.96 (1H, d, J=8.5 Hz), 7.17 (1H, dd, J=8.5, 1.8 Hz), 7.17 (1H, d, J=8.5 Hz), 7.32-7.35 (2H, m), 7.51 (1H, dd, J=8.5, 1.8 Hz).

ESIMS (+): 548 [M+H]$^+$.

Reference Example 94

(S)-2-t-butoxycarbonylamino-4-[2-chloro-4-(2-hydroxy-5-trifluoromethylphenylthio)phenyl]-2-propylbutan-1-ol

[Formula 179]

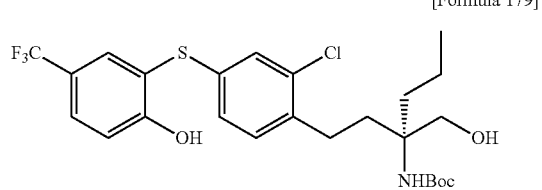

The target product (3.34 g) was obtained as a colorless oil by reacting the compound of Reference Example 93 (3.69 g) in the same manner as in Reference Example 33.

$^1$H NMR (CDCl$_3$, 400 MHz): δ 0.95 (3H, t, J=7.3 Hz), 1.28-1.41 (2H, m), 1.44 (9H, s), 1.59 (2H, dd, J=7.3, 1.8 Hz), 1.79 (1H, ddd. J=13.9, 11.6, 5.5 Hz), 1.90 (1H, ddd, J=13.9, 11.6, 5.5 Hz), 2.57-2.72 (2H, m), 3.72 (2H, d, J=6.7 Hz), 4.16 (1H, br s), 4.61 (1H, br s), 6.77 (1H, s), 6.91 (1H, dd, J=7.9, 1.8 Hz), 7.09 (1H, d, J=1.8 Hz), 7.13 (1H, d, J=7.9 Hz), 7.16 (1H, J=7.9 Hz), 7.63 (1H, dd, J=7.9, 1.8 Hz), 7.80 (1H, d, J=1.8 Hz).

ESIMS (+): 534 [M+H]$^+$.

Reference Example 95

(S)-2-t-butoxycarbonylamino-4-[2-chloro-4-(2-methoxymethoxy-5-trifluoromethylphenylthio)phenyl]-2-propylbutan-1-ol

[Formula 180]

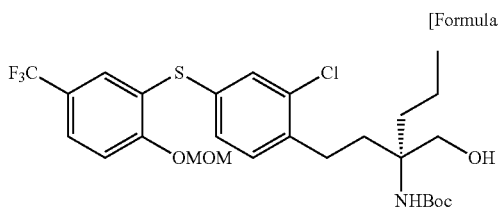

The target product (1.05 g) was obtained as a colorless oil by reacting the compound of Reference Example 94 (1.00 g) in the same manner as in Reference Example 58.

$^1$H NMR (CDCl$_3$, 400 MHz): δ 0.96 (3H, t, J=7.3 Hz), 1.30-1.43 (2H, m), 1.44 (9H, s), 1.54-1.60 (2H, m), 1.82 (1H, ddd, J=13.9, 12.1, 5.4 Hz), 1.94 (1H, ddd, J=13.9, 12.1, 5.4 Hz), 2.63-2.78 (2H, m), 3.40 (3H, s), 3.74 (2H, d, J=3.0 Hz), 4.16 (1H, br s) 4.63 (1H, s), 5.25 (2H, s), 7.16-7.23 (3H, m), 7.36 (2H, dd, J=8.5, 1.8 Hz), 7.47 (1H, dd, J=8.5, 1.8 Hz).

ESIMS (+): 578 [M+H]$^+$.

Reference Example 96

(S)-2-t-butoxycarbonylamino-4-[2-chloro-4-(2-methoxymethoxy-5-trifluoromethylphenylthio)phenyl]-2-propylbutan-1-al

[Formula 181]

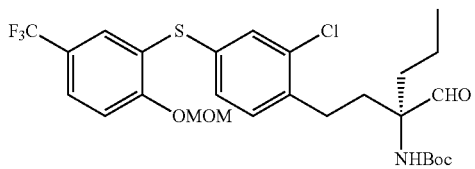

The target product (940 mg) was obtained as a colorless oil by reacting the compound of Reference Example 95 (1.05 g) in the same manner as in Reference Example 67.

$^1$H NMR (CDCl$_3$, 400 MHz): δ 0.96 (3H, t, J=7.3 Hz), 1.30-1.43 (2H, m), 1.46 (9H, s), 1.53-1.64 (2H, m), 1.89-2.30 (2H, m), 2.56 (1H, ddd, J=13.4, 12.2, 4.9 Hz), 2.65 (1H, ddd, J=13.4, 12.2, 4.9 Hz), 3.41 (3H, s), 5.23 (1H, br s), 5.25 (2H, s), 7.12 (1H, d, J=7.9 Hz), 7.19 (1H, dd, J=7.9, 1.8 Hz), 7.22 (1H, d, J=7.9 Hz), 7.31 (1H, d, J=1.8 Hz), 7.38 (1H, d, J=1.8 Hz), 7.48 (1H, dd, J=7.9, 1.8 Hz), 9.34 (1H, s).

ESIMS (+): 576 [M+H]$^+$.

Reference Example 97

Dimethyl(S)-3-t-butoxycarbonylamino-5-[2-chloro-4-(2-methoxymethoxy-5-trifluoromethylphenylthio)phenyl]-3-propyl-1-pentenylphosphonate

[Formula 182]

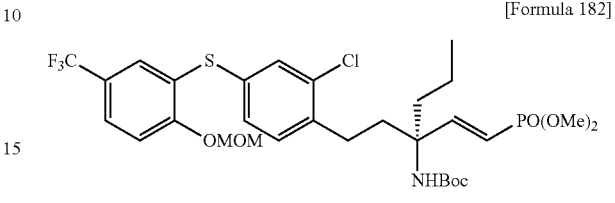

The target product (662 mg) was obtained as a colorless oil by reacting the compound of Reference Example 96 (940 mg) in the same manner as in Reference Example 68.

$^1$H NMR (CDCl$_3$, 400 MHz): δ 0.95 (3H, t, J=7.3 Hz), 1.30-1.44 (2H, m), 1.46 (9H, s), 1.52-1.65 (2H, m), 1.92 (1H, td, J=12.2, 4.9 Hz), 2.02-2.16 (1H, m), 2.62-2.80 (2H, m), 3.41 (3H, s), 3.72 (6H, d, J=11.0 Hz), 4.63 (1H, br s), 5.22 (2H, s), 5.73 (1H, t, J=17.7 Hz), 6.81 (1H, dd, J=22.6, 17.7 Hz), 7.16-7.19 (2H, m), 7.22 (1H, d, J=8.6 Hz), 7.35 (1H, d, J=1.8 Hz), 7.36 (1H, d, J=1.8 Hz), 7.50 (1H, dd, J=8.6, 1.8 Hz).

ESIMS (+): 682 [M+H]$^+$.

Reference Example 98

Dimethyl(S)-3-t-butoxycarbonylamino-5-[2-chloro-4-(2-methoxymethoxy-5-trifluoromethylphenylthio)phenyl]-3-propylpentylphosphonate

[Formula 183]

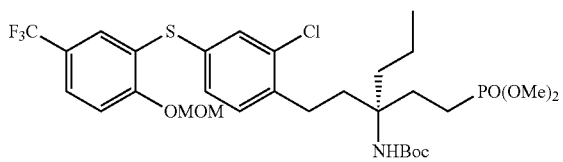

The target product (290 mg) was obtained as a colorless oil by reacting the compound of Reference Example 97 (662 mg) in the same manner as in Reference Example 69.

$^1$H NMR (CDCl$_3$, 400 MHz): δ 0.95 (3H, t, J=7.3 Hz), 1.26-1.40 (2H, m), 1.44 (9H, s), 1.52-1.65 (2H, m), 1.65-1.86 (4H, m), 2.04-2.28 (2H, m), 2.60-2.72 (2H, m), 3.41 (3H, s), 3.74 (6H, d, J=11.0 Hz), 4.27 (1H, br s), 5.25 (2H, s), 7.10-7.28 (3H, m), 7.38-7.42 (2H, m), 7.52 (1H, dd, J=7.9, 2.4 Hz).

ESIMS (+): 684 [M+H]$^+$.

Example 26

(S)-3-amino-5-[2-chloro-4-(2-hydroxy-5-trifluoromethylphenylthio)phenyl]-3-propylpentylphosphonic acid

[Formula 184]

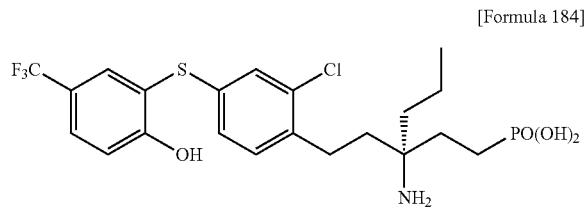

The target product (30 mg) was obtained as a white powder by reacting the compound of Reference Example 98 (250 mg) in the same manner as in Example 1.

Optical rotation: $[\alpha]_D^{25}$ -17.81 (c 0.10, MeOH).

$^1$H NMR (DMSO-d$_6$, 400 MHz): δ 0.95 (3H, t, J=7.3 Hz), 1.22-1.58 (6H, m), 1.64-1.86 (4H, m), 2.52-2.78 (2H, m), 7.09 (2H, d, J=8.6 Hz), 7.23 (1H, s), 7.25-7.33 (1H, m), 7.41 (1H, s), 7.49 (1H, d, J=8.6 Hz).

ESIMS (+): 512 [M+H]$^+$.

Results supporting the effectiveness of the compounds illustrated as examples will now be shown in Experiment Examples 1, 2, 3 and 4.

Experiment Example 1

Suppression Effect of Test Compound Against Cellular Calcium Mobilization of Human S1P3 Receptor-Expression Cell by S1P (Sphingosine 1-Phosphoric Acid)

Human S1P3 receptor-expression CHO cells were subcultured in a Ham's F-12 culture medium containing 10% fetal bovine serum, and 300 μg/mL of Geneticin. The human S1P3 receptor-expression CHO cells were subjected to 0.25% trypsinization, then recovered from the dish, and floated in a Ham's F-12 culture medium containing 10% fetal bovine serum, and 300 μg/mL of Geneticin. After that, the human S1P3 receptor-expression CHO cells were disseminated into a 96-well black clear bottom plate (BD Falcon Biocoat) so that 7×10$^4$/100 μL/well of the human S1P3 receptor-expression CHO cells were disseminated. And then, the human S1P3 receptor-expression CHO cells were cultivated for one night at 37° C. under 5% CO$_2$. The next day, the wells were washed 3 times with 100 μL of PBS containing 0.1% fatty acid-free bovine serum albumin (BSA). The culture medium was exchanged with a Ham's F-12 culture medium containing 0.1% BSA, and then starved of serum for 6 hours in an CO$_2$ incubator at 37° C.

The culture medium was thrown away after the 6 hours. Then, 50 μL/well of a Fluo3 loading buffer was added, and the cultures were cultivated for further 1 hour. The Fluo3 loading buffer was prepared as follows. First, equal amounts of Fluo3-AM (Dojindo) and pluronic F-127 (20% DMSO solution, invitrogen) were mixed. Next, the mixture of Fluo3-AM and pluronic F-127 was added to a Hanks-HEPES buffer (balanced salt solution containing 20 mM HEPES (pH, 7.4), 0.1% BSA (fatty acid-free), and 2.5 mM probenecid) to form a Fluo3 loading buffer having a final Fluo3-AM concentration of 4

After incubating for 1 hour, the cultures were washed 3 times with 100 μL of the Hanks-HEPES buffer. Then, 100 μL of the same buffer in which a test compound (125 nM, 1.25 μM, 12.5 μM) or DMSO had been dissolved was added to the cultures, and then incubated for 30 minutes at 37° C. in a microplate spectrophotofluorometer (FLEX Station) (Molecular Device Co., Ltd.). Then, 25 μL of S1P prepared at 5 times the concentration of the final concentration by serial dilution (final concentration of 0.1 nM, 1 nM, 10 nM, 100 nM, and 1 μM) was added, and the fluorescence based on the Fluo3 due to calcium mobilization was detected and measured at an excitation wavelength of 485 nm and a detection wavelength of 525 nm using the same apparatus. Based on the measurement data, the increase in fluorescence was calculated by subtracting the minimum fluorescence intensity from the maximum fluorescence intensity. The measured increase in fluorescence was used to perform a curve approximation of the relationship between the S1P concentration and the increase in fluorescence using PRISM 4 software (GraphPad). Based on the results, the EC50 value of the compound-untreated and the EC50 value of the compound-treated at each concentration were calculated. Schild Plot analysis was performed based on these values to determine dissociation constant Kd value. The results are shown in Table 1. In Table 1, 1,000 nmol/L>Kd value≥100 nmol/L is indicated as "+," 100 nmol/L>Kd value≥10 nmol/L is indicated as "++," 10 nmol/L>Kd value≥1 nmol/L is indicated as "+++," and 1 nmol/L>Kd value is indicated as "++++."

TABLE 1

| Example Number | S1P3 |
|---|---|
| 1 | ++ |
| 2 | ++ |
| 3 | ++ |
| 4 | +++ |
| 5 | +++ |
| 6 | + |
| 7 | ++ |
| 8 | ++ |
| 9 | +++ |
| 10 | ++ |
| 11 | +++ |
| 12 | ++++ |
| 13 | ++++ |
| 14 | ++ |
| 15 | + |
| 16 | ++ |
| 17 | + |
| 18 | +++ |
| 19 | +++ |
| 20 | +++ |
| 21 | ++++ |
| 22 | ++++ |
| 23 | +++ |

Experiment Example 2

Intracellular Calcium Mobilization Derivative Test of Test Compound Against Human S1P1 Receptor-Expression Cell Human S1P receptor-expression CHO cells (hS1P$_1$ receptor-expression CHO cells, hS1P$_3$ receptor-expression CHO cells, and hS1P$_4$ receptor-expression CHO cells) subcultured in a Ham's F-12 culture medium containing 10% fetal bovine serum, and 200 μg/mL of Geneticin were disseminated into a 96-well black clear bottom plate (coaster) so that 4×10$^4$ cells/well of the human S1P receptor-expression CHO cells were disseminated. The human S1P3 receptor-expression CHO cells were then cultivated for one night at 37° C. under 5% $CO_2$. A Calcium Screening Kit reagent (Dojindo) was added as a $Ca^{2+}$ binding fluorescence indicator, and then the cultures were cultivated for 60 minutes at 37° C. under 5% $CO_2$. After cultivation, the fluoroesence intensity was measured at an excitation wavelength of 485 nm and a detection wavelength of 525 nm using a microplate spectrophotofluorometer (FLEX Station) (Molecular Device Co., Ltd.). S1P prepared in a culture medium so that the concentration would be 10 times that of the final concentration, or a test compound (final DMSO concentration 0.1%) was added 18 seconds after the start of the fluorescence measurement, and the fluorescence intensity was continuously measured every 1.5 seconds until 100 seconds after the addition. Based on the measurement data, the increase in fluorescence was calculated by subtracting the minimum fluorescence intensity from the maximum fluorescence intensity. The percentage increase in fluorescence (%) of the test compound was calculated based on a difference of 100% between the increase in fluorescence when the solvent was added and the increase in fluorescence when acted on by $10^{-6}$ M S1P. The $EC_{50}$ value was determined using PRISM software (GraphPad) as the intracellular calcium mobilization derivative action of the test compound.

The $EC_{50}$ values of the compounds of Example 13 and Example 15 were larger than 10 μmol/L. Further, an evaluation of the antagonistic action of the S1P1 receptor using the method of Experiment Example 1 showed that the Kd values of the compounds of Example 13 and Example 15 were larger than 100 μmol/L.

Experiment Example 3

LPS Induced Sepsis Model

The experiment was carried out with reference to the method described in Non-Patent Literature 5 (F. Nissen et al., Nature, 452, 654 (2008)). A solution of 1 mg/ml LPS (lipopolysaccharide) in physiological saline was intraperitoneally administered (10 ml/kg) to a C57BL/6J mouse (Charles River, male, 7 to 8 weeks). The test compound in an amount of 10 mg/kg was intravenously administered twice, 15 minutes before LPS administration and 2 hours after LPS administration. The mouse was dissected 18 hours after LPS administration, and the mesenteric lymph nodes and lungs were excised. The mesenteric lymph nodes were dissolved in 200 μl and the lungs in 1 ml of a dissolving buffer (30 mM Tris (pH7.4), 150 mM NaCl, 0.1% TritonX-100, 2 mM $CaCl_2$, and 2 mM $MgCl_2$). Non-dissolved matter was removed by centrifugal separation. The IL-1β in the tissue solutions was measured using an IL-1β ELISA Kit (Thermo Co., Ltd.). The results are shown in Table 2. In Table 2, compounds having a suppression rate of 50% or more are indicated as "+++," compounds having a suppression rate of 50%>suppression rate≥30% are indicated as "++," and compounds having a suppression rate of 30%>suppression rate 20% are indicated as "+."

The suppression rate was calculated using the following calculation equation.

$$a = (1 - X/Y) \times 100 \quad \text{[Equation 1]}$$

X: IL-1β PRODUCTION AMOUNT WHEN, 10 mg/kg OF TEST COMPOUND WAS ADMINISTERED TO RESPECTIVE TISSUE
Y: IL-1β PRODUCTION AMOUNT WHEN TEST COMPOUND WAS NOT ADMINISTERED TO RESPECTIVE TISSUE a: SUPPRESSION RATE (%)

TABLE 2

| Example Number | Suppression Rate for Lung | Suppression Rate for Mesenteric Lymph Nodes |
|---|---|---|
| 11 | ++ | ++ |
| 12 | ++ | + |
| 13 | +++ | +++ |

Experimental Example 4

Cecal Ligation and Puncture Sepsis Model

This model is widely used as a model for polymicrobial abdominal sepsis caused by leakage of intestinal bacteria. The experiment was carried out with reference to the method described in Non-Patent Literature 9 (D. Rittirsch et al., Nature Protocols, 4, 31 (2009)). Long-Evans rats were used (Nihon SLC, male 9 weeks). The abdominal portion of the rats was cut open under isoflurane anesthesia, and the cecum was removed. The cecum was ligated with silk thread, and 3 holes were opened in the tip portion of the cecum using an 18 G syringe needle. After the treatment, the cecum was returned to the body, and the wound was sutured. The rats were then returned to their cages, and observed for 4 days to determine the survival rate. The test compound (0.1 mg/kg/hr) was continuously administered from a cannula stuck in the femoral vein from 2 hours after the CLP treatment.

The group administered with the compound of Example 22 was found to have a survival curve that had shifted to the right as compared with the medium administration group (survival lengthening action). Further, although the survival rate after 4 days was 40% for the medium group, an improvement in the survival rate to 70% was found for the compound of Example 22. These results suggest that the compound of Example 22 is effective against sepsis.

Based on the above results, it is clear that despite exhibiting an excellent antagonistic action against the human $S1P_3$ receptor, the compound of the present invention exhibits a weak or no antagonistic action or agonistic action against the S1P1 receptor. Further, it was also confirmed that the compound of the present invention exhibits an excellent suppressive effect against sepsis.

INDUSTRIAL APPLICABILITY

According to the present invention, a diphenyl sulfide derivative can be provided that has an excellent S1P3 antagonistic activity. The inventive compound is effective as a preventive or a therapeutic medicine for respiratory tract contraction, bronchial asthma, chronic obstructive pulmonary disease (COPD), pulmonary emphysema, tracheal stenosis, diffuse panbronchiolitis, bronchitis resulting from infection, connective tissue disease, or transplantation, diffuse pulmonary hamartoangiomyomatosis, adult respiratory distress syndrome (ARDS), interstitial pneumonitis, lung cancer, pneumonia hypersensitivity, idiopathic interstitial pneumonia, fibrosis of the lung, or cytokine storm caused by an influenza virus or RS virus infection, arterial sclerosis, blood vessel intimal hypertrophy, solid tumors, diabetic retinopathy, rheumatoid arthritis, cardiac arrest, ischemia-reperfusion disorders, cerebral blood vessel spasms after subarachnoid bleeding, angina pectoris or myocardial infarction caused by coronary vessel spasms, glomerulonephritis, thrombosis, lung disease caused by pulmonary edema such as ARDS, cardiac arrhythmia, eye disease, eye hypertension, glaucoma, glaucomatous retinopathy, optic neuropathy, and macula-lutea degeneration.

The invention claimed is:

1. A diphenyl sulfide compound, or a pharmaceutically acceptable salt or hydrate thereof, represented by formula (1),

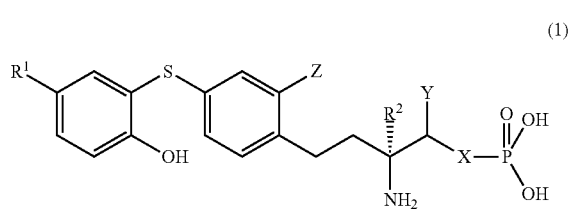

(1)

wherein $R^1$ represents a hydrogen atom, a halogen atom, a trifluoromethyl group, an optionally substituted alkyl group having 1 to 6 carbon atoms, an optionally substituted cycloalkyl group having 3 to 6 carbon atoms, an optionally substituted aryl group having 6 to 10 carbon atoms, an optionally substituted alkoxy group having 1 to 4 carbon atoms, an optionally substituted benzyloxy group, an optionally substituted acyl group having 1 to 4 carbon atoms, a cyano group, or a carboxyl group; $R^2$ represents an optionally substituted alkyl group having 1 to 6 carbon atoms or an optionally substituted alkenyl group having 2 to 6 carbon atoms; X represents a methylene group which may be substituted with 1 or 2 fluorine atoms or represents an oxygen atom; Y represents a hydrogen atom or an optionally substituted alkyl group having 1 to 6 carbon atoms; and Z represents a halogen atom.

2. The diphenyl sulfide compound according to claim 1, or a pharmaceutically acceptable salt or hydrate thereof, wherein the compound is represented by formula (1a),

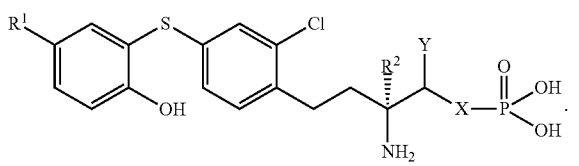

(1a)

3. The diphenyl sulfide compound according to claim 1, or a pharmaceutically acceptable salt or hydrate thereof, wherein the compound is represented by formula (1b),

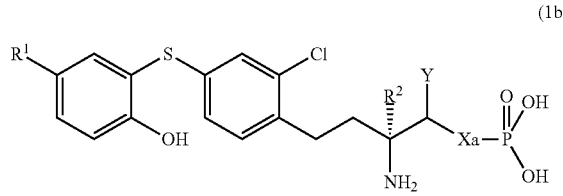

(1b)

wherein Xa represents an oxygen atom or —CH$_2$—.

4. The diphenyl sulfide compound according to claim 1, or a pharmaceutically acceptable salt or hydrate thereof, wherein the compound is represented by formula (1c),

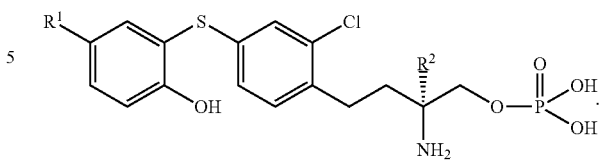

(1c)

5. The diphenyl sulfide compound according to claim 4, or a pharmaceutically acceptable salt or hydrate thereof, wherein $R^1$ represents a trifluoromethyl group, an alkyl group having 1 to 6 carbon atoms, a cycloalkyl group having 3 to 6 carbon atoms, an aryl group having 6 to 10 carbon atoms, or a benzyloxy group.

6. The diphenyl sulfide compound according to claim 1, or a pharmaceutically acceptable salt or hydrate thereof, wherein the compound represented by formula (1) is (S)-2-amino-4-[2-chloro-4-(2-hydroxy-5-trifluoromethylphenylthio)phenyl]-2-propylbutylphosphoric acid monoester, (R)-2-allyl-2-amino-4-[2-chloro-4-(2-hydroxy-5-trifluoromethylphenylthio)phenyl]butylphosphoric acid monoester, (S)-2-amino-4-[2-chloro-4-(2-hydroxy-5-trifluoromethylphenylthio)phenyl]-2-methylbutylphosphoric acid monoester, (S)-2-amino-4-[2-chloro-4-(2-hydroxy-5-isopropylphenylthio)phenyl]-2-methylbutylphosphoric acid monoester, (S)-2-amino-4-[2-chloro-4-(5-cyclopropyl-2-hydroxyphenylthio)phenyl]-2-methylbutylphosphoric acid monoester, (S)-2-amino-4-[4-(5-benzyloxy-2-hydroxyphenylthio)-2-chlorophenyl]-2-methylbutylphosphoric acid monoester, (S)-2-amino-4-[2-chloro-4-(2-hydroxy-5-propylphenylthio)phenyl]-2-propylbutylphosphoric acid monoester, (S)-2-amino-4-[2-chloro-4-(2-hydroxy-5-isopropylphenylthio)phenyl]-2-propylbutylphosphoric acid monoester, (S)-2-amino-4-[2-chloro-4-(5-cyclopropyl-2-hydroxyphenylthio)phenyl]-2-propylbutylphosphoric acid monoester, (S)-2-amino-4-[4-(5-t-butyl-2-hydroxyphenylthio)-2-chlorophenyl]-2-propylbutylphosphoric acid monoester, (S)-2-amino-4-[2-chloro-4-(2-hydroxy-5-biphenylthio)phenyl]-2-propylbutylphosphoric acid monoester, or (S)-2-amino-4-[4-(5-benzyloxy-2-hydroxyphenylthio)-2-chlorophenyl]-2-propylbutylphosphoric acid monoester.

7. The diphenyl sulfide compound according to claim 1, or a pharmaceutically acceptable salt or hydrate thereof, wherein the compound represented by formula (1) is (−)-2-amino-4-[2-chloro-4-(2-hydroxy-5-trifluoromethylphenylthio)phenyl]-2-propylbutylphosphoric acid monoester, (−)-2-allyl-2-amino-4-[2-chloro-4-(2-hydroxy-5-trifluoromethylphenylthio)phenyl]butylphosphoric acid monoester, (−)-2-amino-4-[2-chloro-4-(2-hydroxy-5-trifluoromethylphenylthio)phenyl]-2-methylbutylphosphoric acid monoester, (−)-2-amino-4-[2-chloro-4-(2-hydroxy-5-isopropylphenylthio)phenyl]-2-methylbutylphosphoric acid monoester, (−)-2-amino-4-[2-chloro-4-(5-cyclopropyl-2-hydroxyphenylthio)phenyl]-2-methylbutylphosphoric acid monoester, (−)-2-amino-4-[4-(5-benzyloxy-2-hydroxyphenylthio)-2-chlorophenyl]-2-methylbutylphosphoric acid monoester, (−)-2-amino-4-[2-chloro-4-(2-hydroxy-5-propylphenylthio)phenyl]-2-propylbutylphosphoric acid monoester, (−)-2-amino-4-[2-chloro-4-(2-hydroxy-5-isopropylphenylthio)phenyl]-2-propylbutylphosphoric acid monoester, (−)-2-amino-4-[2-chloro-4-(5-cyclopropyl-2-hydroxyphenylthio)phenyl]-2-propylbutylphosphoric acid monoester, (−)-2-amino-4-[4-(5-t-butyl-2-hydroxyphenylthio)-2-chlorophenyl]-2-propylbutylphosphoric acid monoester, (−)-2-amino-4-[2-chloro-4-(2-hydroxy-5-biphenylthio)phenyl]-2-propylbutylphosphoric acid monoester, or (+2-amino-4-[4-(5-benzyloxy-2-hydroxyphenylthio)-2-chlorophenyl]-2-propylbutylphosphoric acid monoester.

8. A pharmaceutical composition comprising the diphenyl sulfide compound according to claim 1, or a pharmaceutically acceptable salt or hydrate thereof, and a pharmaceutically acceptable carrier.

9. A method of inducing a sphingosine-1-phosphate 3 (S1P3) receptor-antagonistic action comprising administering the pharmaceutical composition according to claim 8 to a patient in need thereof.

10. A method for the treatment of sepsis comprising administering the pharmaceutical composition according to claim 8 to a patient in need thereof.

* * * * *